(12) United States Patent
Hu et al.

(10) Patent No.: US 6,251,918 B1
(45) Date of Patent: Jun. 26, 2001

(54) ANILINE DERIVATIVES AS CALCIUM CHANNEL BLOCKERS

(75) Inventors: Lain-Yen Hu; Michael Francis Rafferty; Todd Robert Ryder, all of Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/402,196

(22) PCT Filed: Jul. 29, 1998

(86) PCT No.: PCT/US98/15907
§ 371 Date: Sep. 29, 1999
§ 102(e) Date: Sep. 29, 1999

(87) PCT Pub. No.: WO99/07689
PCT Pub. Date: Feb. 18, 1999

Related U.S. Application Data

(60) Provisional application No. 60/055,251, filed on Aug. 11, 1997, and provisional application No. 60/082,358, filed on Apr. 20, 1998.

(51) Int. Cl.[7] ............... A61K 31/445; A61K 31/505; C07D 239/02; C07D 211/06
(52) U.S. Cl. ............ 514/317; 514/331; 514/258; 546/184; 546/247; 546/192; 546/205; 546/206
(58) Field of Search ............... 514/317, 331, 514/258; 546/184, 247, 192, 205, 206

(56) References Cited

U.S. PATENT DOCUMENTS 5,346,907 * 9/1994 Kerwin, Jr. et al. ............ 514/312

FOREIGN PATENT DOCUMENTS

| 94/24116 | 10/1994 | (WO) . |
| 9424116 | * 12/1994 | (WO) . |
| 9427967 | * 12/1994 | (WO) . |
| 94/27967 | 12/1994 | (WO) . |
| 96/11940 | 4/1996 | (WO) . |

OTHER PUBLICATIONS

Caplus 122:291527, Kerwin James et al, preparation of Amino acid . . . RN#247116–68–3, Sep. 1994.*

Caplus 131:295124, ryder todd et al, Bioorg. med. Chem. letteres. 1999, vol. 9 issue 16, Sep. 1994.*

* cited by examiner

*Primary Examiner*—Alan L. Rotman
*Assistant Examiner*—Rita Desai
(74) *Attorney, Agent, or Firm*—Todd M. Crissey; Charles W. Ashbrook

(57) ABSTRACT

The present invention provides compounds that block calcium channels having formula (I). The present invention also provides methods of using the compounds of formula (I) to treat stroke, cerebral ischemia, head trauma, or epilepsy and to pharmaceutical compositions that contain the compounds of formula (I).

(I)

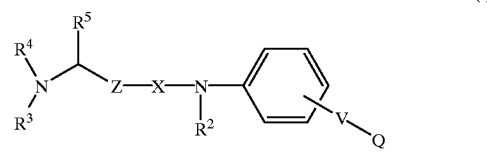

35 Claims, No Drawings

ANILINE DERIVATIVES AS CALCIUM CHANNEL BLOCKERS

This application is a 371 of Application No. PCT/US98/15907 filed Jul. 29, 1998, which claims benefit of provisional applications Nos. 60/055,251 filed Aug. 11, 1997, and 60/082,358 filed Apr. 20, 1998.

FIELD OF THE INVENTION

The present invention relates to compounds that act to block calcium channels; methods of using the compounds to treat stroke, cerebral ischemia, pain, head trauma or epilepsy; and to pharmaceutical compositions that contain the compounds of the present invention.

BACKGROUND OF THE INVENTION

The entry of excessive amounts of calcium ions into neurons following an ischemic episode or other neuronal trauma has been well documented. Uncontrolled high concentrations of calcium in neurons initiates a cascade of biochemical events that disrupts normal cellular processes. Among these events are the activation of proteases and lipases, breakdown of neuronal membranes and the formation of free radicals, which may ultimately lead to cell death. Several types of calcium channels have been discovered and called the L, N, P, Q, R, and T types. Each type possesses distinct structural features, functional properties and cellular/subcellular distributions. Type selective calcium channel blockers have been identified. For example, SNX-111 has been shown to be a selective N-type calcium channel blocker and has demonstrated activity in a number of models of ischemia and pain (Bowersox S. S., et al., *Drug News and Perspective,* 1994:7:261–268 and references cited therein). The compounds of the present invention are calcium channel blockers that can block N-type calcium channels and can be used to treat stroke, pain, cerebral ischemia, head trauma, and epilepsy.

SUMMARY OF THE INVENTION

The present invention provides compounds having the Formula I

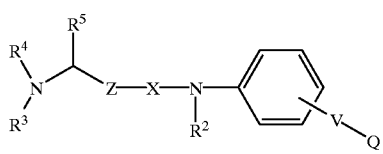

wherein each m is independently 1 to 3;

each n is independently 0 to 3;

each $R^a$ and $R^b$ is independently hydrogen, $C_1$–$C_6$alkyl, or $R^a$ and $R^b$ together with the carbon atom to which they are bonded form a $C_3$–$C_6$cycloalkyl ring;

Z is

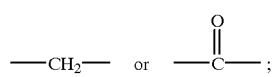

X is

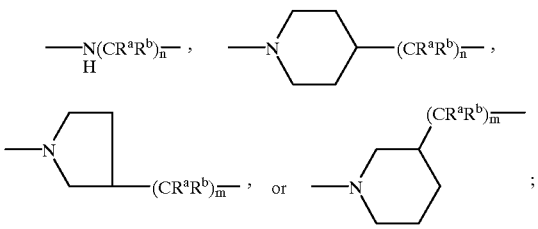

$R^5$ is $C_1$–$C_6$alkyl, —$(CH_2)_m$-heteroaryl, —$(CH_2)_m$-substituted heteroaryl, —$(CH_2)_m$-phenyl, or —$(CH_2)$-substituted phenyl;

$R^2$ is hydrogen, $C_1$–$C_8$alkenyl, $C_3$–$C_8$cycloalkenyl, phenyl, substituted phenyl, $C_1$–$C_8$alkyl, substituted $C_1$–$C_8$alkyl, —$(CH_2)_m$ substituted $C_3$–$C_8$cycloalkyl, —$(CH_2)_m$—$C_3$–$C_8$cycloalkyl, $C_3$–$C_8$cycloalkyl, substituted $C_3$–$C_8$cycloalkyl, —$(CH_2)_m$-phenyl, or —$(CH_2)_m$ substituted phenyl;

$R^3$ is hydrogen, $C_1$–$C_6$alkyl, or $C_2$–$C_6$alkenyl;

Q is aryl, heteroaryl, substituted heteroaryl, $C_3$–$C_8$cycloalkyl, substituted $C_3$–$C_8$cycloalkyl, $C_1$–$C_6$alkyl, substituted $C_1$–$C_6$alkyl, hydrogen, $C_3$–$C_8$heterocycloalkyl, $C_3$–$C_8$ substituted heterocycloalkyl, or substituted aryl;

V is

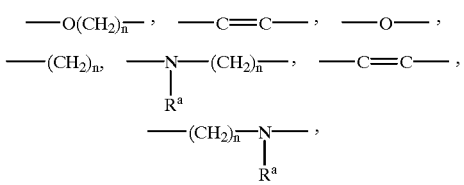

or —$(CH_2)_n$—O—;

$R^4$ is hydrogen,

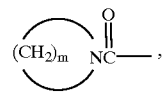

$C_1$–$C_6$alkyl, $C_2$–$C_8$alkenyl, $C_3$–$C_8$cycloalkenyl, $C_3$–$C_8$ substituted cycloalkenyl, —$(CH_2)_m$-phenyl, —$(CH_2)_m$-heteroaryl, —$(CH_2)_m$ substituted heteroaryl, —$(CH_2)_m$-substituted phenyl, $C_3$–$C_8$cycloalkyl, or $C_3$–$C_8$ substituted cycloalkyl;

or $R^3$ and $R^4$ together with the nitrogen atom to which they are bonded can form a 5–7 membered ring that can contain one or more heteroatom;

and the pharmaceutically acceptable salts, esters, amides, and prodrugs thereof.

In a preferred embodiment of the compounds of Formula I, V is —$OCH_2$— or $CH_2CH_2$, and Q is phenyl.

In another preferred embodiment of the compounds of Formula I,

X is

and Z is

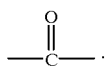

In another preferred embodiment of the compounds of Formula I, $R^3$ and
$R^4$ are both hydrogen.

In another preferred embodiment of the compounds of Formula I, $R^3$ is hydrogen and $R^4$ is

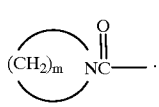

In another preferred embodiment of the compounds of Formula I, V is —$OCH_2$—;
Q is phenyl;
Z is

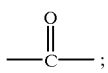

$R^3$ is hydrogen;
$R^4$ is

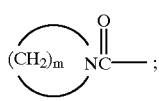

$R^2$ is $C_2$–$C_8$cycloalkenyl, $C_2$–$C_8$alkyl, or $C_2$–$C_8$alkenyl; and
$R^5$ is $C_1$–$C_8$alkyl.

In another preferred embodiment of the compounds of Formula I, Z is

and X is

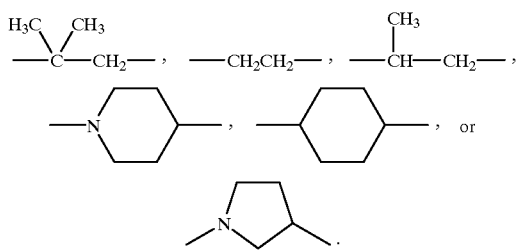

In still another preferred embodiment of the compounds of Formula I, $R^5$ is isobutyl, 3-methylbutyl, 2-methylbutyl, —$CH_2$-pyridyl, or —$CH_2$-imidazolyl.

In a preferred embodiment of the compounds of Formula I, $R^2$ is 3-methyl-but-2-enyl, or 3-methylbutyl, 2-methylpropyl, methyl, $CH_2$-cyclohexyl, n-butyl, or cyclohexyl.

In another preferred embodiment of the compounds of Formula I, V is —O—$CH_2$—, —C=C—, —$CH_2$—$CH_2$, or —NH—$CH_2$; Q is pyridyl, phenyl, cyclohexyl, or $C_1$–$C_8$alkyl.

In a most preferred embodiment, the compounds of Formula I are:
(S)-Azepane-1-carboxylic acid (1-{2-[(4-benzyloxy-phenyl)-(3-methyl-but-2enyl)-amino]-1,1-dimethyl-ethylcarbamoyl}-3-methyl-butyl)-amide;
[S-(R*,R*)]-Azepane-1-carboxylic acid (1-{2-[(4-benzyloxy-phenyl)-(3-methyl-but-2enyl)-amino]-1-methyl-ethylcarbamoyl}-3-methyl-butyl)-amide;
(S)-Azepane-1-carboxylic acid (1-{2-[(4-benzyloxy-phenyl)-3-methyl-but-2-enyl)-amino]-ethylcarbamoyl}-3-methyl-butyl)-amide;
(S)-Azepane-1-carboxylic acid (1-{3-[(4benzyloxy-phenyl)-(3-methyl-but-2-enyl)-amino]-propylcarbamoyl}-3-methyl-butyl)-amide;
(S)-Azepane-1-carboxylic acid (1-{4-[(4-benzyloxy-phenyl)-(3-methyl-but-2-enyl)-amino]-piperidine-1-carbonyl}-3-methyl-butyl)-amide;
(S)-Azepane-1-carboxylic acid (1-{2-[(4-benzyloxy-phenyl)-cyclohex-2-enyl-amino]-ethylcarbamoyl}-3-methyl-butyl)-amide;
(S)-Azepane-1-carboxylic acid (1-{2-[benzyl-(4-benzyloxy-phenyl)-amino]-ethylcarbamoyl}-3-methyl-butyl)-amide;
(S)-Azepane-1-carboxylic acid (1-{2-[(4-benzyloxy-phenyl)-cyclohex-2-enyl-amino]-1,1-dimethyl-ethylcarbamoyl}-3-methyl-butyl)-amide;
(S)-2-Dimethylamino-4-methyl-pentanoic acid {2-[(4-benzyloxy-phenyl)-(3-methyl-but-2-enyl)-amino]-1,1-dimethyl-ethyl}-amide;
(S)-4-Methyl-2-[methyl-(3-methyl-but-2-enyl)-amino]-pentanoic acid {2-[(4-benzyloxy-phenyl)-(3-methyl-but-2-enyl)-amino]-1,1-dimethyl-ethyl}-amide;
(S)-4-Methyl-2-[methyl-(3-methyl-butyl)-amino]-pentanoic acid {2-[(4-benzyloxy-phenyl)-(3-methyl-but-2-enyl)-amino]-1,1-dimethyl-ethyl}-amide;
(S)-2-(Cyclohex-2-enyl-methyl-amino)-4-methyl-pentanoic acid {2-[(4-benzyloxy-phenyl)-(3-methyl-but-2-enyl)-amino]-1,1-dimethyl-ethyl}-amide;
(S)-2-[(4-tert-Butyl-benzyl)-methyl-amino]-4-methyl-pentanoic acid {2-[(4-benzyloxy-phenyl)-(3-methyl-but-2-enyl)-amino-1,1-dimethyl-ethyl}-amide;
[S-(R*,R*)]-2-Dimethylamino-4-methyl-pentanoic acid {2-[(4-benzyloxy-phenyl)-(3-methyl-but-2-enyl)-amino]-1-methyl-ethyl}-amide;
[S-(R*,R*)]-4-Methyl-2-(3-methyl-but-2-enylamino)-pentanoic acid {2-[(4-benzyloxy-phenyl)-(3-methyl-but-2-enyl)-amino]-1-methyl-ethyl}-amide;
[S-(R*,R*)]-4-Methyl-2-(3-methyl-butylamino)-pentanoic acid {2-[(4benzyloxy-phenyl)-(3-methyl-but-2-enyl)-amino]-1-methyl-ethyl}-amide;
(S)-4-Methyl-2-[methyl-(3-methyl-butyl)-amino]-pentanoic acid {2-[(4-benzyloxy-phenyl)-cyclohex-2-enyl-amino]-1,1-dimethyl-ethyl}-amide;
[S-(R*,R*)]-2-[Bis-(3-methyl-butyl)-amino]-4-methyl-pentanoic acid {2-[(4-benzyloxy-phenyl)-(3-methyl-but-2-enyl)-amino]-1-methyl-ethyl}-amide; and
[S-(R*,R*)]-2-{Bis]-(3-methyl-but-2-enylamino)-4-methyl-pentanoic acid {2-[(4-benzyloxy-phenyl)-(3-methyl-but-2-enyl)-amino]-1-methyl-ethyl}-amide.

In a most preferred embodiment, the compounds of Formula I are:

2-Amino-4-methyl-pentanoic acid {2-[(4benzyloxy-phenyl)-(3-methyl-butyl)-amino]-1,1dimethyl-ethyl}-amide;
2-Benzylamino-4-methyl-pentanoic acid {2-[(4-benzyloxy-phenyl)-(3-methyl-butyl)-amino]-1,1-dimethyl-ethyl}-amide;
4-Methyl-2-(3-methyl-butylamino)-pentanoic acid {2-[(4-benzyloxy-phenyl)-(3-methyl-butyl)-amino]-1,1-dimethyl-ethyl}-amide;
2-(Cyclohexylmethyl-amino)-4-methyl-pentanoic acid {2-[(4-benzyloxy-phenyl)-(3-methyl-butyl)-amino]-1,1-dimethyl-ethyl}-amide;
2-Dimethylamino-4-methyl-pentanoic acid {2-[(4-benzyloxy-phenyl)-(3-methyl-butyl)-amino]-1,1-dimethyl-ethyl}-amide;
1{4-[(4-Benzyloxy-phenyl)-(3-methyl-butyl)-amino]-piperidin-1-yl}-2-isopropylamino-4-methyl-pentan-1-one;
2-Benzylamino-1-{4-[(4benzyloxy-phenyl)-(3-methyl-butyl)-amino]-piperidin-1-yl}-4-methyl-pentan-1-one;
1-{4-[(4-Benzyloxy-phenyl)-(3-methyl-butyl)-amino]-piperidin-1-yl}-4-methyl-2-(3-methyl-butylamino)-pentan-1-one;
1-{4-[(4-Benzyloxy-phenyl)-(3-methyl-butyl)-amino]-piperidin-1-yl}-2-cyclohexylamino-4-methyl-pentan-1-one;
1-{4-[(4-Benzyloxy-phenyl)-(3-methyl-butyl)-amino]-piperidin-1-yl}-2-dimethylamino-4-methyl-pentan-1-one;
2-Isopropylamino-4-methyl-pentanoic acid {2-[(4-benzyloxy-phenyl)-(3-methyl-butyl)-amino]-ethyl}-amide;
4-Methyl-2-(3-methyl-butylamino)-pentanoic acid {2-[(4-benzyloxy-phenyl)-(3-methyl-butyl)-amino]-ethyl}-amide;
2-Cyclohexylamino-4-methyl-pentanoic acid {2-[(4-benzyloxy-phenyl)-(3-methyl-butyl)-amino]-ethyl}-amide;
2-Isopropylamino-4-methyl-pentanoic acid {3-[(4-benzyloxy-phenyl)-(3-methyl-butyl)-amino]-propyl}-amide;
4-Methyl-2-(3-methyl-butylamino)-pentanoic acid {3-[(4-benzyloxy-phenyl)-(3-methyl-butyl)-amino]-propyl}-amide;
2-Cyclohexylamino-4-methyl-pentanoic acid {3-[(4-benzyloxy-phenyl)-(3-methyl-butyl)-amino]-propyl}-amide;
Azepane-1-carboxylic acid (1-{4-[(4-benzyloxy-phenyl)-(3-methyl-butyl)-amino]-piperidine-1-carbonyl}-3-methyl-butyl)-amide;
Azepane-1-carboxylic acid (1-{4-[(4-benzyloxy-phenyl)-(3-methyl-butyl)-amino]-piperidine-1-carbonyl}-2-methyl-butyl)-amide;
Azepane-1-carboxylic acid (1-{4-[(4-benzyloxy-phenyl)-(3-methyl-butyl)-amino]-piperidine-1-carbonyl}-2-methyl-propyl)-amide;
Azepane-1-carboxylic acid (1-{4-[(4-benzyloxy-phenyl)-(3-methyl-butyl)-amino]-piperidine-1-carbonyl}-2-pyridin-2-yl-ethyl)-amide;
Azepane-1-carboxylic acid (1-{4-[(4-benzyloxy-phenyl)-(3-methyl-butyl)-amino]-piperidine-1-carbonyl}-2-pyridin-4-yl-ethyl)-amide;
Azepane-1-carboxylic acid [1-{4-[(4-benzyloxy-phenyl)-(3-methyl-butyl)-amino]-piperidine-1-carbonyl}-2-(3H-imidazol-4-yl)-ethyl]-amide;
Azepane-1-carboxylic acid (1-{2-[(4-benzyloxy-phenyl)-(3-methyl-butyl)-amino]-1,1-dimethyl-ethylcarbamoyl}-3-methyl-butyl)-amide;
Azepane-1-carboxylic acid (1-{2-[(4-benzyloxy-phenyl)-(3-methyl-butyl)-amino]-1,1-dimethyl-ethylcarbamoyl}-2-methyl-butyl)-amide;
Azepane-1-carboxylic acid (1-{2-[(4-benzyloxy-phenyl)-(3-methyl-butyl)-amino]-1,1-dimethyl-ethylcarbamoyl}-2-methyl-propyl)-amide;
Azepane-1-carboxylic acid (1-{2-[(4-benzyloxy-phenyl)-(3-methyl-butyl)-amino]-1,1-dimethyl-ethylcarbamoyl}-2-pyridin-2-yl-ethyl)-amide;
Azepane-1-carboxylic acid (1-{2-[(4-benzyloxy-phenyl)-(3-methyl-butyl)-amino]-1,1-dimethyl-ethylcarbamoyl}-2-pyridin-4-yl-ethyl)-amide;
Azepane-1-carboxylic acid [1-{2-[(4-benzyloxy-phenyl)-(3-methyl-butyl)-amino]-1,1-dimethyl-ethylcarbamoyl}-2-(3H-imidazol-4-yl)-ethyl]-amide;
Azepane-1-carboxylic acid [1-({2-[(4-benzyloxy-phenyl)-(3-methyl-butyl)-amino]-1,1-dimethyl-ethylamino}-methyl)-3-butyl]-amide;
Azepane-1-carboxylic acid (1-{4-[(4-benzyloxy-phenyl)-(3-methyl-butyl)-amino]-piperidin-1-ylmethyl}-3-methyl-butyl)-amide;
Azepane-1-carboxylic acid [1-(1-{[(4-benzyloxy-phenyl)-(3-methyl-butyl)-amino]-methyl}-cyclobutylcarbamoyl)-3-methyl-butyl]-amide;
Azepane-1-carboxylic acid (1-{4-[(4-benzyloxy-phenyl)-(3-methyl-butyl)-amino-cyclohexylcarbamoyl}-3-methyl-butyl)-amide;
Azepane-1-carboxylic acid (1-{3-[(4-benzyloxy-phenyl)-(3-methyl-butyl)-amino]-piperidine-1-carbonyl}-3-methyl-butyl)-amide;
Azepane-1-carboxylic acid (1-{3-[(4-benzyloxy-phenyl)-(3-methyl-butyl)-amino]-pyrrolidine-1-carbonyl}-3-methyl-butyl)-amide;
Azepane-1-carboxylic acid (1-{2-[(4-benzyloxy-phenyl)-isobutyl-amino]-1,1-dimethyl-ethylcarbamoyl}-3-methyl-butyl)-amide;
Azepane-1-carboxylic acid (1-{2-[(4-benzyloxy-phenyl)-methyl-amino]-1,1-dimethyl-ethylcarbamoyl)-3-methyl-butyl)-amide;
Azepane-1-carboxylic acid (1-{2-[(4-benzyloxy-phenyl)-cyclohexylmethyl-amino]-1,1-dimethyl-ethylcarbamoyl}-3-methyl-butyl)-amide;
Azepane-1-carboxylic acid (1-{2-[(4-benzyloxy-phenyl)-cyclohexyl-amino]-1,1-dimethyl-ethylcarbamoyl)-3-methyl-butyl)-amide;
Azepane-1-carboxylic acid (1-{2-[(4-benzyloxy-phenyl)-(3-methyl-butyl)-amino]-1,1-dimethyl-ethylcarbamoyl}-3-methyl-butyl)-amide;
Azepane-1-carboxylic acid (1-{2-[(4-benzyloxy-phenyl)-butyl-amino]-1,1-dimethyl-ethylcarbamoyl}-3-methyl-butyl)-amide;
Azepane-1-carboxylic acid (1-4-[(benzyloxy-phenyl)-isobutyl-amino]-piperidine-1-carbonyl}-3-methyl-butyl)-amide;
Azepane-1-carboxylic acid (1-{4-[(4-benzyloxy-phenyl)-methyl-amino]-piperidine-1-carbonyl}-3-methyl-butyl)-amide;
Azepane-1-carboxylic acid (1-{4-[(4-benzyloxy-phenyl)-cyclohexylmethyl-amino)-piperidine-1-carbonyl}-3-methyl-butyl)-amide;
Azepane-1-carboxylic acid (1-{4-[(4-benzyloxy-phenyl)-cyclohexyl-amino]-piperidine-1-carbonyl}-3-methyl-butyl)-amide;
Azepane-1-carboxylic acid (1-{4-[(4-benzyloxy-phenyl)-(3-methyl-butyl)-amino]-piperidine-1-carbonyl}-3-methyl-butyl)-amide;
Azepane-1-carboxylic acid (1-{4-[(4-benzyloxy-phenyl)-butyl-amino]-piperidine-1-carbonyl}-3-methyl-butyl)-amide;

Azepane-1-carboxylic acid [3-methyl-1-(4-{(3-methyl-butyl)-[4-(pyridin-2-ylmethoxy)-phenyl]-amino}-piperidine-1-carbonyl)-butyl]-amide;
Azepane-1-carboxylic acid [3-methyl-1-(4-{(3-methyl-butyl)-[4-(pyridin-3-ylmethoxy)-phenyl]-amino}-piperidine-1-carbonyl)-butyl]-amide;
Azepane-1-carboxylic acid [3-methyl-1-(4-{(3-methyl-butyl)-[4-(pyridin-4-ylmethoxy)-phenyl]-amino}-piperidine-1-carbonyl)-butyl]-amide;
Azepane-1-carboxylic acid (3-methyl-1-{4-[(3-methyl-butyl)-(4-phenylethynyl-phenyl)-amino]-piperidine-1-carbonyl}-butyl)-amide;
Azepane-1-carboxylic acid (1-{4-[[4-(2-cyclohexyl-ethyl)-phenyl]-(3-methyl-butyl)-amino]-piperidine-1-carbonyl}-3-methyl-butyl)-amide;
Azepane-1-carboxylic acid (1-{4-[{4-[2-(1-hydroxy-cyclohexyl)-ethyl]-phenyl}-(3-methyl-butyl)-amino]-piperidine-1-carbonyl}-3-methyl-butyl)-amide;
Azepane-1-carboxylic acid (1-{4-[[4-(3,3-dimethyl-butyl)-phenyl]-(3-methyl-butyl)-amino]-piperidine-1-carbonyl}-3-methyl-butyl)-amide;
Azepane-1-carboxylic acid [3-methyl-1-(4-{(3-methyl-butyl)-[4-(2-piperidin-1-yl-ethyl)-phenyl]-amino}-piperidine-1-carbonyl)-butyl]-amide;
Azepane-1-carboxylic acid [3-methyl-1-(4-{(3-methyl-butyl)-[4-(2-piperidin-1-yl-ethyl)-phenyl]-amino}-piperidine-1-carbonyl)-butyl]-amide;
Azepane-1-carboxylic acid (1-{4-[(2-benzyloxy-phenyl)-(3-methyl-butyl)-amino]-piperidine-1-carbonyl}-3-methyl-butyl)-amide;
Azepane-1-carboxylic acid (3-methyl-1-{4-[(3-methyl-butyl)-(4-phenoxy-phenyl)-amino]-piperidine-1-carbonyl}-butyl)-amide;
Azepane-1-carboxylic acid (1-{4-[(4-benzyl-phenyl)-(3-methyl-butyl)-amino]-piperidine-1-carbonyl}-3-methyl-butyl)-amide;
Azepane-1-carboxylic acid [1-(4-{[(4-benzyloxy-phenyl)-(3-methyl-butyl)-amino]-methyl}-piperidine-1-carbonyl)-3-methyl-butyl]-amide;
Azepane-1-carboxylic acid [1-(1,1-dimethyl-2-{(3-methyl-butyl)-[4(pyridin-2-ylmethoxy)-phenyl]-amino}-ethylcarbonyl)-3-methyl-butyl]-amide;
Azepane-1-carboxylic acid [1-(1,1-dimethyl-2-{(3-methyl-butyl)-[4-(pyridin-3-ylmethoxy)-phenyl]-amino}-ethylcarbamoyl)-3-methyl-butyl]-amide;
Azepane-1-carboxylic acid [1-(1,1-dimethyl-2-{(3-methyl-butyl)-[4-(pyridin-4-ylmethoxy)-phenyl]-amino}-ethylcarbamoyl)-3-methyl-butyl]-amide;
Azepane-1-carboxylic acid (1-{1,1-dimethyl-2-[(3-methyl-butyl)-(4-phenethyl-phenyl)-amino]-ethylcarbamoyl}-3-methyl-butyl)-amide;
Azepane-1-carboxylic acid (1-{1,1-dimethyl-2-[(3-methyl-butyl)-(4-phenylethynyl-phenyl)-amino]-ethylcarbamoyl}-3-methyl-butyl)-amide;
Azepane-1-carboxylic acid (1-{2-[[4-(2-cyclohexyl-ethyl)-phenyl]-(3-methyl-butyl)-amino]-1,1-dimethyl-ethylcarbamoyl}-3-methyl-butyl)-amide;
Azepane-1-carboxylic acid (1-{2-[{4-[2-(1-hydroxy-cyclohexyl)-ethyl]-phenyl}-(3-methyl-butyl)-amino]-1,1-dimethyl-ethylcarbamoyl}-3-methyl-butyl)-amide;
Azepane-1-carboxylic acid (1-{2-[[4-(3,3-dimethyl-butyl)-phenyl]-(3-methyl-butyl)-amino]-1,1-dimethyl-ethylcarbamoyl}-3-methyl-butyl)-amide;
Azepane-1-carboxylic acid [1-{1,1-dimethyl-2-{(3-methyl-butyl)-[4-(2-piperidin-1-yl-ethyl)-phenyl]-amino}-ethylcarbamoyl)-3-methyl-butyl]-amide;
Azepane-1-carboxylic acid (1-{2-[(3-benzyloxy-phenyl)-(3-methyl-butyl)-amino]-1,1-dimethyl-ethylcarbamoyl}-3-methyl-butyl)-amide; and
Azepane-1-carboxylic acid (1-{2-[(2-benzyloxy-phenyl)-(3-methyl-butyl)-amino]-1,1-dimethyl-ethylcarbamoyl}-3-methyl-butyl)-amide.

Also provided by the present invention is a pharmaceutical composition comprising a compound of Formula I.

Also provided is a method of blocking calcium channels, the method comprising administering to a patient in need of calcium channel blocking, a therapeutically effective amount of a compound of Formula I to block calcium channels.

In a preferred embodiment of the method of blocking calcium channels, the calcium channels are N-type calcium channels.

Also provided is a method of blocking N-type calcium channels, the method comprising administering to a patient in need of N-type calcium channel blocking a therapeutically effective amount of a compound of Formula I to block N-type calcium channels.

Also provided is a method of treating stroke, the method comprising administering to a patient having a stroke a therapeutically effective amount of a compound of Formula I.

Also provided is a method of preventing a stroke, the method comprising administering to a patient at risk of having a stroke a therapeutically effective amount of a compound of Formula I.

Also provided is a method of treating cerebral ischemia, the method comprising administering to a patient having cerebral ischemia a therapeutically effective amount of a compound of Formula I.

Also provided is a method of treating head trauma, the method comprising administering to a patient having head trauma a therapeutically effective amount of a compound of Formula I.

Also provided is a method of treating epilepsy, the method comprising administering to a patient having epilepsy a therapeutically effective amount of a compound of Formula I.

Also provided is a method of treating pain, the method comprising administering to a patient having pain a therapeutically effective amount of a compound of Formula I.

Also provided is a compound of Formula I wherein $R^5$ is 2-methylpropyl;

Z is

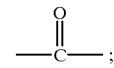

and

X is

Also provided is a compound of Formula I wherein R³ and R⁴ are each independently hydrogen, or

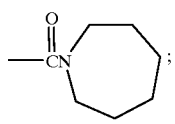

and

R² is —CH₂phenyl, $C_1$–$C_8$ alkenyl, or $C_1$–$C_8$ alkyl.

Also provided is a compound of Formula I wherein

R³ and R⁴ are hydrogen;

R⁵ is 2-methyl propyl;

Z is —CH₂— or

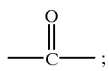

and

X is

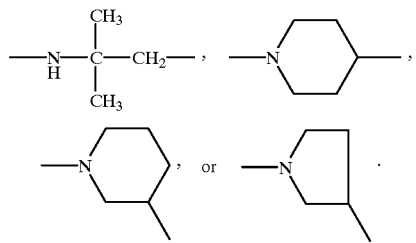

Also provided is a compound of Formula I wherein

R³ and R⁴ are hydrogen;

R⁵ is 2-methyl propyl;

Z is —CH₂— or

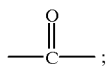

X is

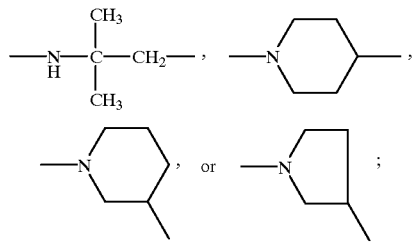

R² is $C_1$–$C_8$ alkyl, or $C_1$–$C_8$ alkenyl;

V is OCH₂—, —(CH₂)$_n$—; and

Q is phenyl, substituted phenyl, $C_3$–$C_8$ cycloalkyl, and $C_1$–$C_6$ alkyl.

Also provided is a compound of Formula I wherein R² is

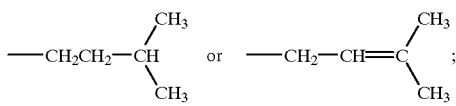

and V—Q is —Obenzyl,

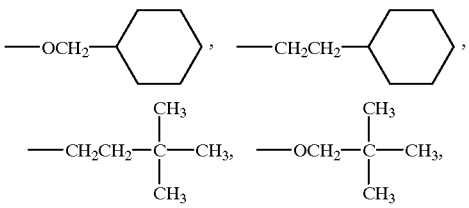

—O—CH₂— substituted phenyl, —CH₂CH₂-phenyl, or —CH₂CH₂-substituted phenyl.

Also provided are the compounds:

(S)-2-Amino-1-{4-[(4-benzyloxy-phenyl)-(3-methyl-but-2-enyl)-amino]-piperidin-1-yl}-4-methyl-pentan-1-one;

(R)-2-Amino-1-{4-[(4-benzyloxy-phenyl)-(3-methyl-but-2-enyl)-amino]-piperidin-1-yl}-4-methyl-pentan-1-one;

(S)-2-Amino-1-{4-[(4-benzyloxy-phenyl)-(3-methyl-but-2-enyl)-amino]-piperidin-1-yl}-3-methyl-pentan-1-one;

(S)-1-{4-[(4-Benzyloxy-phenyl)-(3-methyl-but-2-enyl)-amino]-piperidin-1-yl}-2-dimethylamino-4-methyl-pentan-1-one;

(S)-1-{4-[(4-Benzyloxy-phenyl)-(3-methyl-but-2-enyl)-amino]-piperidin-1-yl}-2-isopropylamino-4-methyl-pentan-1-one;

(S)-1-{4-[(4-Benzyloxy-phenyl)-(3-methyl-but-2-enyl)-amino]-piperidin-1-yl}-4-methyl-2-(3-methyl-butylamino)-pentan-1-one;

(S)-1-{4-[(4-Benzyloxy-phenyl)-(3-methyl-but-2-enyl)-amino]-piperidin-1-yl}-2-cyclohexylamino-4-methyl-pentan-1-one;

(S)-1-{4-[(4-Benzyloxy-phenyl)-(3-methyl-but-2-enyl)-amino]-piperidin-1-yl}-4-methyl-2-[(1H-pyrrol-2-ylmethyl)-amino]-pentan-1-one;

(S)-Azepane-1-carboxylic acid {1-[4-(4-benzyloxy-phenylamino)-piperidine-1-carbonyl]-3-methyl-butyl}-amide;

(S)-Azepane-1-carboxylic acid (1-{4-[(4-benzyloxy-phenyl)-2-methylbutyl-amino]-piperidine-1-carbonyl}-3-methyl-butyl)-amide;

(S)-Azepane-1-carboxylic acid (1-{4-[(4-benzyloxy-phenyl)-ethyl-amino]-piperidine-1-carbonyl}-3-methyl-butyl)-amide;

(S)-Azepane-1-carboxylic acid (1-{4-[benzyl-(4-benzyloxy-phenyl)-amino]-piperidine-1-carbonyl}-3-methyl-butyl)-amide;

Azepane-1-carboxylic acid (1-{4-[(4-benzyloxy-phenyl)-(3-hydroxy-butyl)-amino]-piperidine-1-carbonyl}-3-methyl-butyl)-amide;

(S)-{4-[(1-{2-[(Azepane-1-carbonyl)-amino]-4-methyl-pentanoyl}-piperidin-4-yl)-(3-methyl-but-2-enyl)-amino]-phenyl}-carbamic acid benzyl ester;

(S)-{4-[(1-{2-[(Azepane-1-carbonyl)-amino]-4-methyl-pentanoyl}-piperidin-4yl)-(3-methyl-butyl)-amino]-phenyl}-carbamic acid benzyl ester;

(S)-Azepane-1-carboxylic acid (1-{4-[(4-amino-phenyl)-(3-methyl-butyl)-amino]-piperidine-1-carbonyl}-3-methyl-butyl)-amide;

(S)-Azepane-1-carboxylic acid (1-{4-[[4-(3,3-dimethyl-butylamino)-phenyl]-(3-methyl-butyl)-amino]-piperidine-1-carbonyl}-3-methyl-butyl)-amide;
(S)-Azepane-1-carboxylic acid (1-{4-[[4-(cyclohexylmethyl-amino)-phenyl]-(3-methyl-butyl)-amino]-piperidine-1-carbonyl}-3-methyl-butyl)-amide;
(S)-Azepane-1-carboxylic acid (1-{4-[[4-(3-hydroxy-butylamino)-phenyl]-(3-methyl-butyl)-amino]-piperidine-1-carbonyl}-3-methyl-butyl)-amide;
(S)-Azepane-1-carboxylic acid (1-{4-[(4-benzylamino-phenyl)-(3-methyl-butyl)-amino]-piperidine-1-carbonyl}-3-methyl-butyl)-amide;
(S)-Azepane-1-carboxylic acid {3-methyl-1-[4-((3-methyl-butyl)-{4-[(pyridin-2-ylmethyl)-amino]-phenyl}-amino)-piperidine-1-carbonyl]-butyl}-amide;
(S)-Azepane-1-carboxylic acid (1-{4-[[4-(4-dimethylamino-benzylamino)-phenyl]-(3-methyl-butyl)-amino]-piperidine-1-carbonyl}-3-methyl-butyl)-amide;
(S)-Azepane-1-carboxylic acid (1-{4-[[4-(4-hydroxy-benzylamino)-phenyl]-(3-methyl-butyl)-amino]-piperidine-1-carbonyl}-3-methyl-butyl)-amide;
(S)-Azepane-1-carboxylic acid (1-{4-[[4-(1-hydroxy-cyclohexylethynyl)-phenyl]-(3-methyl-but-2-enyl)-amino]-piperidine-1-carbonyl}-3-methyl-butyl)-amide;
(S)-2-Amino-1-{4-[(4-benzyloxy-phenyl)-(3-methyl-butyl)-amino]-piperidin-1-yl}-4-methyl-pentan-1-one;
(S,R/S)-2-Amino-1-{3-[(4-benzyloxy-phenyl)-(3-methyl-but-2-enyl)-amino]-piperidin-1-yl}4-methyl-pentan-1-one;
(S,R/S)-Azepane-1-carboxylic acid (1-{3-[(4-benzyloxy-phenyl)-(3-methyl-but-2-enyl)-amino]-piperidine-1-carbonyl}-3-methyl-butyl)-amide;
(S)-[1-(2-Amino-4-methyl-pentyl)-piperidin-4-yl]-(4-benzyloxy-phenyl)-(3-methyl-but-2-enyl)-amine;
(S)-2-Amino-1-{4-[(4-(4-fluorobenzyloxy)-phenyl)-(3-methyl-butyl)-amino]-piperidin-1-yl}-4-methyl-pentan-1-one;
(S)-[1-(2-Amino-4-methyl-pentyl)-piperidin-4-yl]-[4(4-fluorobenzyloxy)-phenyl]-(3-methyl-butyl)-amine;
(S)-2-Amino-1-{4-[(4-phenethyl-phenyl)-(3-methyl-but-2-enyl)-amino]-piperidin-1-yl}-4-methyl-pentan-1-one; and
(S)-Azepane-1-carboxylic acid (1-{4-[(4-phenethyl-phenyl)-(3-methyl-but-2-enyl)-amino]-piperidine-1-carbonyl}-3-methyl-butyl)-amide.

Also provided are the compounds:
(S)-N$^1$-{2-[(4-benzyloxy-phenyl)-(3-methyl-butyl)-amino]-1,1-dimethyl-ethyl}-4-methyl-pentane-1,2-diamine;
(S)-2-Amino-4-methyl-pentanoic acid {2-[(4-benzyloxy-phenyl)-(3-methyl-butyl)-amino]-1,1-dimethyl-ethyl}-amide;
(S)-N$^1$-{2-[(4-Cyclohexylmethoxy-phenyl)-(3-methyl-butyl)-amino]-1,1-dimethyl-ethyl}-4-methyl-pentane-1,2-diamine;
(S)-2-Amino-4-methyl-pentanoic acid {2-[(4-cyclohexylmethoxy-phenyl)-(3-methyl-butyl)-amino]-1,1-dimethyl-ethyl}-amide;
(S)-N$^1$-{2-[[4-(2-Cyclohexyl-ethyl)-phenyl]-(3-methyl-butyl)-amino]-1,1-dimethyl-ethyl}-4-methyl-pentane-1,2-diamine;
(S)-2-Amino-4-methyl-pentanoic acid {2-[[4-(2-cyclohexyl-ethyl)-phenyl]-(3-methyl-butyl)-amino]-1,1-dimethyl-ethyl}-amide;
(S)-N$^1$-{2-[[4-(3,3-Dimethyl-butyl)-phenyl]-(3-methyl-butyl)-amino]-1,1-dimethyl-ethyl}-4-methyl-pentane-1,2-diamine;
(S)-$^2$-Amino-4-methyl-pentanoic acid {2-[4-(3,3-dimethyl-butyl)-phenyl]-(3-methyl-butyl)-amino]-1,1-dimethyl-ethyl}-amide;
(S)-N$^1$-{2-[[4-(2,2-Dimethyl-propoxy)-phenyl]-(3-methyl-butyl)-amino]-1,1-dimethyl-ethyl}-4-methyl-pentane-1,2-diamine;
(S)-2-Amino-4-methyl-pentanoic acid {2-[[4-(2,2-dimethyl-propoxy)-phenyl]-(3-methyl-butyl)-amino]-1,1-dimethyl-ethyl}-amide;
(S)-N$^1$-{2-[(4-benzyloxy-phenyl)-(3-methyl-but-2-enyl)-amino]-1,1-dimethyl-ethyl}-4-methyl-pentane-1,2-diamine;
(S)-2-Amino-4-methyl-pentanoic acid {2-[(4-benzyloxy-phenyl)-(3-methyl-but-2-enyl)-amino]-1,1-dimethyl-ethyl}-amide;
(S)-N$^1$-{2-[(4-Cyclohexylmethoxy-phenyl)-(3-methyl-but-2-enyl)-amino]-1,1-dimethyl-ethyl}-4-methyl-pentane-1,2-diamine;
(S)-2-Amino-4-methyl-pentanoic acid {2-[(4-cyclohexylmethoxy-phenyl)-(3-methyl-but-2-enyl)-amino]-1,1-dimethyl-ethyl}-amide;
(S)-N$^1$-{2-[[4-(2-Cyclohexyl-ethyl)-phenyl]-(3-methyl-but-2-enyl)-amino]-1,1-dimethyl-ethyl}-4-methyl-pentane-1,2-diamine;
(S)-2-Amino-4-methyl-pentanoic acid {2-[[4-(2-cyclohexyl-ethyl)-phenyl]-(3-methyl-but-2-enyl)-amino]-1,1-dimethyl-ethyl}-amide;
(S)-N$^1$-{2-[[4-(3,3-Dimethyl-butyl)-phenyl]-(3-methyl-but-2-enyl)-amino]-1,1-dimethyl-ethyl}-4-methyl-pentane-1,2-diamine;
(S)-2-Amino-4-methyl-pentanoic acid {2-[[4-(3,3-dimethyl-butyl)-phenyl]-(3-methyl-but-2-enyl)-amino]-1,1-dimethyl-ethyl}-amide;
(S)-N$^1$-{2-[[4-(2,2-Dimethyl-propoxy)-phenyl]-(3-methyl-but-2-enyl)-amino]-1,1-dimethyl-ethyl}-4-methyl-pentane-1,2-diamine;
(S)-2-Amino-4-methyl-pentanoic acid {2-[[4-(2,2-dimethyl-propoxy)-phenyl]-(3-methyl-but-2-enyl)-amino]-1,1-dimethyl-ethyl}-amide;
(S)-N$^1$-{2-[[4-(4-Chloro-benzyloxy)-phenyl]-(3-methyl-butyl)-amino]-1,1-dimethyl-ethyl}-methyl-pentane-1,2-diamine;
(S)-2-Amino-4-methyl-pentanoic acid {2-[[4-(4-chloro-benzyloxy)-phenyl]-(3-methyl-butyl)-amino]-1,1-dimethyl-ethyl}-amide;
(S)-N$^1$-{2-[[4-(4Fluoro-benzyloxy)-phenyl]-(3-methyl-butyl)-amino]-1,1-dimethyl-ethyl}-4-methyl-pentane-1,2-diamine;
(S)-2-Amino-4-methyl-pentanoic acid {2-[[4-(4-fluoro-benzyloxy)-phenyl]-(3-methyl-butyl)-amino]-1,1-dimethyl-ethyl)}-amide;
(S)N$^1$-{1,1-Dimethyl-2-[(3-methyl-butyl)-(4-phenethyl-phenyl)-amino]-ethyl}-4-methyl-pentane-1,2-diamine;
(S)-2-Amino-4-methyl-pentanoic acid {1,1-dimethyl-2-[(3-methyl-butyl)-(4-phenethyl-phenyl)-amino]-ethyl}-amide;
(S)-2-Amino-4-methyl-pentanoic acid {2-[{4-[2-(4-chloro-phenyl)-ethyl]-phenyl}-(3-methyl-butyl)-amino]-1,1-dimethyl-ethyl}-amide;
(S)-2-Amino-4-methyl-pentanoic acid {2-[{4-[2-(4-chloro-phenyl)-ethyl]-phenyl}-(3-methyl-butyl)-amino]-1,1-dimethyl-ethyl}-amide;
(S)-N$^1$-{2-[[4-(4-Chloro-benzyloxy)-phenyl]-(3-methyl-but-2-enyl)-amino]-1,1-dimethyl-ethyl}-4-methyl-pentane-1,2-diamine;
(S)-2-Amino-4-methyl-pentanoic acid {2-[[4-(4-chloro-benzyloxy)-phenyl]-(3-methyl-but-2-enyl)-amino]-1,1-dimethyl-ethyl}-amide;
(S)-N$^1$-{2-[[4-(4-Fluoro-benzyloxy)-phenyl]-(3-methyl-but-2-enyl)-amino]-1,1-dimethyl-ethyl}-4-methyl-pentane-1,2-diamine;

(S)-N¹-{1,1-Dimethyl-2-[(3-methyl-but-2-enyl)-(4-phenethyl-phenyl)-amino]-ethyl}-4-methyl-pentane-1,2-diamine;

(S)-2-Amino-4-methyl-pentanoic acid {2-[[4-(4-fluoro-benzyloxy)-phenyl]-(3-methyl-but-2-enyl)-amino]-1,1-dimethyl-ethyl}-amide;

(S)-2-Amino-4-methyl-pentanoic acid {1,1-dimethyl-2-[(3-methyl-but-2-enyl)-(4-phenethyl-phenyl)-amino]-3-ethyl}-amide;

(S)-2-Amino-4-methyl-pentanoic acid {2-[{4-[2-(4-chloro-phenyl)-ethyl]-phenyl}-(3-methyl-but-2-enyl)-amino]-1,1-dimethyl-ethyl}-amide;

(S)-2-Amino-4-methyl-pentanoic acid {2-[{4-[2-(4-chloro-phenyl)-ethyl]-phenyl}-(3-methyl-but-2-enyl)-amino]-1,1-dimethyl-ethyl}-amide;

(S)-[1-(2-Amino-4-methyl-pentyl)-piperidinyl]-(4-benzyloxy-phenyl)-(3-methyl-butyl)-amine;

(S)-[1-(2-Amino-4-methyl-pentyl)-piperidin-4-yl]-(4-cyclohexylmethoxy-phenyl)-(3-methyl-butyl)-amine;

(S)-2-Amino-1-{4-4-[(4-cyclohexylmethoxy-phenyl)-(3-methyl-butyl)-amino]-piperidin-1-yl}-4-methyl-pentan-1-one;

(S)-[1-(2-Amino-4-methyl-pentyl)-piperidin-4-yl]-[4-(2-cyclohexyl-ethyl)-phenyl]-(3-methyl-butyl)-amine;

(S)-2-Amino-1-{4-[[4-(2-cyclohexyl-ethyl)-phenyl]-(3-methyl-butyl)-amino]-piperidin-1-yl}-4-methyl-pentan-1-one;

(S)-[1-(2-Amino-4-methyl-pentyl)-piperidin-4-yl]-[4-(2,2-dimethyl-propoxy)-phenyl]-(3-methyl-butyl)-amine;

(S)-2-Amino-1-{4-[[4-(2,2-dimethyl-propoxy)-phenyl]-(3-methyl-butyl)-amino]-piperidin-1-yl}-4-methyl-pentan-1-one;

(S)-[1-(2-Amino-4-methyl-pentyl)-piperidin-4-yl]-[4-(3,3-dimethyl-butyl)-phenyl]-(3-methyl-butyl)-amine;

(S)-2-Amino-1-{4-[[4-3,3-dimethyl-butyl)-phenyl]-(3-methyl-butyl)-amino]-piperidin-1-yl}-4-methyl-pentan-1-one;

(S)-[1-(2-Amino-4-methyl-pentyl)-piperidin-4-yl]-(4-benzyloxy-phenyl)-(3-methyl-but-2-enyl)-amine;

(S)[1-(2-Amino-4-methyl-pentyl)-piperidin-4-yl]-(4-cyclohexylmethoxy-phenyl)-(3-methyl-but-2-enyl)-amine;

(S)-2-Amino-1-{4-[(4-cyclohexylmethoxy-phenyl)-(3-methyl-but-2-enyl)-amino]-piperidin-1-yl}-4-methyl-pentan-1-one;

(S)-[1-(2-Amino-4-methyl-pentyl)-piperidin-4-yl]-[4-(2-cyclohexyl-ethyl)-phenyl]-(3-methyl-but-2-enyl)-amine;

(S)-2-Amino-1-{4-[[4-(2-cyclohexyl-ethyl)-phenyl]-(3-methyl-but-2-enyl)-amino]-piperidin-1-yl}-4-methyl-pentan-1-one;

(S)-[1-(2-Amino-4-methyl-pentyl)-piperidin-4-yl]-[4-(2,2-dimethyl-propoxy)-phenyl]-(3-methyl-but-2-enyl)-amine;

(S)-2-Amino-1-{4-[[4-(2,2-dimethyl-propoxy)-phenyl]-(3-methyl-but-2-enyl)-amino]-piperidin-1-yl }-4-methyl-pentan-1-one;

(S)-[1(2-Amino-4-methyl-pentyl)-piperidin-4-yl]-[4-(3,3-dimethyl-butyl)-phenyl]-(3-methyl-but-2-enyl)-amine;

(S)-2-Amino-1-{4-[[4-(3,3-dimethyl-butyl)-phenyl]-(3-methyl-but-2-enyl)-amino]-piperidin-1-yl}4-methyl-pentan-1-one;

(S)-[1-(2-Amino-4-methyl-pentyl)-piperidin-4-yl]-[4-(4-chloro-benzyloxy)-phenyl]-3-methyl-but-2enyl]-amine;

(S)-2-Amino-1-{4-[[4-(4-chloro-benzyloxy)-phenyl]-(3-methyl-but-2-enyl)-amino]-piperidin-1-yl}-4-methyl-pentan-1-one;

(S)-[1-(2-Amino-4-methyl-pentyl)-piperidin-4-yl]-{4-[2-(4-fluoro-phenyl)-ethyl]-phenyl}-(3-methyl-but-2-enyl)-amine;

(S)-2-Amino-1-{4-[{4-[2-(4-fluoro-phenyl)-ethyl]-phenyl}-(3-methyl-but-2-enyl)-amino]-piperidin-1-yl}-4-methyl-pentan-1-one;

(S)-[1-(2-Amino-4-methyl-pentyl)-piperidin-4-yl]-(3-methyl-but-2-enyl)-(4-phenethyl-phenyl)-amine;

(S)-[1-(2-Amino-4-methyl-pentyl)-piperidin-4-yl]-{4-[2-(4-chloro-phenyl)-ethyl]-phenyl}-(3-methyl-but-2-enyl)-amine;

(S)-2-Amino-1-{4-[{4-[2-(4-chloro-phenyl)-ethyl]-phenyl}-(3-methyl-but-2-enyl)-amino]-piperidin-1-yl)}4-methyl-pentan-1-one;

(S)-[1-(2-Amino-4-methyl-pentyl)-piperidin-4-yl]-[4-(4-chloro-benzyloxy)-phenyl]-(3-methyl-but-2-enyl)-amine;

(S)-2-Amino-1-{4-[[4-(4-chloro-benzyloxy)-phenyl]-(3-methyl-but-2-enyl)-amino]-piperidin-1-yl}-4-methyl-pentan-1-one;

(S)-[1-(2-Amino-4-methyl-pentyl)-piperidin-4-yl]-{4-[2-(4-fluoro-phenyl)-ethyl]-phenyl}-(3-methyl-butyl)-amine;

(S)-2-Amino-1-{4-[{4-[2-(4-fluoro-phenyl)-ethyl]-phenyl}-(3-methyl-butyl)-amino]-piperidin-1-yl}-4-methyl-pentan-1-one;

(S)-[1-(2-Amino-4-methyl-pentyl)-piperidin-4-yl]-(3-methyl-butyl)-(4-phenethyl-phenyl)-amine;

(S)-2-Amino-4-methyl-1-{4-[(3-methyl-butyl)-(4-phenethyl-phenyl)-amino]-piperidin-1-yl}-pentan-1-one;

(S)-[1-(2-Amino-4-methyl-pentyl)-piperidin-4-yl]-{4-[2-(4-chloro-phenyl)-ethyl]-phenyl}-(3-methyl-butyl)-amine;

(S)-2-Amino-1-{4-[{4-[2-4-chloro-phenyl)-ethyl]-phenyl}-(3-methyl-butyl)-amino]-piperidin-1-yl}-4-methyl-pentan-1-one;

(S)-[1-(2-Amino-4-methyl-pentyl)-piperidin-3-yl]-(4-benzyloxy-phenyl)-(3-methyl-butyl)-amine;

(S)-2-Amino-1-{3-[(4-benzyloxy-phenyl)-(3-methyl-butyl)-amino]-piperidin-1-yl}-4-methyl-pentan-1-one;

(S)-[1-(2-Amino-4-methyl-pentyl)-piperidin-3-yl]-(4-cyclohexylmethoxy-phenyl)-(3-methyl-butyl)-amine;

(S)-2-Amino-1-{3-[(4-cyclohexylmethoxy-phenyl)-(3-methyl-butyl)-amino]-piperidin-1-yl}-4-methyl-pentan-1-one;

(S)-[1-(2-Amino-4-methyl-pentyl)-piperidin-3-yl]-[4-(2-cyclohexyl-ethyl)-phenyl]-(3-methyl-butyl)-amine;

(S)-2-Amino-1-{3-[[4-(2-cyclohexyl-ethyl)-phenyl]-(3-methyl-butyl)-amino]-piperidin-1-yl}-4-methyl-pentan-1-one;

(S)-[1-2-Amino-4-methyl-pentyl)-piperidin-3-yl]-[4-(2,2-dimethyl-propoxy)-phenyl]-(3-methyl-butyl)-amine;

(S)-2-Amino-1-{3-[[4-(2,2-dimethyl-propoxy)-phenyl]-(3-methyl-butyl)-amino]-piperidin-1-yl}-4-methyl-pentan-1-one;

(S)-[1-2-Amino-4-methyl-pentyl)-piperidin-3-yl]-[4-(3,3 dimethyl-butyl)-phenyl]-(3-methyl-butyl)-amine;

(S)-2-Amino-1-{3-[[4-(3,3-dimethyl-butyl)-phenyl]-(3-methyl-butyl)-amino]-piperidin-1-yl }-4-methyl-pentan-1-one;

(S)-2-Amino-1-{3-[(4-benzyloxy-phenyl)-(3-methyl-but-2-enyl)-amino]-piperidin-1-yl}-4-methyl-pentan-1-one;

(S)-[1-(2-Amino-4-methyl-pentyl)-piperidin-3-yl]-(4-cyclohexylmethoxy-phenyl)-(3-methyl-but-2-enyl)-amine;

(S)-2-Amino-1-{3-[(4-cyclohexylmethoxy-phenyl)-(3-methyl-but-2-enyl)-amino]-piperidin-1}-4-methyl-pentan-1-one;

(S)-[1-(2-Amino-4-methyl-pentyl)-piperidin-3-yl]-[4-(2-cyclohexyl-ethyl)-phenyl]-(3-methyl-but-2-enyl)-amine;

(S)-2-Amino-1-{3-[[4-(2-cyclohexyl-ethyl)-phenyl]-(3-methyl-but-2-enyl)-amino]-piperidin-1-yl}-4-methyl-pentan-1-one;

(S)-[1-(2-Amino-4-methyl-pentyl)-piperidin-3-yl]-[4-(2,2-dimethyl-propoxy)-phenyl]-(3-methyl-but-2-enyl)-amine;
(S)-2-Amino-1-{3-[[-4-(2,2-dimethyl-propoxy)-phenyl]-(3-methyl-but-2-enyl)-amino]-piperidin-1-yl}-4-methyl-pentan-1-one;
(S)-2-Amino-1-}3-[[4-(3,3-dimethyl-butyl)-phenyl]-(3-methyl-but-2enyl)-amino]-piperidin-1-yl}-4-methyl-pentan-1-one;
(S)-[1-{2-Amino-4-methyl-pentyl)-piperidin-3-yl]-[4-(3,3-dimethyl-butyl)-phenyl]-(3-methyl-but-2-enyl)-amine;
(S)-[1-Amino-4-methyl-pentyl)-piperidin-3-yl]-[4-(4-chloro-benzyloxy)-phenyl]-(3-methyl-but-2-enyl)-amine;
(S)-2-Amino-1-{3-[[4-(4-chloro-benzyloxy)-phenyl]-(3-methyl-but-2-enyl)-amino]-piperidin-1-yl}-4-methyl-pentan-1-one;
(S)-[1-(2-Amino-4-methyl-pentyl)-piperidin-3-yl]-(4-[2-(4-fluoro-phenyl)-ethyl]-phenyl}-(3-methyl-but-2-enyl)-amine;
(S)-2-Amino-1-{3-[{4-[2-(4-fluoro-phenyl)-ethyl]-phenyl}-(3-methyl-but-2-enyl)-amino]-piperidin-1-yl}-4-methyl-pentan-1-one;
(S)-[1-(2-Amino-4-methyl-pentyl)-piperidin-3-yl]-(3-methyl-but-2-enyl)-(4-phenethyl-phenyl)-amine;
(S)-2-Amino-4-methyl-1-{3-[(3-methyl-but-2-enyl)-(4-phenethyl-phenyl)-amino]-piperidin-1-yl}-pentan-1-one;
(S)-[1-(2-Amino-4-ethyl-pentyl)-piperidin-3-yl]-{4-[2-(4-chloro-phenyl)-ethyl]-phenyl}-(3-methyl-but-2-enyl)-amino;
(S)-2-Amino-1-{3-[{4-[2-(4-chloro-phenyl)-ethyl]-phenyl}-(3-methyl-but-2-enyl)-amino]-piperidin-1-yl}-4-methyl-pentan-1-one;
(S)-[1-(2-Amino-4-methyl-pentyl)-piperidin-3-yl]-[4-(4chloro-benzyloxy)-phenyl]-(3-methyl-butyl)-amine;
(S)-2-Amino-1-{3-[[4-(4-chloro-benzyloxy)-phenyl]-(3-methyl-butyl)-amino]-piperidin-1-yl}-4-methyl-pentan-1-one;
(S)-[1-(2-Amino-4-methyl-pentyl)-piperidin-3-yl]-{4-[2-(4-fluoro-phenyl)-ethyl]-phenyl}-(3-methyl-butyl)-amine;
(S)-2-Amino-1-{3-[{4-[2-(4-fluoro-phenyl)-ethyl]-phenyl}-(3-methyl-butyl)-amino]-piperidin-1-yl)}-4-methyl-pentan-1-one;
(S)-[1-(2-Amino-4-methyl-pentyl)-piperidin-3-yl]-(3-methyl-butyl)-(4-phenethyl-phenyl)-amine;
(S)-2-Amino-4-methyl-1-{3-[(3-methyl-butyl)-(4-phenethyl-phenyl)-amino]-piperidin-1-yl}-pentan-1-one;
(S)-[1-(2-Amino-4-methyl-pentyl)-piperidin-3-yl]-{4-[2-(4-chloro-phenyl)-ethyl]-phenyl}-(3-methyl-butyl)-amine;
(S)-2-Amino-1-{3-[{4-[2-(4-chloro-phenyl)-ethyl]-phenyl}-(3-methyl-butyl)-amino]-piperidin-1-yl}-4-methyl-pentan-1-one;
(S)-[1-(2-Amino-4-methyl-pentyl)-pyrrolidin-3-yl]-(4-benzyloxy-phenyl)-(3-methyl-butyl)-amine;
(S)-2-Amino-1-[3-(4-benzyloxy-phenyl)-(3-methyl-butyl)-amino]-pyrrolidin-1-yl}-4-methyl-pentan-1-one;
(S)-[1-(2-Amino-4-methyl-pentyl)-pyrrolidin-3-yl]-(4-cyclohexylmethoxy-phenyl)-(3-methyl-butyl)-amine;
(S)-2-Amino-1-{3-[(4-cyclohexylmethoxy-phenyl)-(3-methyl-butyl)-amino]-pyrrolidin-1-yl}-4-methyl-pentan-1-one;
(S)-[1-(2-Amino-4-methyl-pentyl)-pyrrolidin-3-yl]-[4-(2-cyclohexyl-ethyl)-phenyl]-(3-methyl-butyl)-amine;
(S)-2-Amino-1-{3-[[4-(2-cyclohexyl-ethyl)-phenyl]-(3-methyl-butyl)-amino]-pyrrolidin-1-yl}-4-methyl-pentan-1-one;
(S)-[1-(2-Amino-4-methyl-pentyl)-pyrrolidin-3-yl]-[4-(2,2-dimethyl-propoxy)-phenyl]-(3-methyl-butyl)-amine;
(S)-2-Amino-1-{3-[[4-(2,2-dimethyl-propoxy)-phenyl]-(3-methyl-butyl)-amino]-pyrrolidin-1-yl}-4-methyl-pentan-1-one;
(S)-[1-(2-Amino-4-methyl-pentyl)-pyrrolidin-3-yl]-[4-(3,3-dimethyl-butyl)-phenyl]-(3-methyl-butyl)-amine;
(S)-2-Amino-1-{3-[[4-(3,3-dimethyl-butyl)-phenyl]-(3-methyl-butyl)-amino]-pyrrolidin-1-yl}-methyl-pentan-1-one;
(S)-[1-(2-Amino-4-methyl-pentyl)-pyrrolidin-3-yl]-(4-benzyloxy-phenyl)-(3-methyl-but-2-enyl)-amine;
(S)-2-Amino-1-[3-(4-benzyloxy-phenyl)-(3-methyl-but-2-enyl)-amino]-pyrrolidin-1-yl}-4-methyl-pentan-1-one;
(S)-[1-(2-Amino-4-methyl-pentyl)-pyrrolidin-3-yl]-(4-cyclohexylmethoxy-phenyl)-(3-methyl-but-2-enyl)-amine;
(S)-2-Amino-1-{3-[(4-cyclohexylmethoxy-phenyl)-(3-methyl-but-2-enyl)-amino]-pyrrolidin-1-yl}-4-methyl-pentan-1-one;
(S)-[1-(2-Amino-4-methyl-pentyl)-pyrrolidin-3-yl]-[4-(2-cyclohexyl-ethyl)-phenyl]-(3-methyl-but-2-enyl)-amine;
(S)-2-Amino-1-{3-[[4-(2-cyclohexyl-ethyl)-phenyl]-(3-methyl-but-2-enyl)-amino]-pyrrolidin-1-yl}-4-methyl-pentan-1-one;
(S)-[1-(2-Amino-4-methyl-pentyl)-pyrrolidin-3-yl]-[4-(2,2-dimethyl-propoxy)-phenyl]-(3-methyl-but-2-enyl)-amine;
(S)-2-Amino-1-{3-[[4-(2,2-dimethyl-propoxy)-phenyl]-(3-methyl-but-2-enyl)-amino]-pyrrolidin-1-yl}-4-methyl-pentan-1-one;
(S)-[1-{2-Amino-4-methyl-pentyl)-pyrrolidin-3-yl]-[4-(3,3-dimethyl-butyl)-phenyl]-(3-methyl-but-2-enyl)-amine;
(S)-2-Amino-1-{3-[[4-(3,3-dimethyl-butyl)-phenyl]-(3-methyl-but-2-enyl)-amino]-pyrrolidin-1-yl}-4-methyl-pentan-1-one;
(S)-[1-(2-Amino-4-methyl-pentyl)-pyrrolidin-3-yl]-[4-(4-chloro-benzyloxy)-phenyl]-(3-methyl-but-2-enyl)-amine;
(S)-2-Amino-1-{3-[[4-(4-chloro-benzyloxy)-phenyl]-(3-methyl-but-2-enyl)-amino]-pyrrolidin-1-yl}-4-methyl-pentan-1-one;
(S)-[1-{2-Amino-4-methyl-pentyl)-pyrrolidin-3-yl]-{4-[2-(4-fluoro-phenyl)-ethyl]-phenyl}-(3-methyl-but-2-enyl)-amine;
(S)-2-Amino-1-{3-1-{4-[2-4fluoro-phenyl)-ethyl]-phenyl}-(3-methyl-but-2-enyl)-amino]-pyrrolidin-1-yl}-4-methyl-pentan-1-one;
(S)-[1-(2-Amino-4-methyl-pentyl)-pyrrolidin-3-yl]-(3-methyl-but-2-enyl)-(4-phenethyl-phenyl)-amine;
(S)-2-Amino-4-methyl-1-{3-[(3-methyl-but-2-enyl)-(4-phenethyl-phenyl)-amino]-pyrrolidin-1-yl}-pentan-1-one;
(S)-[1-(2-Amino-4-methyl-pentyl)-pyrrolidin-3-yl]-{4-[2-(4-chloro-phenyl)-ethyl]-phenyl}-(3-methyl-but-2-enyl)-amine;
(S)-2-Amino-1-{3-[{4-[2-(4-chloro-phenyl)-ethyl]-phenyl}-(3-methyl-but-2-enyl)-amino]-pyrrolidin-1-yl)}-4-methyl-pentan-1-one;
(S)-[1-(2-Amino-4-methyl-pentyl)-pyrrolidin-3-yl-[4-(4-chloro-benzyloxy)-phenyl]-(3-methyl-butyl)-amine;
(S)-2-Amino-1-{3-[[4-(4-chloro-benzyloxy)-phenyl]-(3-methyl-butyl)-amino]-pyrrolidin-1-yl}-4-methyl-pentan-1-one;
(S)-[1-(2-Amino-4-methyl-pentyl)-pyrrolidin-3-yl]-{4-[2-(4-fluoro-phenyl)-ethyl]phenyl}-(3-methyl-butyl)-amine;
(S)-2-Amino-1-{3-[{4-[2-(4-fluoro-phenyl)-ethyl]-phenyl}-(3-methyl-butyl)-amino]-pyrrolidin-1-yl}-4-methyl-pentan-1-one;
(S)-[1-(2-Amino-4-methyl-pentyl)-pyrrolidin-3-yl]-(3-methyl-butyl)-(4-phenethyl-phenyl)-amine;

(S)-2-Amino-4-methyl-1-{3-[(3-methyl-butyl)-(4-phenethyl-phenyl)-amino]-pyrrolidin-1-yl}-pentan-1-one;

(S)-[1-(2-Amino-4-methyl-pentyl)-pyrrolidin-3-yl]-{4-[2-(4-chloro-phenyl)-ethyl]-phenyl}-(3-methyl-butyl)-amine;

(S)-2-Amino-1-{3-[{4-[2-(4-chloro-phenyl)-ethyl]-phenyl}-(3-methyl-butyl)-amino]-pyrrolidin-1-yl}-4-methyl-pentan-1-one;

(S)-Benzoic acid 4-[[1-{2-amino-4-methyl-pentyl)-piperidin-3-yl]-(3-methyl-but-2-enyl)-amino]-phenyl ester;

(R)-[1-(2-Amino-4-methyl-pentyl)-piperidin-4-yl]-(4-benzyloxy-phenyl)-(3-methyl-butyl)-amine;

(R)-2-Amino-1-{4-[(4-benzyloxy-phenyl)-(3-methyl-butyl)-amino]-piperidin-1-yl}-4-methyl-pentan-1-one;

(R)-[1-(2-Amino-4-methyl-pentyl)-piperidin-4-yl]-(4-cyclohexylmethoxy-phenyl)-(3-methyl-butyl)-amine;

(R)-2-Amino-1-{4-[(4-cyclohexylmethoxy-phenyl)-(3-methyl-butyl)-amino]-piperidin-1-yl}-4-methyl-pentan-1-one;

(R)-[1-(2-Amino-4-methyl-pentyl)-piperidin-4-yl]-[4-(2-cyclohexyl-ethyl)-phenyl]-(3-methyl-butyl)-amine;

(R)-2-Amino-1-{4-[[4-(2-cyclohexyl-ethyl)-phenyl]-(3-methyl-butyl)-amino]-piperidin-1-yl}-4-methyl-pentan-1-one;

(R)-[1-(2-Amino-methyl-pentyl)-piperidin-4-yl]-[4-(2,2-dimethyl-propoxy)-phenyl]-(3-methyl-butyl)-amine;

(R)-2-Amino-1-{4-[[4-(2,2-dimethyl-propoxy)-phenyl]-(3-methyl-butyl)-amino]-piperidin-1-yl}-methyl-pentan-1-one;

(R)-[1-(2-Amino-4-methyl-pentyl)-piperidin-4-yl]-[4-(3,3-dimethyl-butyl)-phenyl]-(3-methyl-butyl)-amine;

(R)-2-Amino-1-{4-[[4-(3,3dimethyl-butyl)-phenyl]-(3-methyl-butyl)-amino]-piperidin-1-yl}-4-methyl-pentan-1-one;

(R)-[1-(2-Amino-4-methyl-pentyl)-piperidin-4-yl]-(4-benzyloxy-phenyl)-(3-methyl-but-2-enyl)-amine;

(R)-[1-(2-Amino-4-methyl-pentyl)-piperidin-4-yl]-[4-(2-cyclohexyl-ethyl)-phenyl]-(3-methyl-but-2-enyl)-amine;

(R)-2-Amino-1-{4-[[4-(2-cyclohexyl-ethyl)-phenyl]-(3-methyl-but-2-enyl)-amino]-piperidin-1-yl}-4-methyl-pentan-1-one;

(R)-[1-(2-Amino-4-methyl-pentyl)-piperidin-4-yl]-[4-(3,3-dimethyl-butyl)-phenyl]-(3-methyl-but-2-enyl)-amine;

(R)-2-Amino-1-{4-[[4-(3,3-dimethyl-butyl)-phenyl]-(3-methyl-but-2-enyl)-amino]-piperidin-1-yl}-4-methyl-pentan-1-one;

(R)-[1-(2-Amino-4-methyl-pentyl)-piperidin-4-yl]-[4-(4-chloro-benzyloxy)-phenyl]-(3-methyl-butyl)-amine;

(R)-2-Amino-1-4-[[4-(4-chloro-benzyloxy)-phenyl]-(3-methyl-butyl)-amino]-piperidin-1-yl}-4-methyl-pentan-1-one;

(R)-[1-(2-Amino-4-methyl-pentyl)-piperidin-4-yl]-{4-[2-(4-fluoro-phenyl)-ethyl]-phenyl}-(3-methyl-butyl)-amine, (R)-2-Amino-1-{4-[{4-[2-(4-fluoro-phenyl)-ethyl]-phenyl}-(3-methyl-but-2-enyl)-amino]-piperidin-1-yl}-4-methyl-pentan-1-one;

(R)-[1-(2-Amino-4-methyl-pentyl)-piperidin-4-yl]-(3-methyl-but-2-enyl)-(4-phenethyl-phenyl)-amine;

(R)-2-Amino-4-ethyl-1-{4-[(3-methyl-but-2-enyl)-(4-phenethyl-phenyl)-amino]-piperidin-1-yl}-pentan-1-one;

(R)-[1-(2-Amino-4-methyl-pentyl)-piperidin-4-yl]-{4-[2-(4-chloro-phenyl)-ethyl]-phenyl}-(3-methyl-but-2-enyl)-amine;

(R)-2-Amino-1-{4-[{4-[2-(4-chloro-phenyl)-ethyl]-phenyl}-(3-methyl-but-2-enyl)-amino]-piperidin-1-yl}-4-methyl-pentan-1-one;

(R)-[1-(2-Amino-4-methyl-pentyl)-piperidin-4-yl]-[4-(4-fluoro-benzyloxy)-phenyl]-(3-methyl-butyl)-amine;

(R)-2-Amino-1-{4-[[4-(4-fluoro-benzyloxy)-phenyl]-(3-methyl-butyl)-amino]-piperidin-1-yl}-4-methyl-pentan-1-one;

(R)-[1-(2-Amino-4-methyl-pentyl)-piperidin-4-yl]-{4-[2-(4-fluoro-phenyl)-ethyl]-phenyl}-(3-methyl-butyl)-amine;

(R)-2-Amino-1-{4-[{4-[2-(4-fluoro-phenyl)-ethyl]-phenyl}-(3-methyl-butyl)-amino]-piperidin-1-yl}-4-methyl-pentan-1-one;

(R)-[1-(2-Amino-4-methyl-pentyl)-piperidin-4-yl]-(3-methyl-butyl)-(4-phenethyl-phenyl)-amine;

(R)-2-Amino-4-methyl-1-{4-[(3-methyl-butyl)-(4-phenethyl-phenyl)-amino]-piperidin-1-yl}-pentan-1-one;

(R)-[1-(2-Amino-4-methyl-pentyl)-piperidin-4-yl]-{4-[2-(4-chloro-phenyl)-ethyl]-phenyl}-(3-methyl-butyl)-amine;

(R)-2-Amino-1-{4-[{4-[2-(4-chloro-phenyl)-ethyl]-phenyl}-(3-methyl-butyl)-amino]-piperidin-1-yl}-4-methyl-pentan-1-one;

(S)-[1-(2-Amino-3-methyl-pentyl)-piperidin-4-yl]-(4-benzyloxy-phenyl)-(3-methyl-butyl)-amine;

(S)-2-Amino-1-{4-[(4-benzyloxy-phenyl)-(3-methyl-butyl)-amino]-piperidin-1-yl}-3-methyl-pentan-1-one;

(S)-[1-(2-Amino-3-methyl-pentyl)-piperidin-4-yl]-(4-cyclohexylmethoxy-phenyl)-(3-methyl-butyl)-amine;

(S)-2-Amino-1-{4-[(4-cyclohexylmethoxy-phenyl)-(3-methyl-butyl)-amino]-piperidin-1-yl}-3-methyl-pentan-1-one;

(S)-[1-(2-Amino-3-methyl-pentyl)-piperidin-4-yl]-[4-(2-cyclohexyl-ethyl)-phenyl]-(3-methyl-butyl)-amine;

(S)-2-Amino-1-{4-[[4-(2-cyclohexyl-ethyl)-phenyl]-(3-methyl-butyl)-amino]-piperidin-1-yl}-3-methyl-pentan-1-one;

(S)-[1-(2-Amino-3-methyl-pentyl)-piperidin-4-yl]-[4-(2,2-dimethyl-propoxy)-phenyl]-(3-methyl-butyl)-amine;

(S)-2-Amino-1-{4-[[4-(2,2-dimethyl-propoxy)-phenyl]-(3-methyl-butyl)-amino]-piperidin-1-yl}-3-methyl-pentan-1-one;

(S)-[1-(2-Amino-3-methyl-pentyl)-piperidin-4-yl]-[4-(3,3-dimethyl-butyl)-phenyl]-(3-methyl-butyl)-amine;

(S)-2-Amino-1-{4-[[4-(3,3-dimethyl-butyl)-phenyl]-(3-methyl-butyl)-amino]-piperidin-1-yl}-3-methyl-pentan-1-one;

(S)-[1-(2-Amino-3-methyl-pentyl)-piperidin-4-yl]-(4-benzyloxy-phenyl)-(3-methyl-but-2-enyl)-amine;

(S)-[1-(2-Amino-3-methyl-pentyl)-piperidin-4-yl]-[4-(4-fluorobenzyloxy)-phenyl]-(3-methyl-butyl)-amine;

(S)-2-Amino-1-{4-[(4-(4-fluorobenzyloxy)-phenyl)-(3-methyl-butyl)-amino]-piperidin-1-yl}-3-methyl-pentan-1-one;

(S)-[1-(2-Amino-3-methyl-pentyl)-piperidin-4-yl]-[4-(2-cyclohexyl-ethyl)-phenyl]-(3-methyl-but-2-enyl)-amine;

(S)-2-Amino-1-{4-[[4-(2-cyclohexyl-ethyl)-phenyl]-(3-methyl-but-2-enyl)-amino]-piperidin-1-yl}-3-methyl-pentan-1-one;

(S)-[1-(2-Amino-3-methyl-pentyl)-piperidin-4-yl]-[4-(3,3-dimethyl-butyl)-phenyl]-(3-methyl-but-2-enyl)-amine;

(S)-2-Amino-1-{4-[[4-(3,3-dimethyl-butyl)-phenyl]-(3-methyl-but-2-enyl)-amino]-piperidin-1-yl}-3-methyl-pentan-1-one;

(S)-[1-(2-Amino-3-methyl-pentyl)-piperidin-4-yl]-[4-(4-chloro-benzyloxy)-phenyl]-(3-methyl-butyl)-amine;

(S)-2-Amino-1-{4-[[4-(4-chloro-benzyloxy)-phenyl]-(3-methyl-butyl)-amino]-piperidin-1-yl}-3-methyl-pentan-1-one;

(S)-[1-(2-Amino-3-methyl-pentyl)-piperidin-4-yl]-{4-[2-(4-fluoro-phenyl)-ethyl]-phenyl}-(3-methyl-butyl)-amine;
(S)-2-Amino-1-{4-[{4-[2-(4-fluoro-phenyl)-ethyl]-phenyl}-(3-methyl-but-2-enyl)-amino]-piperidin-1-yl}-3-methyl-pentan-1-one;
(S)-[1-(2-Amino-3-methyl-pentyl)-piperidin-4-yl]-(3-methyl-but-2-enyl)-(4-phenethyl-phenyl)-amine;
(S)-2-Amino-3-methyl-1-{4-[(3-methyl-but-2-enyl)-(4-phenethyl-phenyl)-amino]-piperidin-1-yl}-pentan-1-one;
(S)-[1-(2-Amino-3-methyl-pentyl)-piperidin-4-yl]-{4-[2-(4-chloro-phenyl)-ethyl]-phenyl}-(3-methyl-but-2-enyl)-amine;
(S)-2-Amino-1-{4-[{4-[2-(4-chloro-phenyl)-ethyl]-phenyl}-(3-methyl-but-2-enyl)-amino]-piperidin-1-yl}-3-methyl-pentan-1-one;
(S)-[1-(2-Amino-4-methyl-pentyl)-piperidin-4-yl]-[4-(4-fluoro-benzyloxy)-phenyl]-(3-methyl-butyl)-amine;
(S)-2-Amino-1-{4-[[4-(4-fluoro-benzyloxy)-phenyl]-(3-methyl-butyl)-amino]-piperidin-1-yl}-4-methyl-pentan-1-one;
(S)-[1-(2-Amino-3-methyl-pentyl)-piperidin-4-yl]-{4-[2-(4-fluoro-phenyl)-ethyl]-phenyl}-(3-methyl-butyl)-amine;
(S)-2-Amino-1-{4-[{4-[2-(4-fluoro-phenyl)-ethyl]-phenyl}-(3-methyl-butyl)-amino]-piperidin-1-yl}-3-methyl-pentan-1-one;
(S)-[1-(2-Amino-3-methyl-pentyl)-piperidin-4-yl]-(3-methyl-butyl)-(4-phenethyl-phenyl)-amine;
(S)-2-Amino-3-methyl-1-{4-[(3-methyl-butyl)-(4-phenethyl-phenyl)-amino]-piperidin-1-yl}-pentan-1-one;
(S)-[1-(2-Amino-3-methyl-pentyl)-piperidin-4-yl]-{4-[2-(4-chloro-phenyl)-ethyl]-phenyl}-(3-methyl-butyl)-amine; and
(S)-2-Amino-1-{4-[{4-[2-(4-chloro-phenyl)-ethyl]-phenyl}-(3-methyl-butyl)-amino]-piperidin-1-yl}-3-methyl-pentan-1-one.

DETAILED DESCRIPTION OF THE INVENTION

The present invention provides compounds having the Formula I

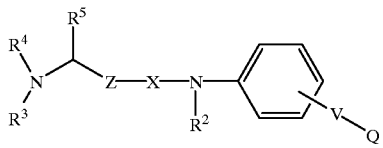

I wherein
each m is independently 1 to 3;
each n is independently 0 to 3;
each $R^a$ and $R^b$ is independently hydrogen, $C_1$–$C_6$alkyl, or $R^a$ and $R^b$ together with the carbon atom to which they are bonded form a $C_3$–$C_6$cycloalkyl ring;
Z is —$CH_2$— or

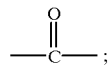

X is

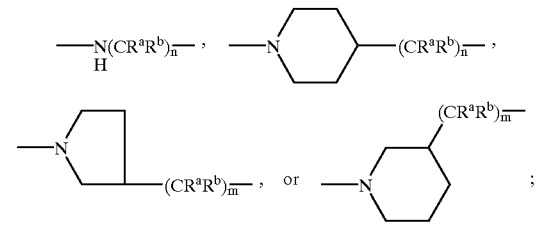

$R^5$ is $C_1$–$C_6$alkyl, —$(CH_2)_m$-heteroaryl, —$(CH_2)_m$-substituted heteroaryl, —$(CH_2)_m$-phenyl, or —$(CH_2)$-substituted phenyl;
$R^2$ is hydrogen, $C_1$–$C_8$alkenyl, $C_3$–$C_8$cycloalkenyl, phenyl, substituted phenyl, $C_1$–$C_8$alkyl, substituted $C_1$–$C_8$alkyl, —$(CH_2)_m$ substituted $C_3$–$C_8$cycloalkyl, —$(CH_2)_m$—$C_3$–$C_8$cycloalkyl, $C_3$–$C_8$cycloalkyl, substituted $C_3$–$C_8$cycloalkyl, —$(CH_2)_m$-phenyl, or —$(CH_2)_m$ substituted phenyl;
$R^3$ is hydrogen, $C_1$–$C_6$alkyl, or $C_2$–$C_6$alkenyl;
Q is aryl, heteroaryl, substituted heteroaryl, $C_3$–$C_8$cycloalkyl, substituted $C_3$–$C_8$cycloalkyl, $C_1$–$C_6$alkyl, substituted $C_1$–$C_6$alkyl, hydrogen, $C_3$–$C_8$heterocycloalkyl, $C_3$–$C_8$ substituted heterocycloalkyl, or substituted aryl;
V is

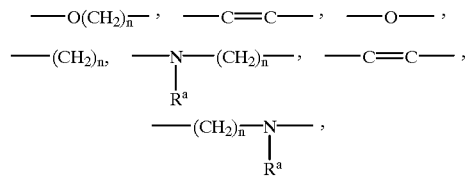

or —$(CH_2)_n$—O—;
$R^4$ is hydrogen,

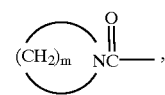

$C_1$–$C_6$alkyl, $C_2$–$C_8$alkenyl, $C_3$–$C_8$cycloalkenyl, $C_3$–$C_8$ substituted cycloalkenyl, —$(CH_2)_m$-phenyl, —$(CH_2)_m$-heteroaryl, —$(CH_2)_m$-substituted heteroaryl, —$(CH_2)_m$-substituted phenyl, $C_3$–$C_8$cycloalkyl, or $C_3$–$C_8$ substituted cycloalkyl;
or $R^3$ and $R^4$ together with the nitrogen atom to which they are bonded can form a 5–7 membered ring that can contain one or more heteroatom;
and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The term "heterocycloalkyl" means a cycloalkyl group in which one or more carbon atom has been replaced by a heteroatom.

The term "cycloalkenyl" means a cycloalkyl group having one or more carbon-carbon double or triple bond. Example includes cyclobutene, cyclopentene, cyclohexene, cycloheptene, cyclobutadiene, cyclopentadiene, and the like.

The symbol "—" means a bond.

The term "patient" means all animals including humans. Examples of patients include humans, cows, dogs, cats, goats, sheep, and pigs.

The term "substituted" means that the base organic radical has one or more substituents. For example, substituted cyclohexyl means a cyclohexyl radical that has one or more substituents. Substituents include, but are not limited to, halogen, $C_1$–$C_8$alkyl, —CN, $CF_3$, —$NO_2$, —$NH_2$, —$NHC_1$–$C_8$alkyl, —$N(C_1$–$C_8$alkyl$)_2$, —$OC_1$–$C_8$alkyl, and —OH. Particularly preferred substituents include, but are not limited to tert-butyl, methyl, chlorine, fluorine, bromine, —$OCH_3$, —$OCH_2CH_3$, —OH, and —$N(CH_3)_2$.

The term "cycloalkenyl" means a cycloalkyl group having at least one carbon-carbon double bond. Examples of cycloalkenyl groups include cyclopentene, cyclobutene, and cyclohexene.

The term "heterocycle" means a cycloalkyl group wherein one or more carbon atom is replaced with a heteroatom. Examples of heterocycles include, but are not limited to, pyrrolidinyl, piperidinyl, and piperazinyl.

Those skilled in the art are easily able to identify patients having a stroke or at risk of having a stroke; cerebral ischemia; head trauma; or epilepsy. For example, patients who are at risk of having a stroke include, but is not limited to patients having hypertension or undergoing major surgery.

A therapeutically effective amount is an amount of a compound of Formula I, that when administered to a patient, ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$alkyl esters wherein the alkyl group is a straight or branched chain. Acceptable esters also include $C_5$–$C_7$cycloalkyl esters as well as arylalkyl esters such as, but not limited to benzyl. $C_1$–$C_4$alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$alkyl amines and secondary $C_1$–$C_6$dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$alkyl primary amines, and $C_1$–$C_2$dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

The following abbreviations are used throughout this application:

| | |
|---|---|
| Pr | propyl |
| Et | ethyl |
| HBTU | 2-(1H-benzotriazol-1yl)-1,1,3,3-tetramethyl uronium hexafluorophosphate |
| Bz or Bn | benzyl |
| TFA | trifluoroacetic acid |
| APCl | atmospheric pressure chemical ionization |
| NMR | nuclear magnetic resonance |
| TLC | thin layer chromatography |
| HPLC | high pressure liquid chromatography |
| DMF | dimethyl formamide |
| EtOAC | ethyl acetate |
| EtOH | ethanol |
| MS | mass spectrum |
| DCM | dichloromethane |
| $Et_3N$ | triethyl amine |
| THF | tetrahydrofuran |

| | -continued |
|---|---|
| IR | infrared spectrum |
| OAc | acetate |
| bu | butyl |
| iso-pr | iso-propyl |
| mp | melting point |
| Leu | Leucine |
| FMOC | 9-fluorenylmethyloxycarbonyl |
| BOC | tertiary butyloxycarbonyl |
| MeOH | methanol |
| psi | pounds per square inch |
| Hac-Leu | (R)-2 [(Azepane-1-carbonyl)-amino]-4-methyl-pentanoic acid |
| MS | mass spectrum |

General Procedure for the Preparation of Calcium Channel Blockers

Schemes III, IV, and V below illustrate the preparation of the compounds of the present invention (II). The preparation of intermediates (I) is illustrated in Schemes I and II.

Step I: The Preparation of Intermediate I

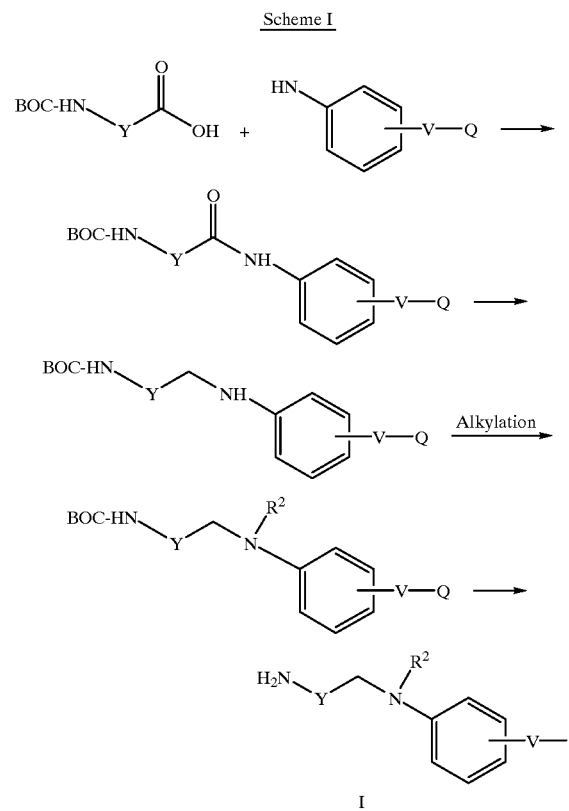

Step II: The Preparation of the Compounds of the Present Invention (II)

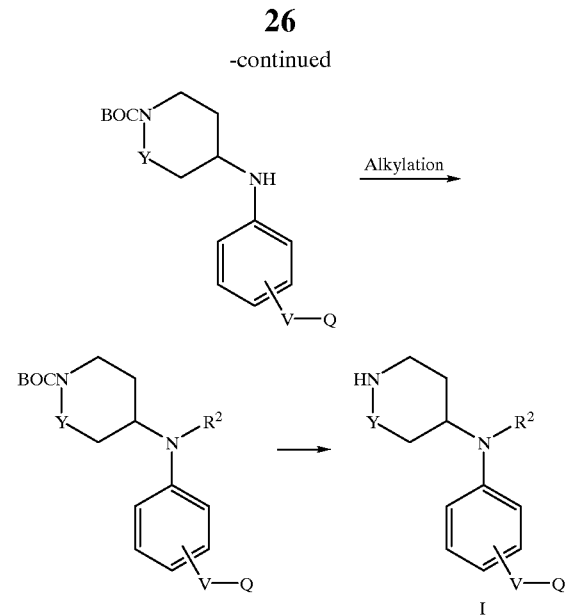

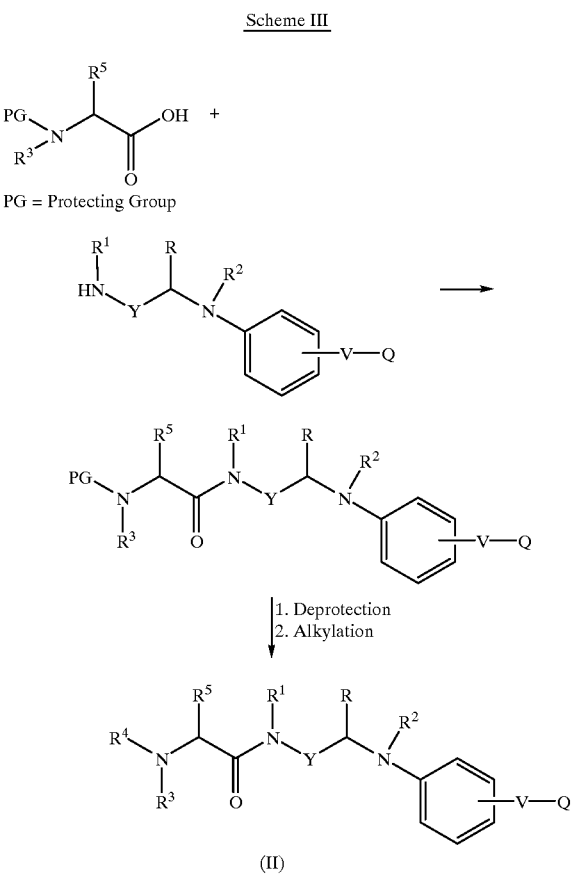

Scheme IV
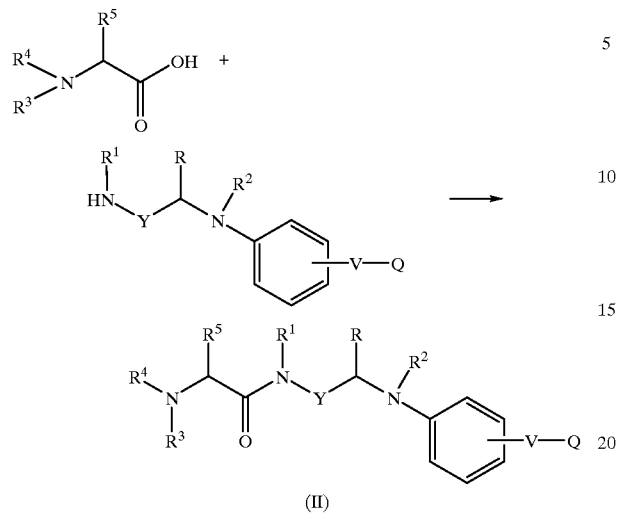
Scheme V
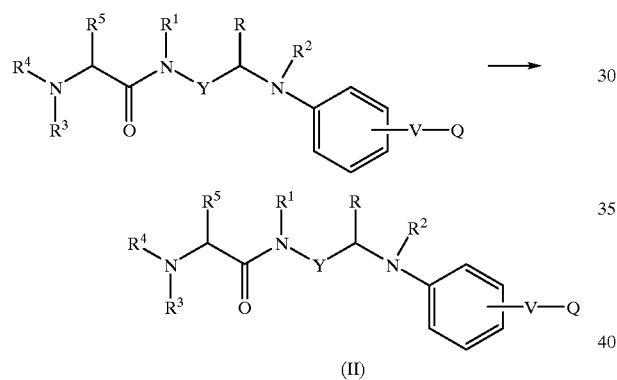
where each R and Y are appropriate molecular entities with regard to Formula I.
EXAMPLE 1
(S)-Azepane-1-carboxylic acid (1-{2-[4-benzyloxy-phenyl)-(3-methyl-but-2-enyl)-amino]-1,1-dimethyl-ethylcarbamoyl}-3-methyl-butyl)-amide
Scheme VI
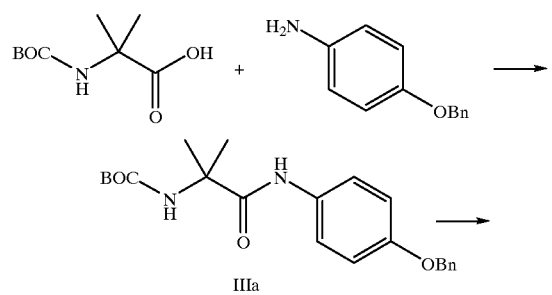
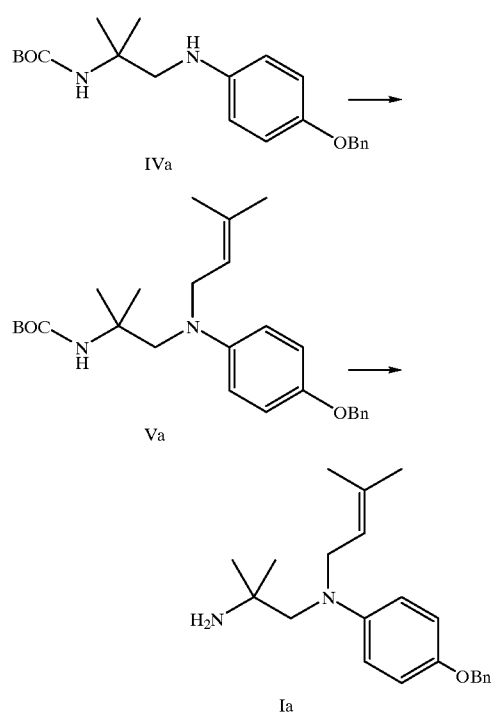
Scheme VII
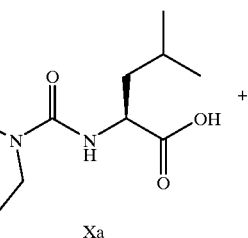
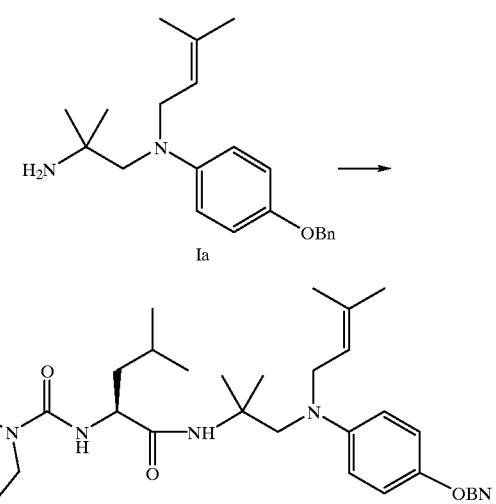

Step 1. [1-(4-Benzyloxy-phenylcarbamoyl)-1-methyl-ethyl]-carbamic acid tert-butyl ester (IIIa)4-Benzyloxyaniline (5.05 g, 25.4 mmol) was dissolved in acetonitrile (125 mL) and treated with diisopropylethylamine (6.6 mL, 38.1 mmol), N-BOC-alpha-amino-isobutyric acid (5.16 g, 25.4 mmol), and HBTU (9.63 g, 25.4 mmol). The solution was stirred for 3 hours, then concentrated in vacuo. The residue was dissolved in EtOAc and filtered, then washed twice with saturated bicarbonate solution, once with brine, dried over $Na_2SO_4$, and concentrated. The crude material was chromatographed on silica gel eluting with 4% $MeOH/CH_2Cl_2$ to give 6.54 g (67%) of the desired product.MS: 386 (M+1 for $C_{22}H_{28}N_2O_4$); TLC: $SiO_2$, $R_f$ 0.25 (2:1 hexane/EtOAc)

Step 2. [2-(4-Benzyloxy-phenylamino)-1,1-dimethyl-ethyl]-carbamic acid tert-butyl ester (IVa)[1-(4-Benzyloxy-phenylamino)-1,1-dimethyl-ethyl]-carbamic acid tert-butyl ester, IIIa (6.54 g, 17.0 mmol) was dissolved in THF (50 mL) and cooled to 0° C. A solution of diborane (51 mL, 1.0 M) in THF was added and the reaction mixture was kept at 0° C. for 10 minutes, then heated to 65° C. for 18 hours. The reaction was cooled to room temperature and treated with 0.1 M HCl (100 mL), then neutralized with saturated sodium bicarbonate solution. The aqueous layer was extracted three times with EtOAc, dried over $Na_2SO_4$, and concentrated. The residue was chromatographed on silica gel eluting with 5:1 hexane/EtOAc to give 1.32 g (22%) of the desired product as an oil.MS: 372 (M+1 for $C_{22}H_{30}N_2O_3$); TLC: $SiO_2$, $R_f$ 0.33 (5:1 hexane/EtOAc)

Step 3. {2-[(4-Benzyloxy-phenyl)-(3-methyl-but-2-enyl)-amino]-1,1-dimethyl-ethyl}-carbamic acid tert-butyl ester (Va)[2-(4-Benzyloxy-phenylamino)-1,1-dimethyl-ethyl]-carbamic acid tert-butyl ester (IVa) (0.6 g, 1.62 mmol) was dissolved in THF (32 mL) and treated with diisopropylethylamine (1.1 mL, 6.48 mmol) and 4-bromo-2-methyl-2-butene (0.37 mL, 3.24 mmol). The solution was heated to 40° C. overnight. The solution was cooled to room temperature, filtered, and concentrated. The residue was chromatographed on silica gel eluting with 8:1 hexane/EtOAc to give 0.56 (81%) of the desired product.MS: 440 (M+1 for $C_{27}H_{38}N_2O_3$); TLC: $SiO_2$, $R_f$ 0.54 (2:1 hexane/EtOAc)

Step 4. N-1-(4-Benzyloxy-phenyl)-2-methyl-N-1-(3-methyl-but-2-enyl)-propane-1,2-diamine (Ia){2-[(4-Benzyloxy-phenyl)-(3-methyl-but-2-enyl)-amino]-1,1-dimethyl-ethyl}-carbamic acid tert-butyl ester (Va) (0.56 g, 1.32 mmol) was dissolved in $CH_2Cl_2$ (7 mL) and treated with TFA (3 mL). The solution was stirred for 2.5 hours, then concentrated. The residue was twice redissolved in toluene and concentrated. The residue was dissolved in EtOAc, washed 3 times with saturated sodium bicarbonate solution, once with brine, dried over $Na_2SO_4$, and concentrated to give the desired product.MS: 340 (M+1 for $C_{22}H_{30}N_2O_1$); TLC: $SiO_2$, $R_f$ 0.29 (10% $MeOH/CH_2Cl_2$)

Step 5. Preparation of (S)-2-[(Azepane-1-carbonyl)-amino]-4-methyl-pentanoic acid (Xa)

Step i: Hac-Leu-OBnA solution of triphosgene (15.7 g, 52.9 mmol) in $CH_2Cl_2$ (600 mL) was cooled to −10° C. The solution was treated dropwise with a solution of Leu-OBn (28.1 g, 127 mmol) and pyridine (26 mL, 320 mmol) in $CH_2Cl_2$ (150 mL). The reaction was stirred at −10° C. for 90 minutes and then treated with a solution of hexamethylenamine (22 mL, 380 mmol) in $CH_2Cl_2$ (75 mL). The solution was stirred for 48 hours at room temperature. The reaction mixture was concentrated and the residue was dissolved in ether and washed with 1N HCl solution, water, and saturated aqueous $CuSO_4$ solution. The organic layer was dried over $MgSO_4$, treated with activated charcoal, and filtered. The filtrate was concentrated to 1/2 volume and treated with hexane. The resulting suspension was stored overnight at −10° C. The solid was collected by filtration, washed with hexane, and dried under vacuum to give 38.6 g (88%) of the desired product as a white solid.MS: 347 (M+1 for $C_{20}H_{30}N_2O_3$); TLC: $SiO_2$, $R_f$ 0.2 (2:1 hexane/EtOAc)

Step ii: (S)-2-[(Azepane-1-carbonyl)-amino]-4-methyl-pentanoic acid (Xa)A solution of Hac-Leu-OBn (8.97 g, 25.9 mmol) in THF (100 mL) was hydrogenated at 50 psi over Pd/C (0.25 g, 20% Pd) for 16 hours. The reaction mixture was filtered through Celite and concentrated to dryness. The residue was heated in hexane (50 mL). The resulting suspension was cooled and the solid collected by filtration and washed with hexane. The solid was dried at room temperature under vacuum to give 6.1 g (92%) of the desired product Xa as a white solid.MS: 258 (M+1 for $C_{13}H_{24}N_2O_3$); mp 88–89° C.

Step 6. Example 1: (S)-Azepane-1-carboxylic acid (1-{2-[(4-benzyloxy-phenyl)-(3-methyl-but-2-enyl)-amino]-1,1-dimethyl-ethylcarbamoyl}3-methyl-butyl)-amideN-1-(4-Benzyloxy-phenyl)-2-methyl-N-1-(3-methyl-but-2-enyl)-propane-1,2-diamine (Ia) (0.45 g, 1.32 mmol) was dissolved in DMF (7 mL) and treated with diisopropylethylamine (1.4 mL, 7.9 mmol), Hac-leucine (0.34 g, 1.32 mmol), and HBTU (0.5 g, 1.32 mmol). The reaction was stirred for 1 hour, then diluted with EtOAC, washed once with saturated sodium bicarbonate solution, once with brine, dried over $Na_2SO_4$, and concentrated. The residue was chromatographed on silica gel eluting with 2:1 hexane/EtOAc to give 0.57 g (75%) of the desired product.MS: 578 (M+1 for $C_{35}H_{52}N_4O_3$); TLC: $SiO_2$, $R_f$ 0.3 (2:1 hexane/EtOAc)

EXAMPLE 2

[S-(R*,R*)]-Azepane-1-carboxylic acid (1-{2-[(4-benzyloxy-phenyl)-(3-methyl-but-2-enyl)-amino]-1-methyl-ethylcarbamoyl}-3-methyl-butyl)-amide Step 1: (S)-[1-(4-Benzyloxy-phenylcarbamoyl)-ethyl]-carbamic acid tert-butyl ester (IIIb)IIIb is made in accordance with the process of IIIa in Example 1 (Step 1), except N-Boc-L-Alanine was used instead of N-Boc-α-amino-isobutyric acid.MS: 371 (M+1 for $C_{21}H_{26}N_2O_4$); TLC: $SiO_2$, $R_f$ 0.25 (2:1 hexane/EtOAc)

Step 2: (S)-[2-(4-Benzyloxy-phenylamino)-1-methyl-ethyl]-carbamic acid tert-butyl ester (IVb)IVb is made in accordance with the process of IVa in Example 1 (Step 2), except that IIIb was used instead of IIIa.MS: 357 (M+1 for $C_{21}H_{28}N_2O_3$); TLC: $SiO_2$, $R_f$ 0.44 (2:1 hexane/EtOAc)

Step 3: (S)-{2-[(4-Benzyloxy-phenyl)-(3-methyl-but-2-enyl)-amino]-1-methyl-ethyl}-carbamic acid tert-butyl ester (Vb)Vb is made in accordance with the process of Va in Example 1 (Step 3), except that IVb was used instead of IVa.MS: 426 (M+1 for $C_{26}H_{36}N_2O_3$); TLC: $SiO_2$, $R_f$ 0.76 (2:1 hexane/EtOAc)

Step 4: (S)-$N^1$-(4-Benzyloxy-phenyl)-$N^1$-(3-methyl-but-2-enyl)-propane-1,2-diamine (Ib)Ib is made in accordance with the process of Ia in Example 1 (Step 4), except that Vb was used instead of Va.MS: 325 (M+1 for $C_{21}H_{28}N_2O_1$); TLC: $SiO_2$, $R_f$ 0.48 (10% $MeOH/CH_2Cl_2$)

Step 5: Example 2: [S-(R*,R*)]-Azepane-1-carboxylic acid (1-{2-[(4-benzyloxy-phenyl)-(3-methyl-but-2-enyl)-amino]-1-methyl-ethylcarbamoyl}-3-methyl-butyl)-amide Example 2)Example 2 is made in accordance with the process of Example 1 (Step 6), except that Ib was used instead of Ia.MS: 564 (M+1 for $C_{34}H_{50}N_4O_3$); TLC: $SiO_2$, $R_f$ 0.67 (18% acetone/$CH_2Cl_2$)

EXAMPLE 3

(S)-Azepane-1-carboxylic acid (1-{2-[(4-benzyloxy-phenyl)-(3-methyl-but-2-enyl)-amino]-ethylcarbamoyl}-3-methyl-butyl)-amide Step 1: [(4-Benzyloxy-phenylcarbamoyl)-methyl]-carbamic acid tert-butyl ester (IIIc)IIIc is made in accordance with the process of IIIa in Example 1 (Step 1), except N-Boc-Glycine was used instead of N-Boc-α-amino-isobutyric acid.TLC: SiO$_2$, R$_f$ 0.7 (EtOAc)

Step 2: [2-(4-Benzyloxy-phenylamino)-ethyl]-carbamic acid tert-butyl ester (IVc)IVc is made in accordance with the process of IVa in Example 1 (Step 2), except that IIIc was used instead of IIIa.

Step 3: {2-[(4-Benzyloxy-phenyl)-(3-methyl-but-2-enyl)-amino]-ethyl}-carbamic acid tert-butyl ester (Vc)Vc is made in accordance with the process of Va in Example 1 (Step 3), except that IVc was used instead of IVa.

Step 4: N$^1$-(4-Benzyloxy-phenyl)-N$^{1'}$-(3-methyl-but-2-enyl)-ethane-1,2-diamine (Ic)Ic is made in accordance with the process of Ia in Example 1 (Step 4), except that Vc was used instead of Va.

Step 5: (S)-Azepane-1-carboxylic acid (1-{2-[(4-benzyloxy-phenyl)-(3-methyl-but-2-enyl)-amino]-ethylcarbamoyl}-3-methyl-butyl)-amide (Example 3)Example 3 is made in accordance with the process of Example 1 (Step 6), except that Ic was used instead of Ia.MS: 548 (M+1 for C$_{38}$H$_{48}$N$_4$O$_3$); mp 71–71° C.; TLC: SiO$_2$, R$_f$ 0.2 (1:1 hexanes/EtOAc)

EXAMPLE 4

(S)-Azepane-1-carboxylic acid (1-{3-[(4-benzyloxy-phenyl)-(3-methyl-but-2-enyl)-amino]-propylcarbamoyl}-3-methyl-butyl)-amide Step 1: [2-(4-Benzyloxy-phenylcarbamoyl)-ethyl]-carbamic acid tert-butyl ester (IIId)IIId is made in accordance with the process of IIIa in Example 1 (Step 1), except N-Boc-β-Alanine was used instead of N-Boc-α-amino-isobutyric acid.MS: 371 (M+1 for C$_{21}$H$_{26}$N$_2$O$_4$); TLC: SiO$_2$, R$_f$ 0.27 (5% MeOH/CH$_2$Cl$_2$)

Step 2: [3-(4-Benzyloxy-phenylamino)-propyl]-carbamic acid tert-butyl ester (IVd)IVd is made in accordance with the process of IVa in Example 1 (Step 2), except that IIId was used instead of IIIa.MS: 358 (M+1 for C$_{21}$H$_{28}$N$_2$O$_3$); TLC: SiO$_2$, R$_f$ 0.25 (2:1 hexane/EtOAc)

Step 3: {3-[(4-Benzyloxy-phenyl)-(3-methyl-but-2-enyl)-amino]-propyl}-carbamic acid tert-butyl ester (Vd)Vd is made in accordance with the process of Va in Example 1 (Step 3), except that IVd was used instead of IVa.MS: 426 (M+1 for C$_{26}$H$_{36}$N$_2$O$_3$); TLC: SiO$_2$, R$_f$ 0.8 (2:1 hexanes/EtOAc)

Step 4: N$^1$-(4-Benzyloxy-phenyl)-N$^{1'}$-(3-methyl-but-2-enyl)-propane-1,3-diamine (Id)Id is made in accordance with the process of Ia in Example 1 (Step 4), except that Vd was used instead of Vc.MS: 326 (M+1 for C$_{21}$H$_{28}$N$_2$O$_1$); TLC: SiO$_2$, R$_f$ 0.48 (10% MeOH/CH$_2$Cl$_2$)

Step 5: (S)-Azepane-1-carboxylic acid (1-{3-[(4-benzyloxy-phenyl)-(3-methyl-but-2-enyl)-amino]-propylcarbamoyl}-3-methyl-butyl)-amide (Example 4)Example 4 is made in accordance with the process of Example 1 (Step 6), except that Id was used instead of Ia.MS: 564 (M+1 for C$_{34}$H$_{50}$N$_4$O$_3$); mp 48–52° C.

EXAMPLE 5

(S)-Azepane-1-carboxylic acid (1-{4-[(4-benzyloxy-phenyl)-(3-methyl-but-2-enyl)-amino]-piperidine-1-carbonyl}-3-methyl-butyl)-amide hydrochloride salt

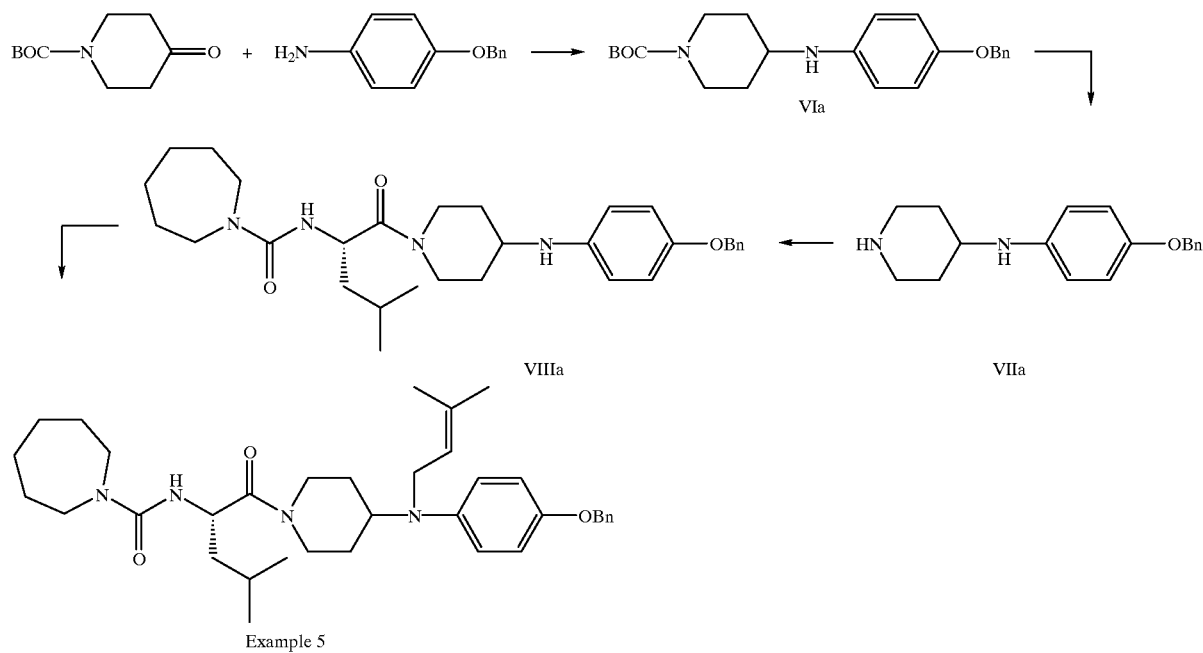

Scheme VIII

Example 5

Step 1: 4-(4-Benzyloxy-phenylamino)-piperidine-1-carboxylic acid tert-butyl ester (VIa)4-Benzyloxyaniline hydrochloride salt (10 g, 42.4 mmol) was suspended in EtOAc (500 mL) and washed 3 times with saturated sodium bicarbonate solution, once with brine, dried over Na$_2$SO$_4$, and concentrated. The free base was dissolved in $CH_2Cl_2$ (250 mL), treated with 1-tert-butyl-carbonyl-4-piperidone (8.45 g, 42.4 mmol), stirred for 30 minutes and then cooled to 0° C. $NaBH(OAc)_3$ (13.5 g, 63.6 mmol) was added and the reaction was allowed to warm to room temperature and stirred for 18 hours. The reaction was diluted with $CH_2Cl_2$ (250 mL), washed with saturated sodium bicarbonate solution and brine, dried over $Na_2SO_4$, and concentrated to give 15.3 g (94%) of the desired product.MS: 383 (M+1 for $C_{23}H_{30}N_2O_3$); TLC: $SiO_2$, $R_f$ 0.39 (2:1 hexane/EtOAc)

Step 2: 4-(4-Benzyloxy-phenylamino)-piperidine (VIIa)A solution of VIa (3 g, 7.84 mmol) in $CH_2Cl_2$ (20 mL) was treated with TFA (20 mL) and stirred for 30 minutes. The reaction was concentrated, diluted with EtOAc, washed with saturated sodium bicarbonate solution and brine, dried over $Na_2SO_4$, and concentrated to give 1.56 g of the desired product.MS: 283 (M+1 for $C_{18}H_{22}N_2O_1$); TLC: $SiO_2$, Rf 0.31 (10% $MeOH/CH_2Cl_2$)

Step 3: (S)-Azepane-1-carboxylic acid {1-[4-(4-benzyloxy-phenylamino)-piperidine-1-carbonyl]-3-methyl-butyl}-amide (VIIIa)A solution of VIIa (0.564 g, 2 mmol) in DMF (8 mL) was treated with Hac-leucine (Xa, 0.51 g, 2 mmol), diisopropylethylamine (0.5 g, 4 mmol), and HBTU (0.76 g, 2 mmol). The reaction was stirred at room temperature, then diluted with EtOAc, washed with saturated sodium bicarbonate solution and brine, dried over $Na_2SO_4$, and concentrated to give 1.1 g of the desired product.MS: 521 (M+1 for $C_{31}H_{44}N_4O_3$); TLC: $SiO_2$, $R_f$ 0.25 (EtOAc)

Step 4: (S)-Azepane-1-carboxylic acid (1-{4-[(4-benzyloxy-phenyl)-(3-methyl-but-2-enyl)-amino]-1-piperidine-1-carbonyl}-3-methyl-butyl)-amide hydrochloride salt (Example 5)A solution of VIIIa (0.39 g, 0.75 mmol) in THF (15 mL) was treated with diisopropylethylamine (0.4 g, 3 mmol), and 4-bromo-2-methyl-2-butene (0.149 g, 1 mmol). The reaction was heated to 40° C. for 18 hours, then concentrated. The residue was chromatographed on silica gel to give the free base of the desired product. The free base was dissolved in diethyl ether, treated with 1 M HCl in ether, and concentrated to give the desired product hydrochloride salt.MS: 588 (M+1 for $C_{36}H_{52}N_4O_3$); mp 125–126° C.

EXAMPLE 6

(S)-Azepane-1-carboxylic acid (1-{2-[(4-benzyloxy-phenyl)-cyclohex-2-enyl-amino]-ethylcarbamoyl}-3-methyl-butyl)-amide Step 1: {2-[(4-Benzyloxy-phenyl)-cyclohex-2enyl-amino]-ethyl}-carbamic acid tert-butyl ester (Ve)(Ve) is made in accordance with the process of Steps 1–3 in Example 3 except that 3-bromo-cyclohexene was used instead of 4-bromo-2-methyl-2-butene in Step 3.TLC: $SiO_2$, $R_f$ 0.7 (2:1 hexane/EtOAc)

Step 2: $N^1$-(4-Benzyloxy-phenyl)-$N^1$-cyclohex-2-enyl-ethane-1,2-diamine (Ie)Ie is made in accordance with the process of Ic in Example 3 (Step 4), except that Ve was used instead of Vc.

Step 3: (S)-Azepane-1-carboxylic acid (1-{2-[(4-benzyloxy-phenyl)-cyclohex-2-enyl-amino]-ethylcarbamoyl}-3-methyl-butyl)-amide (Example 6)Example 6 is made in accordance with the process of Example 3 (Step 5), except that Ie was used instead of Ic.MS: 560 (M+1 for $C_{34}H_{48}N_4O_3$); mp 79–80° C.; TLC: $SiO_2$, $R_f$ 0.6 (EtOAc)

EXAMPLE 7

(S)-Azepane-1-carboxylic acid (1-{2-[benzyl-(4-benzyloxy-phenyl)-amino]-ethylcarbamoyl}-3-methyl-butyl)-amide Step 1: [2-(4-Benzyloxy-phenylamino)-ethyl]-carbamic acid tert-butyl ester (IVf)IVf is made in accordance with the process of Steps 1–2 in Example 3.

Step 2: $N^1$-Benzyl-N-(4-benzyloxy-phenyl)-$N^{1-}$-tert-butoxymethyl-ethane-1,2-diamine (Vf)IVf (0.686 g, 2 mmol) was dissolved in THF (25 mL) and treated with diisopropylethylamine (0.5 g, 4 mmol), and benzyl bromide (0.342 g, 2 mmol). The reaction was heated to 45° C. for 18 hours, then filtered and concentrated. The residue was chromatographed on silica gel to give 0.1 g of the desired product.

Step 3: $N^1$-Benzyl-$N^1$-(4-benzyloxy-phenyl)-ethane-1,2-diamine (If)If is made in accordance with the process of Ic in Example 3 (Step 4), except that Vf was used instead of Vc.

Step 4: (S)-Azepane-1-carboxylic acid (1-{2-[benzyl-(4-benzyloxy-phenyl)-amino]-ethylcarbamoyl}-3-methyl-butyl)-amide (Example 7)Example 7 is made in accordance with the process of Example 3 (Step 5), except that If was used instead of Ic.MS: 572 (M+1 for $C_{35}H_{46}N_4O_3$); mp 65–66° C; TLC: $SiO_2$, $R_f$ 0.8 (EtOAc)

EXAMPLE 8

(S)-Azepane-1-carboxylic acid (1-{2-[(4-benzyloxy-phenyl)-cyclohex-2-enyl-amino]-1,1-dimethyl-ethylcarbamoyl}-3-methyl-butyl)-amide Step 1: {2-[(4-Benzyloxy-phenyl)-cyclohex-2-enyl-amino]-1,1-dimethyl-ethyl}-carbamic acid tert-butyl ester (Vg)Vg is made in accordance with the process of Steps 1–3 in Example 1 except that 3-bromo-cyclohexene was used instead of 4-bromo-2-methyl-2-butene in Step 3.TLC: $SiO_2$, $R_f$ 0.6 (5:1 hexane/EtOAc)

Step 2: $N^1$-(4-Benzyloxy-phenyl)-$N^1$-cyclohex-2-enyl-2-methyl-propane-1,2-diamine (Ig)Ig is made in accordance with the process of Ia in Example 1 (Step 4), except that Vg was used instead of Va.

Step 3: (S)-Azepane-1-carboxylic acid (1-{2-[(4-benzyloxy-phenyl)-cyclohex-2-enyl-amino]-1,1-dimethyl-ethylcarbamoyl}-3-methyl-butyl)-amide (Example 8)Example 8 is made in accordance with the process of Example 1 (Step 6), except that Ig was used instead of Ia.MS: 588 (M+1 for $C_{36}H_{52}N_4O_3$); TLC: $SiO_2$, $R_f$ 0.1 (2:1 hexane/EtOAc)

EXAMPLE 9

(S)-2-Dimethylamino-4-methyl-pentanoic acid {2-[(4-benzyloxy-phenyl)-(3-methyl-but-2-enyl)-amino]-1,1-dimethyl-ethyl}-amide Scheme IX

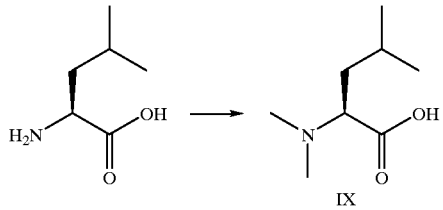

IX

Step 1: The preparation of (S)-2-(dimethyl-amino)-4-methyl-pentanoic acid (IX)(S)-2-Amino-4-methyl-pentanoic acid (10.42 g, 80 mmol) was dissolved in $H_2O$ (120 mL) and treated with formaldehyde (80 mL, 37% solution), and Raney Nickel (2 g), and stirred for 21 hours. The solution was concentrated to a solid, dissolved in hot EtOH, boiled with charcoal, and filtered through Celite. The solution was allowed to cool. Acetone was added, and the solution was placed in the refrigerator. The solution was filtered, and the crystals were washed with acetone to give 9.7 g (77%) of IX.MS: 160 (M+1 for $C_8H_{17}N_1O_2$); TLC $SiO_2$, $R_f$ 0.04 (12% $MeOH/CH_2Cl_2$)

Scheme X

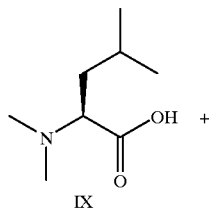

IX

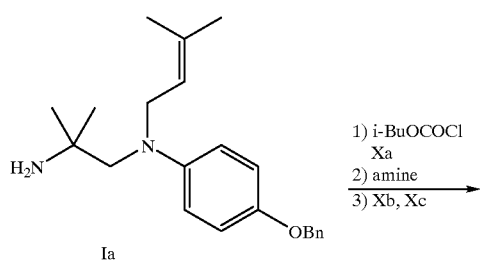

Ia 1) i-BuOCOCl
   Xa
2) amine
3) Xb, Xc

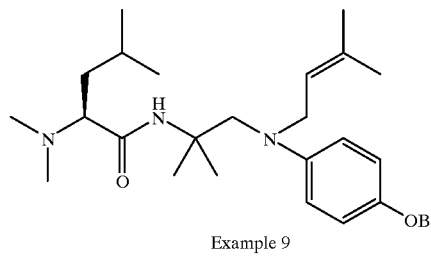

Example 9

Step 2: The Preparation of Polymer-supported resins (Xa-c)

Step i: Polymer-supported tris(2-aminoethyl)-amine (Xa) A suspension of Merrifield resin (Fluka, 50 g, 1.7 mmol Cl/g resin, 85 mmol) in DMF (500 mL) was treated with tris(2-aminoethyl)-amine (50 mL, 342 mmol). The resulting mixture was shaken at 65° C. for 6 hours under $N_2$ atmosphere. After cooling to room temperature, the resin was filtered and washed successively with MeOH, DMF, $Et_3N$, MeOH, DCM, $Et_3N$, MeOH, DCM, MeOH, DCM, and MeOH. The resulting amine resin was dried at 45–50° C., 20 mm Hg for 24 hours and stored in tightly sealed bottles.Calculated: N, 8.02; Cl, 0.00. Found: N, 5.96; Cl, 0.42 (indicates approx. 25% cross-linking).A small sample reacted with excess 3,4-dichlorophenyl isocyanate in DCM indicates a quench ing capacity of 3.18 mmol/g resin, consistent with 3/4 of the N content in the amine resin (Xa).Calculated: N, 6.51; Cl, 14.15. Found: N, 6.25; Cl, 13.99.

Step ii: Polymer-supported Isocyanate (Xb)A suspension of aminomethyl resin (Fluka, 1.1 mmol N/g resin, 15 g, 16.5 mmol) in DCM (150 mL) was treated with $Et_3N$ (11.5 mL, 83 mmol) and triphosgene (3.25 g, 2 mmol equivalents of phosgene) and shaken 5 hours at room temperature. The resulting isocyanate resin was filtered and washed DCM(2× 200 mL), $CHCl_3$(2×200 mL), $Et_2O$(1×200 mL), THF(1×200 mL), $Et_2O$(1×200 mL), THF(1×200 mL), $Et_2O$(1×200 mL). The resin was then dried at 35° C. to 40° C., 25 mm Hg for 24 hours. Yield (15 g of Xb) IR (KBr) 2260 (N=C=O).

Step iii: Polymer-supported Morpholine (Xc)A suspension of Merrifield resin (Fluka, 20 g, 4.3 mmol Cl/g resin, 86 mmol) in DMF (100 mL) was treated with morpholine (20 mL, 229 mmol). The resulting mixture was shaken at 65° C. for 6 hours under $N_2$ atmosphere, then allowed to stand at room temperature 24 hours. After cooling to room temperature, the resin was filtered and washed successively with MeOH, DMF, MeOH, $Et_3N$, DCM, MeOH, $Et_3N$, DCM, MeOH, EtOAc, and hexanes. The resulting N-methylmorpholine resin (Xc) was dried at 45° C. to 50° C., 20 mm Hg for 48 hours and stored in tightly sealed bottles.Calculated: N, 4.83; Cl, 0.00. Found: N, 4.98; Cl, 0.21.

Step 3: (S)-2-Dimethylamino-4-methyl-pentanoic acid {2-[(4-benzyloxy-phenyl)-(3-methyl-but-2-enyl)-amino]-1,1-dimethyl-ethyl}-amide (Example 9)N,N-dimethyl-L-leucine (IX, 15.9 mg, 0.1 mmol) and morpholine resin (Xc, 150 mg, 0.54 mmol) were treated with $CH_2Cl_2$ (1.5 mL) and isobutylchloroformate (18 μL, 0.14 mmol). The vial was capped and shaken for 30 minutes. Ia, (33.8 mg, 0.1 mmol) was added as a solution in dichloromethane (1 mL), and the mixture was shaken for 2 hours. Isocyanate resin (Xb, 100 mg, 0.15 mmol) and amine resin (Xa, 100 mg, 0.15 mmol) were added, and the mixture was shaken for 2 hours. The solids were filtered away through a plug of glass wool in a pipette. The solids were rinsed with 1 mL dichloromethane, and the combined solvent volume was evaporated under a stream of $N_2$ to give the desired product.MS: 481 (M+1 for $C_{30}H_{45}N_3O_2$)

EXAMPLE 10

(S)-4-Methyl-2-[methyl-(3-methyl-but-2-enyl)-amino]-pentanoic acid {2-[(4-benzyloxy-phenyl)-(3-methyl-but-2-enyl)-1,1-dimethyl-ethyl}-amide Scheme XI

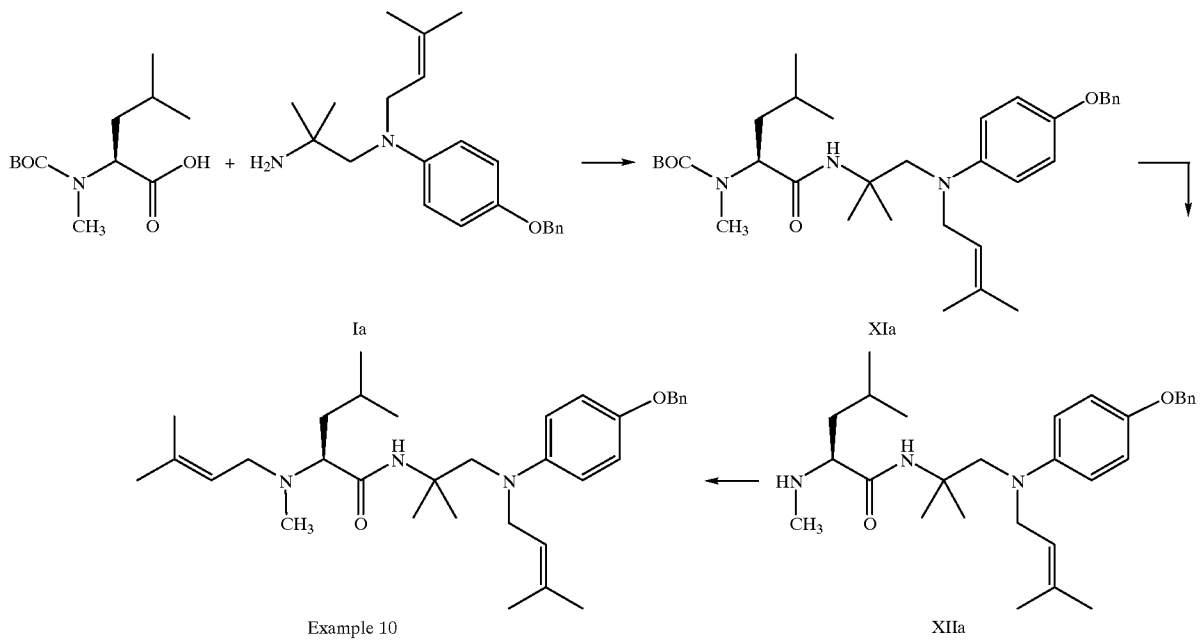

Step 1: (S)-(1-{2-[(4-Benzyloxy-phenyl)-(3-methyl-but-2-enyl)-amino-1-1,1-dimethyl-ethylcarbamoyl}-3-methyl-butyl)-methyl-carbamic acid tert-butyl ester (XIa)A mixture of Ia (0.535 g, 1.65 mmol), N-Methyl-N-Boc-L-Leucine (0.405 g, 1.65 mmol), HBTU (0.625 g, 1.65 mmol), and diisopropylethylamine (0.516 g, 6.6 mmol) was stirred in $CH_3CN$ (30 mL) for 15 hours. The reaction mixture was concentrated, redissolved in EtOAc, washed 3 times with saturated sodium bicarbonate solution and once with brine, then concentrated to give 1.2 g of the desired product.TLC: $SiO_2$, $R_f$ 0.7 (3:1 hexane/EtOAc)

Step 2: (S)-4-Methyl-2-methylamino-pentanoic acid {2-[(4-benzyloxy-phenyl)-(3-methyl-but-2-enyl)-amino]-1,1-dimethyl-ethyl}-amide (XIIa)A solution of XIa in $CH_2Cl_2$ was added to TFA, and the reaction was stirred for 30 minutes, then concentrated. The residue was dissolved in EtOAc (50 mL), washed 3 times with saturated sodium bicarbonate solution, dried over $Na_2SO_4$, and concentrated to give the desired product.TLC: $SiO_2$, $R_f$ 0.2 (EtOAc)

Step 3: (S)-4-Methyl-2-[methyl-(3-methyl-but-2-enyl)-amino]-pentanoic acid }2-[(4-benzyloxy-phenyl)-(3-methyl-but-2-enyl)-amino[-1,1-dimethyl-ethyl}-amide (Example 10)(S)-4-Methyl-2-methylamino-pentanoic acid {2-[(4-benzyloxy-phenyl)-(3-methyl-but-2-enyl)-amino]-1,1-dimethyl-ethyl}-amide (XIIa, 0.14 g, 0.31 mmol) was dissolved in THF (10 mL), treated with diisopropylethylamine (0.31 g, 2.4 mmol), and 4-bromo-2-methyl-2-butene (0.6 mmol), and heated to 50° C. for 15 hours. The reaction was concentrated and chromatographed on silica gel eluting with 2:1 hexane/EtOAc to yield the desired product.MS: 615 (M+1 for $C_{34}H_{51}N_3O_2$); TLC: $SiO_2$, $R_f$ 0.5 (2:1 hexane/EtOAc)

EXAMPLE 11

(S)-4-Methyl-2-[methyl-(3-methyl-butyl)-amino]-pentanoic acid {2-[(4-benzyloxy-phenyl)-(3-methyl-but-2-enyl)-amino]-1,1-dimethyl-ethyl}-amide(S)-4-Methyl-2-methylamino-pentanoic acid {2-[(4-benzyloxy-phenyl)-(3-methyl-but-2-enyl)-amino]-1,1-dimethyl-ethyl}-amide (XIa, 0.67 mmol) was dissolved in $CH_2Cl_2$ (10 mL), treated with isovaleraldehyde (60.2 mg, 0.7 mmol), and stirred for 30 minutes. The reaction was cooled to 0° C. and $NaBH(OAc)_3$ (212 mg, 1 mmol) was added. The mixture was stirred at room temperature for 15 hours, then washed with saturated sodium bicarbonate solution and concentrated. The residue was chromatographed on silica gel eluting with 4:1 hexane/EtOAc to give the desired product.MS: 535 (M+1 for $C_{34}H_{53}N_3O_2$); TLC: $SiO_2$, $R_f$ 0.8 (2:1 hexane/EtOAc)

EXAMPLE 12

(S)-2-Cyclohex-2-enyl-methyl-amino)-4-methyl-pentanoic acid {2-[(4-benzyloxy-phenyl)-(3-methyl-but-2-enyl)-amino]-1,1-dimethyl-ethyl}-amideExample 12 is made in accordance with the process of Steps 1–3 in Example 10 except that 3-bromocyclohexene was used instead of 4-bromo-2-methyl-2-butene in Step 3.MS: 545 (M+1 for $C_{35}H_{51}N_3O_2$); TLC: $SiO_2$, $R_f$ 0.6 (2:1 hexane/EtOAc)

EXAMPLE 13

(S)-2-[(4-tert-Butyl-benzyl)-methyl-amino]-4-methyl-pentanoic acid {2-[(4-benzyloxy-phenyl)-(3-methyl -but-2-enyl)-amino]-1,1-dimethyl-ethyl}-amide
Step 1Example 13 is made in accordance with the process of Example 11 except that 4-tert-butyl-benzaldehyde was usedinstead of isovaleraldehyde.MS: 611 (M+1 for $C_{40}H_{57}N_3O_2$); TLC: $SiO_2$, $R_f$ 0.7 (2:1 hexane/EtOAc)

EXAMPLE 14

[S-(R*,R*)]-2-Dimethylamino-4-methyl-pentanoic acid {2-[(4-benzyloxy-phenyl)-(3-methyl-but-2-enyl)-amino-]-1-methyl-ethyl-amide Step 1Example 14 is made in accordance with the process of Example 2 (Step 6), except N,N-dimethyl-leucine was used instead of Hac-Leucine in Step 6.MS: 467 (M+1 for $C_{29}H_{43}N_3O_2$); TLC: $SiO_2R_f$ 0.25 (33% acetone/$CH_2Cl_2$)

EXAMPLE 15

[S-(R*,R*)]-4-Methyl-2-(3-methyl-but-2-enylamino)-pentanoic acid {2-[(4-benzyloxy-phenyl)-3-methyl-but-2-enyl)-amino]-1-methyl-ethyl}-amide Step 1: (S)-(1-{2-[(4-Benzyloxy-phenyl)-(3-methyl-but-2-enyl)-amino]-1,1-dimethyl-ethylcarbamoyl}-3-methyl-butyl)-carbamic acid tert-butyl ester (XIb)XIb was made in accordance with the process of XIa in Example 10 (Step 1), except that N-Boc-Leucine was used instead of N-Boc-N-Methyl-Leucine and Ib (prepared in Example 2, Step 4) was used instead of IaMS: 540 (M+1 for $C_{32}H_{47}N_3O_4$); TLC: $SiO_2$, $R_f$ 0.79(10% acetone/$CH_2Cl_2$)

Step 2: (S)-2-Amino-4-methyl-pentanoic acid {2-[(4-benzyloxy-phenyl)-(3-methyl-but-2-enyl)-amino]-1,1-dimethyl-ethyl}-amide (XIIb)XIIb was made according to the process of XIIa in Example 10 (Step 2), except that XIb (prepared in Example 15, Step 1) was used instead of XIa.MS: 440 (M+1 for $C_{27}H_{39}N_3O_2$); TLC: $SiO_2$, $R_f$ 0.23 (10% MeOH/$CH_2Cl_2$)

Step 3: [S-(R*,R*)]-4Methyl-2-(3-methyl-but-2-enylamino)-pentanoic acid {2-[(4-benzyloxy-phenyl)-(3-methyl-but-2-enyl)-amino]-1-methyl-ethyl}-amide (Example 15)Example 15 was made in accordance with the procedure of Example 10 (Step 3), except that (S)-2-Amino-4-methyl-pentanoic acid {2-[(4-benzyloxy-phenyl)-(3-methyl-but-2-enyl)-amino]-1,1-dimethyl-ethyl}-amide (XIIb, prepared in Example 15, Step 2) was used instead of (S)-4-Methyl-2-methylamino-pentanoic acid {2-[(4-benzyloxy-phenyl)-(3-methyl-but-2-enyl)-amino]-1,1-dimethyl-ethyl}-amide (XIa). MS: 507 (M+1 for $C_{32}H_{43}N_3O_2$); TLC: $SiO_2R_f$ 0.47 (20% acetone/$CH_2Cl_2$)

EXAMPLE 16

[S-(R*,R*)]-4Methyl-2-(3-methyl-butylamino)-pentanoic acid {2-[(4-benzyloxy-phenyl)-(3-methyl-but-2-enyl)-amino]-1-methyl-ethyl}-amideExample 16 was made in accordance with the procedure of Example 11 except that (S)-2-Amino-4-methyl-pentanoic acid {2-[(4-benzyloxy-phenyl)-(3-methyl-but-2-enyl)-amino]-1,1-dimethyl-ethyl}-amide (XIIb, prepared in Example 15, Step 2) was used instead of (S)-4-Methyl-2-methylamino-pentanoic acid {2-[(4-benzyloxy-phenyl)-(3-methyl-but-2-enyl)-amino]-1,1-dimethyl-ethyl}-amide (XIa).MS: 509 (M+1 for $C_{29}H_{47}N_3O_2$); TLC: $SiO_2$, $R_f$ 0.3 (10% acetone/$CH_2Cl_2$)

EXAMPLE 17

(S)-4Methyl-2-[methyl-(3-methyl-butyl)-amino]-pentanoic acid {2-[(4-benzyloxy-phenyl)-cyclohex-2-enyl-amino]-1,1-dimethyl-ethyl}-amide Step 1: (S)-(1-{2-[(4-Benzyloxy-phenyl)-(cyclohex-2-enyl)-amino]-1,1-dimethyl-ethylcarbamoyl}-3-methyl-butyl)-methyl-carbamic acid tert-butyl ester (XIc)XIc was made in accordance with the process of XIa in Example 10 (Step 1), except that $N^1$-(4-Benzyloxy-phenyl)-$N^1$-(3-methyl-but-2-enyl)-ethane-1,2-diamine (Ic, prepared in Example 3, Step 4) was used instead of N-1-(4-Benzyloxy-phenyl)-2-methyl-N-1-(3-methyl-but-2-enyl)-propane-1,2-diamine (Ia).MS: 578 (M+1 for $C_{35}H_{51}N_3O_4$); TLC: $SiO_2$, $R_f$ 0.5 (3:1 hexane/EtOAc)

Step 2: (S)-2-Amino-4-methyl-pentanoic acid {2-[(4-benzyloxy-phenyl)-(cyclohex-2-enyl)-amino]-1,1-dimethyl-ethyl}-amide (XIIc)XIIc was made in accordance with the process of XIIa in Example 10 (Step 2), except that (S)-(1-{2-[(4-Benzyloxy-phenyl)-(cyclohex-2-enyl)-amino]-1,1-dimethyl-ethylcarbamoyl}-3-methyl-butyl)-methyl-carbamic acid tert-butyl ester (XIc) was used instead of (S)-(1-(2-[(4-Benzyloxy-phenyl)-(3-methyl-but-2-enyl)-amino]-1,1-dimethyl-ethylcarbamoyl}-3-methyl-butyl)-methyl-carbamic acid tert-butyl ester (XIa).

Step 3: (S)-4Methyl-2-[methyl-(3-methyl-butyl)-amino]-pentanoic acid {2-[(4-benzyloxy-phenyl)-cyclohex-2-enyl-amino]-1,1-dimethyl-ethyl}-amide (Example 17)Example 17 was made in accordance with the procedure of Example 11 except that (S)-2-Amino-4-methyl-pentanoic acid {2-[(4-benzyloxy-phenyl)-(cyclohex-2-enyl)-amino]-1,1-dimethyl-ethyl)}-amide (XIIc) was used instead of {2-[(4-benzyloxy-phenyl)-(3-methyl-but-2-enyl)-amino]-1,1-dimethyl-ethyl}-amide (XIIa).MS: 547 (M+1 for $C_{35}H_{52}N_3O_2$); TLC: $SiO_2$, $R_f$ 0.4 (2:1 hexane/EtOAc)

EXAMPLE 18

[S-(R*,R*)]-2-[Bis-(3-methyl-butyl)-amino]-4-methyl-pentanoic acid {2-[(4-benzyloxy-phenyl)-(3-methyl-but-2-enyl)-amino]-1-methyl-ethyl]-amideExample 18 was isolated as a side product from Step 3 of Example 16.MS: 570 (M+1 for $C_{37}H_{59}N_3O_2$); TLC: $SiO_2$, $R_f$ 0.9 (20% acetone/$CH_2Cl_2$

EXAMPLE 19

{S-(R*,R*)]-2-{Bis]-(3-methyl-but-2-enylamino)-4-Methyl-pentanoic acid {2-[(4-benzyloxy-phenyl)-(3-methyl-but-2-enyl)-amino]-1-methyl-ethyl}-amideExample 19 was isolated as a side product from Step 3 in Example 15.MS: 575 (M+1 for $C_{37}H_{55}N_3O_2$); TLC: $SiO_2R_f$ 0.87 (10% acetone/$CH_2Cl_2$)

EXAMPLE 20

(S)-2-Amino-1-{4-[(4-benzyloxy-phenyl)-(3-methyl-but-2-enyl)-amino]-piperidin-1,1-yl}-4-methyl-pentan-1-one Scheme XII

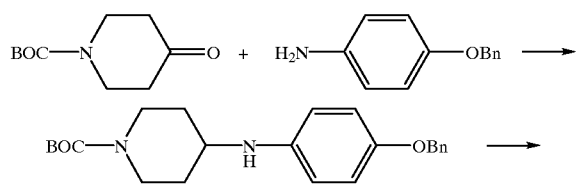

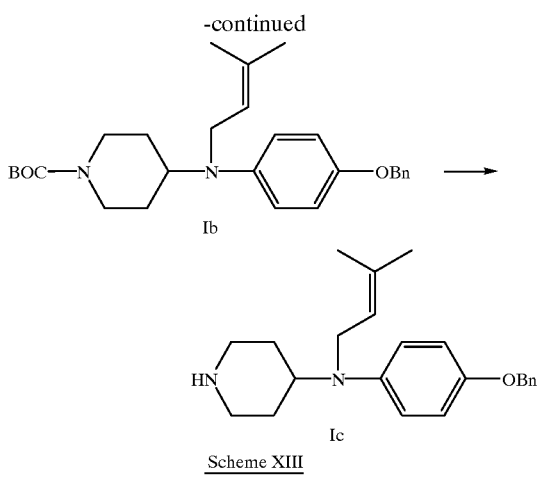

Scheme XIII

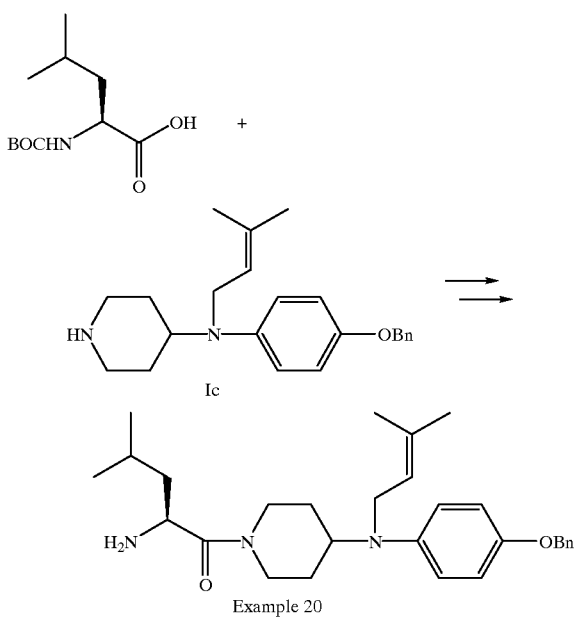

Example 20

Step 1: The preparation of 4-(Benzyloxy-phenylamino)-piperidine-1-carboxylic acid tert-butyl ester4-Benzyloxyaniline hydrochloride salt (10 g, 42.4 mmol) was suspended in EtOAc (500 mL) and washed 3 times with saturated sodium bicarbonate solution, once with brine, dried over $Na_2SO_4$, and concentrated. The free base was dissolved in $CH_2Cl_2$ (250 mL), treated with 1-tert-butyl-carbonyl-4-piperidone (8.45 g, 42.4 mmol), stirred for 30 minutes and then cooled to 0° C. $NaBH(OAc)_3$ (13.5 g, 63.6 mmol) was added and the reaction was allowed to warm to room temperature and stir for 18 hours. The reaction was diluted with $CH_2Cl_2$ (250 mL), washed with saturated sodium bicarbonate solution and brine, dried over $Na_2SO_4$, and concentrated to give 15.3 g (94%) the desired product.MS: 383 (M+1 for $C_{23}H_{30}N_2O_3$); TLC: $SiO_2$, $R_f$ 0.39 (2:1 hexane/EtOAc).

Step 2: The preparation of 4-[(Benzyloxy-phenyl)-(3-methyl-but-2-enyl)-amino]-piperidine-1-carboxylic acid tert-butyl ester (Ib)4-(4-Benzyloxy-phenylamino)-piperidine-1-carboxylic acid tert-butyl ester (5.0 g, 13.1 mmol) was dissolved in THF (65 mL), then treated with N,N-diisopropylethylamine (9.1 mL, 52.4 mmol) and 4-bromo-2-methyl-2-butene (3.0 mL, 26.2 mmol). The reaction was heated to 40° C. for 18 hours, then concentrated in vacuo. The residue was chromatographed on silica gel eluting with 5:1 hexane/EtOAc to give 5.15 g (87%) of the desired compound.MS: 451 (M+1 for $C_{28}H_{38}N_2O_3$); TLC: $SiO_2$, $R_f$ 0.26 (5:1 hexane/EtOAc).Analysis Calculated ($C_{28}H_{38}N_2O_3$): C: 74.63, H: 8.50, N: 6.22. Found: C: 74.42, H: 8.50, N: 6.22.$^1$HNMR (CDCl$_3$, ppm): δ1.42 (s, 9 h), 1.43–1.56 (m, 3 H), 1.62 (s, 3 H), 1.63 (s, 3 H), 1.74 (d, 2 H, J=11.5 Hz), 2.65 (br, 2 H), 3.41–3.45 (m, 1 H), 3.66 (J=5.4 Hz), 4.15 (br, 1 H), 4.96 (s, 2 H), 5.04 (br, 1 H), 6.71 (d, 2 H, J=9.0 Hz), 6.84 (d, 2 H, J=9.0 Hz), 7.27–7.40 (m, 5 H).

Step 3: The preparation of (4-Benzyloxy-phenyl)-(3-methyl-but-2-enyl)-piperidin-4-yl-amine (Ic)4-[(4-Benzyloxy-phenyl)-(3-methyl-but-2-enyl)-amino]-piperidine-1-carboxylic acid tert-butyl ester (5.0 g, 11.1 mmol) was dissolved in $CH_2Cl_2$ (20 mL) and treated with TFA (20 mL). The reaction was sired for 10 minutes, then concentrated in vacuo. The solution was washed with saturated bicarbonate solution (2×400 mL) and brine (1×400 mL), dried over $Na_2SO_4$, and concentrated in vacuo to give 3.9 g (99%) of the desired product as a pale oil.MS: 351 (M+1 for $C_{23}H_{30}N_2O_1$); TLC: $SiO_2$, $R_f$ 0.49 (10% MeOH/$CH_2Cl_2$).$^1$HNMR (CDCl$_3$, ppm): δ1.60 ((s, 3 H), 1.63 (s, 3 H), 1.65–1.75 (m, 2 H), 1.86 (d, 2 H, J=11.2 Hz), 2.75 (t, 2 H, J=12.5 Hz), 3.26 (d, 2 H, J=12.7 Hz), 3.41–3.49 (m, 1 H), 3.67 (d, 2 H, J=5.4 Hz), 4.97 (s, 2 H), 5.01–5.05 (m, 1 H), 6.73 (d, 2 H, J=9.3 Hz), 6.84 (d, 2 H, J=9.0 Hz), 7.26–7.40 (m, 5 H).

Step 4: The preparation of (S)-(1-{4-[(4-Benzyloxy-phenyl)-(3-methyl-but-2-enyl)-amino]-piperidine-1-carbonyl}-3-methyl-butyl)-carbamic acid tert-butyl ester(4-Benzyloxy-phenyl)-(3-methyl-but-2-enyl)-piperidin-4-yl-amine (Ic, 1.03 g, 2.94 mmol) was dissolved DMF (15 mL) and treated with Hunig's base (1.3 mL, 7.4 mmol), Boc-L-leucine hydrate (0.74 g, 2.94 mmol), and HBTU (1.11 g, 2.94 mmol). The reaction was stirred for 4.5 hours, then diluted with EtOAc (200 mL), washed with saturated bicarbonate solution and brine, dried over $Na_2SO_4$, and concentrated. The crude material was chromatographed on silica gel eluting with 5% (MeOH/$CH_2Cl_2$) to give 1.17 g (71%) of the desired product.MS: 565 (M+1 for $C_{34}H_{49}N_3O_4$); TLC $SiO_2$, $R_f$ 0.38 (8%MeOH/$CH_2Cl_2$).Analysis Calculated ($C_{29}H_{41}N_3O_2$): C 72.43, H 8.76, N 7.45. Found: C 72.08, H 9.00, N 7.33.

Step 5: The preparation of Example 20, (S)-2-Amino-1-{4-[(4-benzyloxy-phenyl)-(3-methyl-but-2-enyl)-amino]-piperidin-1-yl}-4-methyl-pentan-1-one(S)-(1-{4-[(4-Benzyloxy-phenyl)-(3-methyl-but-2-enyl)-amino]-piperidine-1-carbonyl}-3-methyl-butyl)-carbamic acid tert-butyl ester (1.07 g, 1.90 mmol) was dissolved in $CH_2Cl_2$ (4.5 mL) and treated with TFA (4.5 mL). The reaction was stirred for 25 minutes, then concentrated in vacuo. The residue was dissolved in EtOAc (175 mL) and solution was washed twice with saturated bicarbonate solution and brine, dried over $Na_2SO_4$, and concentrated in vacuo to give 0.87 g (99%) of the desired product as a pale oil.MS: 465 (M+1 for $C_{29}H_{41}N_3O_2$); TLC $SiO_2$, $R_f$ 0.31 (10% MeOH/$CH_2Cl_2$).Analysis Calculated ($C_{29}H_{41}N_3O_2O_2$.0.34 $H_2O$): C 74.13, H 8.94, N 8.95. Found: C 74.13, H 8.98, N 8.87.

EXAMPLE 21

(R)-2-Amino-1- {4-[(4-benzyloxy-phenyl)-(3-methyl-but-2-enyl)-amino]-piperidin-]-yl}-4-methyl-pentan-1-one was made in accordance with the methods of Example 20, except that BOC-D-leucine was used instead of BOC-L-Leucine in Step 4 and (R)-(1-{4-[(4-Benzyloxy-phenyl)-(3-methyl-but-2-enyl)-amino]-piperidine-1-carbonyl}-3-methyl-butyl)-carbamic acid tert-butyl ester was used instead of (S)-(1-

{4-[(4-Benzyloxy-phenyl)-(3-methyl-but-2-enyl)-amino]-piperidine-1-carbonyl}-3-methyl-butyl)-carbamic acid tert-butyl ester in Step 5.MS: 464 (M+ for $C_{29}H_{41}N_3O_2$); oil; TLC: $SiO_2$ $R_f$=0.15 (10% MeOH/EtOAc).Analysis Calculated ($C_{29}H_{41}N_3O_2.H_2O$): C 72.31, H 9.00, N 8.72. Found: C 72.50, H 8.75, N 8.79.

EXAMPLE 22

(S)-2-Amino-1-{4-[(4-benzyloxy-phenyl)-(3-methyl-but-2-enyl)-amino]-piperidin-1-yl}-3-methyl-pentan-1-one was made in accordance with the methods in Example 20, except that BOC-L-isoleucine was used instead of BOC-L-Leucine in Step 4 and (S)-(1-{4-[(4-Benzyloxy-phenyl)-(3-methyl-but-2-enyl)-amino]-piperidine-1-carbonyl}-2-methyl-butyl)-carbamic acid tert-butyl ester was used instead of (S)-(1-{4-[(4-Benzyloxy-phenyl)-(3-methyl-but-2-enyl)-amino]-piperidine-1-carbonyl}-3-methyl-butyl)-carbamic acid tert-butyl ester in Step 5.MS: 464 (M+ for $C_{29}H_{41}N_3O_2$); oil; TLC: $SiO_2$ $R_f$=0.15 (10% MeOH/EtOAc) ;Analysis Calculated ($C_{29}H_{41}N_3O_2.0.5H_2O$): C 73.69, H 8.95, N 8.89. Found: C 73.65, H 8.78, N 8.66.

EXAMPLE 23

(S)-1-{4-[(4-Benzyloxy-phenyl)-(3-methyl-but-2-enyl)-amino]-piperidin-1-yl}-2-dimethylamino-4-methyl-pentan-1-one Step 1: The preparation of (S)-2-(dimethyl-amino)-4-methyl-pentanoic acid(S)-2-amino-4-methyl-pentanoic acid (10.42 g, 80 mmol) was dissolved in $H_2O$ (120 mL) and treated with formaldehyde (80 mL, 37% solution), and Raney Nickel (2 g), and stirred for 21 hours. The solution was concentrated to a solid, dissolved in hot EtOH, boiled with charcoal, and filtered through Celite. The solution was allowed to cool. Acetone was added and the solution was placed in the refrigerator. The solution was filtered and the crystals were washed with acetone to give 9.7 g (77%) of (S)-2-(dimethyl-amino)-4-methyl-pentanoic acid.MS: 160 (M+1 for $C_8H_{17}N_1O_2$); TLC $SiO_2$, $R_f$ 0.04 (12% MeOH/$CH_2Cl_2$)

Step 2: The preparation of Example 23, (S)-1-{4-[(4-Benzyloxy-phenyl)-(3-methyl-but-2-enyl)-amino]-piperidin-1-yl}-2-dimethylamino-4-methyl-pentan-1-one was prepared by the method of Step 4 in Example 20 except that (S)-2-(dimethyl-amino)-4-methyl-pentanoic acid was used instead of Boc-L-leucine hydrate.MS: 492 (M+1 for $C_{31}H_{44}N_3O_2$); oil; TLC: $SiO_2$, $R_f$ 0.37 (5% MeOH/$CH_2Cl_2$) .Analysis Calculated ($C_{31}H44N_3O_2$): C 75.88, H 9.04, N 8.56. Found: C 75.56, H 9.44, N 8.39.

EXAMPLE 24

(S)-1-{-4-[(4-Benzyloxy-phenyl)-(3-methyl-but-2-enyl)-amino]-piperidin-1-yl}-2-isopropylamino-4-methyl-pentan-1-oneA solution of (S)-2-Amino-1-{4-[(4-benzyloxy-phenyl)-(3-methyl-but-2-enyl)-amino]-piperidin-1-yl}-4-methyl-pentan-1-one (Example 20) (0.20 g, 0.43 mmol) and acetone (25 mg, 0.43 mmol) in $CH_2Cl_2$ (4 mL) was cooled to 0° C., treated with NaBH(OAc)$_3$, allowed to warm to room temperature as ice melted and stir overnight. The reaction was diluted with EtOAc (100 mL), washed with saturated sodium bicarbonate solution and brine, dried over $Na_2SO_4$, and concentrated. The residue was chromatographed on silica gel eluting with 5% MeOH/$CH_2Cl_2$ to give 176 mg (81%) of the desired product.MS: 507 (M+1 for $C_{32}H_{47}N_3O_2$); TLC: $SiO_2$, $R_f$ 0.33 (5% MeOH/$CH_2Cl_2$).Analysis Calculated ($C_{32}H_{47}N_3O_2$): C 76.00, H 9.37, N 8.31. Found: C 75.78, H 9.33, N 8.12.

EXAMPLE 25

(S)-1-{4-[(4-Benzyloxy-phenyl)-(3-methyl-but-2-enyl)-amino]-piperidin-1-yl}-4-methyl-2-(3-methyl-butylamino)-pentan-1-one was made in accordance with the methods of Example 24, except that isovaleraldehyde was used instead of acetone.MS: 534 (M+1 for $C_{34}H_{50}N_3O_2$); TLC: $SiO_2$, $R_f$ 0.33 (5% MeOH/$CH_2Cl_2$).Analysis Calculated ($C_{34}H_{50}N_3O_2$): C 76.65, H 9.46, N 7.89. Found: C 76.32, H 9.71, N 7.77.

EXAMPLE 26

(S)-1-{4-[(4-Benzyloxy-phenyl)-(3-methyl-but-2-enyl)-amino-piperidin-1-yl}-2-cyclohexylamino-4-methyl-pentan-1-one was made in accordance with the methods of Example 24, except that cyclohexanone was used instead of acetone.MS: 547 (M+1 for $C_{35}H_{51}N_3O_2$); TLC: $SiO_2$, $R_f$ 0.32 (5% MeOH/$CH_2Cl_2$);Analysis Calculated ($C_{35}H_{51}N_3O_2$): C 77.02, H 9.42, N 7.70. Found: C 76.77, H 9.43, N 7.47.

EXAMPLE 27

(S)-1-{-4-[(4-Benzyloxy-phenyl)-(3-methyl-but-2-enyl)-amino]-piperidin-1-yl}-4-methyl-2-[(1H-pyrrol-2-ylmethyl)-amino]-pentan-1-one was made in accordance with the methods of Example 24, except that pyrrole-2-carboxaldehyde was used instead of acetone.MS: 542 (M+1 for $C_{34}H_{44}N_4O_2$); TLC: $SiO_2$, $R_f$ 0.30 (5% MeOH/$CH_2Cl_2$).

EXAMPLE 28

(S)-Azepane-1-carboxylic acid {1-[4-(4-benzyloxy-phenylamino)-piperidine-1-carbonyl]-3-methyl-butyl}-amide Scheme XIV

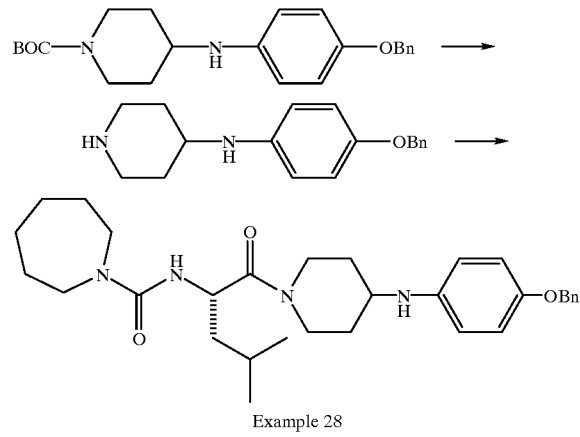

Example 28

Step 1: The preparation of 4-(4-Benzyloxy-phenylamino)-piperidine-1-carboxylic acid tert-butyl ester was made in accordance with the methods in Example 20 (Step 1).

Step 2: The preparation of 4-(4-Benzyloxy-phenylamino)-piperidineA solution of 4-(4-benzyloxy-phenylamino)-piperidine-1-carboxylic acid tert-butyl ester (3 g, 7.84 mmol) in $CH_2Cl_2$ (20 mL) was treated with TFA (20 mL) and stirred for 30 minutes. The reaction was concentrated, diluted with EtOAc, washed with saturated sodium bicarbonate solution and brine, dried over $Na_2SO_4$, and concentrated to give 1.56 g of the desired product. MS: 283 (M+1 for $C_{18}H_{22}N_2O_1$); TLC: $SiO_2$, $R_f$ 0.31 (10% MeOH/$CH_2Cl_2$) .Analysis Calculated ($C_{18}H_{22}N_2O_1$): C: 61.65, H: 7.13, N: 7.77. Found: C: 61.26, H: 7.08, N: 7.68.

Step 3: The preparation of (S)-2-[(Azepane-1-carbonyl)-amino]-4-methyl-pentanoic acid Step i: The preparation of (S)-2-[(Azepane-1-carbonyl)-amino]-4-methyl-pentanoic acid benzyl esterA solution of triphosgene (15.7 g, 52.9 mmol) in $CH_2Cl_2$ (600 mL) was cooled to –10° C. The solution was treated dropwise with a solution of H-Leu-OBn (28.1 g, 127 mmol) and pyridine (26 mL, 320 mmol) in $CH_2Cl_2$ (150 mL). The reaction was stirred at –10° C. for 90 minutes and then treated with a solution of hexamethyleneimine (22 mL, 380 mmol) in $CH_2Cl_2$ (75 mL). The solution was stirred for 48 hours at room temperature. The reaction mixture was concentrated and the residue was dissolved in ether and washed with 1N HCl solution, water, and saturated aqueous $CuSO_4$ solution. The organic layer was dried over $MgSO_4$, treated with activated charcoal, and filtered. The filtrate was concentrated to 1/2 volume and treated with hexane. The resulting suspension was stored overnight at –10° C. The solid was collected by filtration, washed with hexane, and dried under vacuum to give 38.6 g (88%) of the desired product as a white solid.MS: 347 (M+1for $C_{20}H_{30}N_2O_3$); TLC: $SiO_2$, $R_f$ 0.2 (2:1 hexane/EtOAc).

Step ii: The preparation of (S)-2-[(Azepane-1-carbonyl)-amino]-4-methyl-pentanoic acidA solution of (S)-2-[(Azepane-1-carbonyl)-amino]-4-methyl-pentanoic acid benzyl ester (8.97 g, 25.9 mmol) in THF (100 mL) was hydrogenated at 50 psi over Pd/C (0.25 g, 20% Pd) for 16 hours. The reaction mixture was filtered through Celite and concentrated to dryness. The residue was heated in hexane (50 mL). The resulting suspension was cooled and the solid collected by filtration and washed with hexane. The solid was dried at room temperature under vacuum to give 6.1 g (92%) of the desired product as a white solid.MS: 258 (M+1 for $C_{13}H_{24}N_2O_3$); mp 88–89° C.

Step 4: The preparation of Example 28, (S)-Azepane-1-carboxylic acid {1-[4-(4-benzyloxy-phenylamino)-piperidine-1-carbonyl]-3-methyl-butyl}-amideA solution of 4-(4-benzyloxy-phenylamino)-piperidine (0.564 g, 2 mmol) in DMF (8 mL) was treated with (S)-2-[(Azepane-1-carbonyl)-amino]-4-methyl-pentanoic acid (0.51 g, 2 mmol), diisopropylethylamine (0.5 g, 4 mmol), and HBTU (0.76 g, 2 mmol). The reaction was stirred at room temperature, then diluted with EtOAc, washed with saturated sodium bicarbonate solution and brine, dried over $Na_2SO_4$, and concentrated to give 1.1 g of Example 28.MS: 521 (M+1 for $C_{31}H_{44}N_4O_3$); TLC: $SiO_2$, $R_f$ 0.25 (EtOAc).Analysis Calculated ($C_{31}H_{44}N_4O_3$): C: 69.11 H: 8.61, N: 10.40. Found: C: 68.75, H: 8.29, N: 10.68.

EXAMPLE 29

(S)-Azepane-1-carboxylic acid (1-{4-[(4-benzyloxy-phenyl)-2-methylbutyl-amino]-piperidine-1-carbonyl}-3-methyl-butyl)-amide(S)-Azepane-1-carboxylic acid {1-[4-(4-benzyloxy-phenylamino)-piperidine-1-carbonyl]-3-methyl-butyl}-amide (Example 28) (0.30 g, 0.28 mmol) was dissolved in $CH_2Cl_2$ (5 mL) and treated with isovaleraldehyde (62 μL, 0.58 mmol). The reaction was stirred for 30 minutes at RT, then cooled to 0° C., treated with $NaBH(OAc)_3$, allowed to warm to room temperature as the ice melted and stir overnight. The reaction was then diluted with EtOAc (100 mL), washed with saturated bicarbonate solution and brine, dried over $Na_2SO_4$, and concentrated. The residue was chromatographed on silica gel eluting with 3:2 hexane/EtOAc to give 0.28 g (82%) of the desired product. MS: 592 (M+1 for $C_{36}H_{54}N_4O_3$); TLC: $SiO_2$, $R_f$ 0.28 (3:2 EtOAc/hexane).Analysis Calculated ($C_{36}H_{54}N_4O_3$) C: 72.74, H: 9.22, N: 9.42. Found: C: 72.76, H: 9.24, N: 9.33.

EXAMPLE 30(S)-Azepane-1-carboxylic acid (1-{4-[(benzyloxy-phenyl)-ethyl-amino]-piperidine-1-carbonyl}-3-methyl-butyl)-amide was made in accordance with the methods in Example 29, except that acetaldehyde was used instead of isovaleraldehyde.MS: 550 (M+1 for $C_{33}H_{48}N_4O_3$); TLC: $SiO_2$, $R_f$ 0.39 (4:1 EtOAc/hexane).Analysis Calculated ($C_{33}H_{48}N_4O_3 \cdot 0.25H_2O$) C: 71.64, H: 8.84, N: 10.13. Found: C: 71.47, H: 9.02, N: 10.03.

EXAMPLE 31(S)-Azepane-1-carboxylic acid (1-{4-[benzyl-(4-benzyloxy-phenyl)-amino]-piperidine-1-carbonyl}-3-methyl-butyl)-amide was made in accordance with the methods in Example 29, except that benzaldehyde was used instead of isovaleraldehyde.MS: 612 (M+1 for $C_{38}H_{50}N_4O_3$); TLC: $SiO_2$, $R_f$ 0.52 (6% MeOH/$CH_2Cl_2$).Analysis Calculated ($C_{38}H_{50}N_4O_3 \cdot 0.25H_2O$) C: 74.72, H: 8.25, N: 9.17. Found: C: 74.41, H: 8.42, N: 8.84.

EXAMPLE 32Azepane-1-carboxylic acid (1-{4-[(4-benzyloxy-phenyl)-(3-hydroxy-butyl)-amino]-piperidine-1-carbonyl}-3-methyl-butyl)-amide was made in accordance with the methods in Example 29, except that 3-hydroxybutyraldehyde was used instead of isovaleraldehyde. MS: 594 (M+1 for $C_{35}H_{52}N_4O_4$); TLC: $SiO_2$, $R_f$ 0.52 (8% MeOH/$CH_2Cl_2$).Analysis Calculated ($C_{35}H_{52}N_4O_4 \cdot 0.25H_2O$) C: 69.64, H: 8.88, N: 9.28. Found: C: 69.53, H: 8.72, N: 9.16.

EXAMPLE 33

(S)-{4-[(1-2-[(Azepane-1-carbonyl)-amino]-4-methyl-pentanoyl}-piperidin-4-yl)-(3-methyl-but-2-enyl)-amino]-phenyl}-carbamic acid benzyl ester Scheme XV

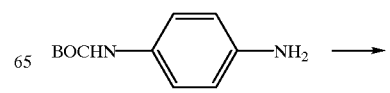

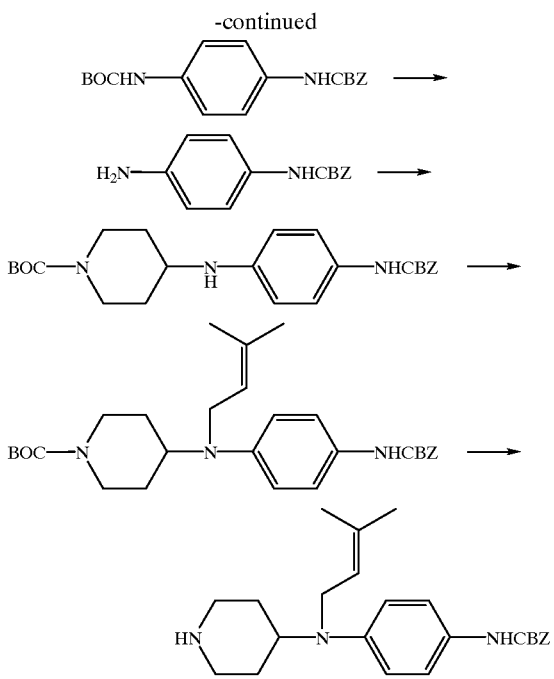

Step 1: The preparation of (4-tert-Butoxycarbonylamino-phenyl)-carbamic acid benzyl esterN-Boc-1,4-phenylenediamine (1.0 g, 4.8 mmol) was dissolved in THF (24 mL). Pyridine (1.94 mL, 24 mmol) was added, the reaction was cooled to 0° C., benzyl chloroformate (0.82 mL, 5.8 mmol) was added, and the reaction was stirred cold for 3 hours. The reaction was diluted with EtOAc (200 mL), washed with saturated sodium bicarbonate solution and brine, dried over $Na_2SO_4$, and concentrated. The crude material was chromatographed on silica gel eluting with 3% MeOH/CH2Cl2 to give 0.82 g (50%) of the desired product. MS: 343 (M+1 for $C_{19}H_{22}N_2O_4$); TLC: $SiO_2$, $R_f$ 0.30 (5% $MeOH/CH_2Cl_2$). Analysis Calculated ($C_{19}H_{22}N_2O_4 \cdot 0.29H_2O$) C: 65.65, H: 6.55, N: 8.06. Found: C: 65.65, H: 6.54, N: 7.98.

Step 2: The preparation of (4-Amino-phenyl)-carbamic acid benzyl ester(4-tert-Butoxycarbonylamino-phenyl)-carbamic acid benzyl ester (0.74 g, 2.16 mmol) was dissolved in $CH_2Cl_2$ (5 mL) and treated with TFA (5 mL). The reaction was stirred for 20 minutes, then diluted with EtOAc (125 mL), washed twice with saturated sodium bicarbonate solution and once with brine, dried over $Na_2SO_4$, and concentrated to give the desired product. MS: 243 (M+1 for $C_{14}H_{14}N_2O_2$); TLC: $SiO_2$, $R_f$ 0.17 (5% $MeOH/CH_2Cl_2$). Analysis Calculated ($C_{14}H_{14}N_2O_2$) C: 69.41, H: 5.82, N: 11.56. Found: C: 69.76, H: 5.82, N: 11.43.

Step 3: The preparation of 4-(4-benzyloxycarbonyloxy-phenylamino)-piperidine-1-carboxylic acid tert-butyl ester (4-Amino-phenyl)-carbamic acid benzyl ester (0.42 g, 1.73 mmol) was dissolved in $CH_2Cl_2$ (10 mL), treated with Boc-4-piperidone, stirred 30 minutes, then cooled to 0° C. and treated with $NaBH(OAc)_3$. The reaction was allowed to warm to room temperature as the ice melted and stir overnight. The reaction was diluted with EtOAc (100 mL), washed with saturated sodium bicarbonate solution and brine, dried over $Na_2SO_4$, and concentrated. The residue was chromatographed on silica gel eluting with 3:2 hexane/EtOAc to give 0.61 g (83%) of the desired product. MS: 426 (M+1 for $C_{24}H_{31}N_3O_4$); TLC: $SiO_2$, $R_f$ 0.43 (3:2 hexane/EtOAc). Analysis Calculated ($C_{24}H_{31}N_3O_4$): C: 67.74, H: 7.34, N: 9.87. Found: C: 67.35, H: 7.41, N: 9.62.

Step 4: The preparation of 4-[(4-Benzyloxycarbonylamino-phenyl)-(3-methyl-but-2-enyl)-amino]-piperidine-1-carboxylic acid tert-butyl ester4-(4-Benzyloxycarbonylamino-phenylamino)-piperidine-1-carboxylic acid tert-butyl ester (0.55 g, 1.29 mmol) was dissolved in THF (10 mL), treated with Hunig's base (1.1 mL, 6.46 mmol), and 4-bromo-2-methyl-2-butene (0.3 mL, 2.59 mmol), then heated to 40° C. overnight. The reaction was concentrated, then chromatographed on silica gel eluting with 3:1 hexane/EtOAc to give 0.51 g (80%) of the desired product. MS: 496 (M+1 for $C_{24}H_{39}N_3O_4$); TLC: $SiO_2$, $R_f$ 0.34 (3:1 hexane/EtOAc).

Step 5: The preparation of (4-Benzyloxycarbonylamino-phenyl)-(3-methyl-but-2-enyl)-piperidin-4-yl-amine4-[(4-Benzyloxycarbonylamino-phenyl)-(3-methyl-but-2-enyl)-amino]-piperidine-1-carboxylic acid tert-butyl ester (0.5 g, 1.0 mmol) was dissolved in $CH_2Cl_2$ (4 mL) and treated with TFA (4 mL). The reaction was stirred 25 minutes, then concentrated, redissolved in EtOAc (100 mL), washed twice with saturated sodium bicarbonate solution and brine, dried over $Na_2SO_4$, and concentrated to give 0.39 g (98%) of the desired product. MS: 396 (M+1 for $C_{24}H_{31}N_3O_2$); TLC: $SiO_2$, $R_f$ 0.30 (10% $MeOH/CH_2Cl_2$).

Step 6: The preparation of Example 33, (S)-{4-[(1-{2-[(Azepane-1-carbonyl)-amino]-4-methyl-pentanoyl}-piperidin-4-yl)-(3-methyl-but-2-enyl)-amino-1-phenyl}-carbamic acid benzyl ester(4-Benzyloxycarbonylamino-phenyl)-(3-methyl-but-2-enyl)-piperidin-4-yl-amine (0.35 g, 0.88 mmol) was dissolved in DMF (8 mL), treated with Hunig's base (0.47 mL, 2.64 mmol), (S)-2-[(azepane-1-carbonyl)-amino]-4-methyl-pentanoic acid (0.21 g, 0.88 mmol), and HBTU (0.34 g, 0.88 mmol). The reaction was stirred 2 hours, then diluted with EtOAc (100 mL), washed with saturated sodium bicarbonate solution and brine, dried over $Na_2SO_4$, and concentrated. The residue was chromatographed on silica gel eluting with 5% $MeOH/CH_2Cl_2$ to give 0.49 g (93%) of the desired product. MS: 633 (M+1 for $C_{37}H_{53}N_5O_4$); TLC: SiO, $R_f$ 0.30 (5% $MeOH/CH_2Cl_2$). Analysis Calculated ($C_{35}H_{52}N_4O_4 \cdot 0.5H_2O$) C: 69.32, H: 8.49, N: 10.93. Found: C: 69.32, H: 8.20, N: 10.89.

EXAMPLE 34

(S)-{4-[(1-{2-[(Azepane-1-carbonyl)-amino]-4-methyl-pentanoyl}-piperidin-4-yl)-(3-methyl-butyl)-amino]-phenyl}-carbamic acid benzyl ester Scheme XVI

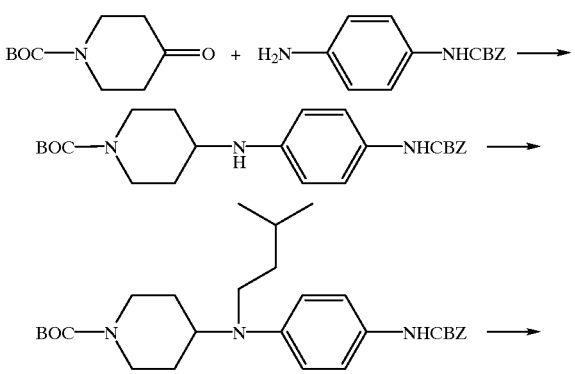

-continued

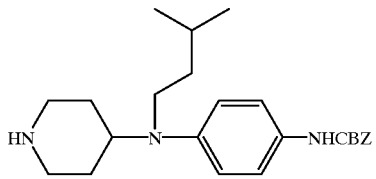

Step 1: 4-(4-benzyloxycarbonylamino-phenylamino)-piperidine-1-carboxylic acid tert-butyl ester was prepared according to the methods of Example 33 (Steps 1–3).

Step 2: The preparation of 4-[(4-Benzyloxycarbonylamino-phenyl)-(3-methyl-butyl)-amino]-piperidine-1-carboxylic acid tert-butyl ester4-(4-Benzyloxycarbonylamino-phenylamino)-piperidine-1-carboxylic acid tert-butyl ester (3.0 g, 7.05 mmol) was dissolved in $CH_2Cl_2$ (60 mL), treated with isovaleraldehyde (0.76 mL, 7.05 mmol), and stirred at room temperature for 30 minutes. The reaction was cooled to 0° C., treated with $NaBH(OAc)_3$ (2.24 g, 10.58 mmol) and allowed to warm to room temperature and stir overnight. The reaction was diluted with EtOAc (300 mL), washed with saturated bicarbonate solution and brine, dried over $Na_2SO_4$, and concentrated. The residue was chromatographed on silica gel eluting with 3:1 hexane/EtOAc to give 3.0 g (86%) of the desired product.MS: 497 (M+1 for $C_{29}H_{41}N_5O_4$); TLC: $SiO_2$, $R_f$ 0.37 (3:1 hexane/EtOAc).

Step 3: The preparation of (4-Benzyloxycarbonylamino-phenyl)-(3-methyl-butyl)-piperidin-4-yl-amine4-[(4-Benzyloxycarbonylamino-phenyl)-(3-methyl-butyl)-amino]-piperidine-1-carboxylic acid tert-butyl ester (3.0 g, 6.05 mmol) was dissolved in $CH_2Cl_2$ (15 mL), treated with TFA (15 mL), and stirred for 15 minutes. The reaction was concentrated, diluted with EtOAc (200 mL), washed twice with saturated bicarbonate solution and brine, dried over $Na_2SO_4$, and concentrated to give 2.23 g of the desired product.MS: 397 (M+1 for $C_{24}H_{33}N_5O_2$); TLC: $SiO_2$, $R_f$ 0.24 (10% $MeOH/CH_2Cl_2$).

Step 4: Preparation of Example 34, (S)-{4-[(1-2-[(Azepane-1-carbonyl)-amino]-4-methyl-pentanoyl}-piperidin-4-yl)-(3-methyl-butyl)-amino]-phenyl}-carbamic acid benzyl ester(4-Benzyloxycarbonylamino-phenyl)-(3-methyl-butyl)-piperidin-4yl-amine (0.22 g, 5.64 mmol) was dissolved in DMF (30 mL), treated with Hunig's base (3.93 mL, 22.6 mmol), (S)-2-[(Azepane-1-carbonyl)-amino]-4-methyl-pentanoic acid (1.36 g, 5.64 mmol), and HBTU (2.04 g, 5.64 mmol), and stirred for 1 hour. The reaction was diluted with EtOAc (200 mL), washed with saturated bicarbonate solution and brine, dried over $Na_2SO_4$, and concentrated. The residue was chromatographed on silica gel eluting with 5% $MeOH/CH_2Cl_2$ to give 2.76 g (77%) of the desired product.MS: 635 (M+1 for $C_{37}H_{55}N_5O_4$); TLC: $SiO_2$, $R_f$ 0.34 (5% $MeOH/CH_2Cl_2$).Analysis Calculated ($C_{37}H_{55}N_5O_4 \cdot 0.25H_2O$): C: 69.62, H: 8.76, N: 10.97. Found: C: 69.62, H: 8.71,N: 10.96.

EXAMPLE 35

(S)-Azepane-1-carboxylic acid (1-{4-[(4-amino-phenyl)-(3-methyl-butyl)-amino]-piperidine-1-carbonyl}-3-methyl-butyl)-amide[(S)-{4-[(1-{2-[(Azepane-1-carbonyl)-amino]-4-methyl-pentanoyl}-piperidin-4-yl)-(3-methyl-butyl)-amino]-phenyl}-carbamic acid benzyl ester] (Example 34, 2.75 g, 4.34 mmol) was dissolved in THF/MeOH (50 mL, 1:1), treated with 20% Pd/C (0.26 g), and shaken under $H_2$ (49 psi) for 1.25 hours. The reaction was filtered through Celite and concentrated to give 2.01 g (93%) of the desired product.MS: 501 (M+1 for $C_{29}H_{49}N_5O_2$); TLC: $SiO_2$, $R_f$ 0.27 (5% $MeOH/CH_2Cl_2$).

EXAMPLE 36

(S)-Azepane-1-carboxylic acid (1-{4-[[4-(3,3-dimethyl-butylamino)-phenyl]-(3-methyl-butyl-amino]-piperidine-1-carbonyl}-3-methyl-butyl)-amide(S)-Azepane-1-carboxylic acid (1-{4-[(4amino-phenyl)-(3-methyl-butyl)-amino]-piperidine-1-carbonyl}-3-methyl-butyl)-amide (Example 35, 0.25 g, 0.50 mmol) was dissolved in $CH_2Cl_2$ (4 mL), treated with isovaleraldehyde (63 µL, 0.50 mmol), and stirred for 30 minutes. The reaction was cooled to 0° C., treated with $NaBH(OAc)_3$ (0.16 g, 0.75 mmol), and allowed to warm to room temperature and stir overnight. The reaction was diluted with EtOAc (100 mL), washed with saturated bicarbonate solution and brine, dried over $Na_2SO_4$, and concentrated. The residue was chromatographed on silica gel eluting with 4% to 5% $MeOH/CH_2Cl_2$ to give the desired product.MS: 585 (M+1 for $C_{35}H_{61}N_5O_2$); TLC: $SiO_2$, $R_f$ 0.29 (5% $MeOH/CH_2Cl_2$). HPLC (1:1 $CH_3CN/H_2O$ with 0.5% TFA, C-18 column) RT=13.63 min, 100% pure.

EXAMPLE 37

(S)-Azepane-1-carboxylic acid (1-{4-[[4-(cyclohexylmethyl-amino)-phenyl]-(3-methyl-butyl)-amino-piperidine-1-carbonyl}-3-methyl-butyl)-amide was made in accordance with the methods of Example 36, except that cyclohexane-carboxaldehyde was used instead of 3,3-methylbutyraldehyde. MS: 597 (M+1 for $C_{36}H_{61}N_5O_2$); TLC: $SiO_2$, $R_f$; HPLC (1:1 $CH_3CN/H_2O$ with 0.5% TFA, C-18 column) RT=21.81 min, 100% pure.

EXAMPLE 38

(S)-Azepane-1-carboxylic acid (1-{4-[[4-(3-hydroxy-butylamino)-phenyl]-(3-methyl-butyl)-amino]-piperidine-1-carbonyl}-3-methyl-butyl)-amide was made in accordance with the methods of Example 36, except that 3-hydroxybutyraldehyde was used instead of 3,3-dimethylbutyraldehyde.MS: 573 (M+1 for $C_{33}H_{57}N_5O_3$); TLC: $SiO_2$, $R_f$ 0.18 (5% $MeOH/CH_2Cl_2$).Analysis Calculated ($C_{33}H_{57}N_5O_3$): C: 69.31, H: 10.05, N: 12.25. Found: C: 69.43, H: 9.96, N: 12.11.

EXAMPLE 39

(S)-Azepane-1-carboxylic acid (1-{4-[(4-benzylamino-phenyl)-(3-methyl-butyl)-amino]-piperidine-1-carbonyl}-3-methyl-butyl)-amide: was made in accordance with the methods of Example 36, except that benzaldehyde was used instead of 3,3-dimethylbutyraldehyde.MS: 591 (M+1 for $C_{36}H_{55}N_5O_2$); TLC: $SiO_2$, $R_f$ 0.33 (5% $MeOH/CH_2Cl$

EXAMPLE 40

(S)-Azepane-1-carboxylic acid {3-methyl-1-[4-((3-methyl-butyl)-{4-[(pyridin-2-ylmethyl)-amino]-phenyl}-amino)-piperidine-1-carbonyl]-butyl}-amide was made in accordance with the methods of Example 36, except that pyridine-2carboxaldehyde was used instead of 3,3-dimethylbutyraldehyde.MS: 592 (M+1 for $C_{35}H_{54}N_6O_2$); TLC: $SiO_2$, $R_f$ 0.30 (5% $MeOH/CH_2Cl_2$).

EXAMPLE 41

(S)-Azepane-1-carboxylic acid (1-{4-[[4-(4-dimethylamino-benzylamino)-phenyl]-(3-methyl-butyl)-amino]-piperidine-1-carbonyl}-3-methyl-butyl)-amide was made in accordance with the methods of Example 36, except that N,N-dimethylaminobenzaldehyde was used instead of 3,3-dimethylbutyraldehyde. MS: 634 (M+1 for $C_{38}H_{60}N_6O_2$); TLC: $SiO_2$, $R_f$ 0.32 (6% $MeOH/CH_2Cl_2$).

EXAMPLE 42

(S)-Azepane-1-carboxylic acid (1-{4-[[4-(4-hydroxy-benzylamino)-phenyl]-(3-methyl-butyl)-amino]-piperidine-1-carbonyl}-3-methyl-butyl)-amide was made in accordance with the methods of Example 36, except that 4-hydroxy-benzaldehyde was used instead of 3,3-dimethylbutyraldehyde.MS: 607 (M+1 for $C_{36}H_{55}N_5O_3$); TLC: $SiO_2$, $R_f$ 0.21 (5% $MeOH/CH_2Cl_2$).

EXAMPLE 43

(S)-Azepane-1-carboxylic acid (1-{4-[[4-(1-hydroxy-cyclohexylethynyl)-phenyl]-(3-methyl-but-2-enyl)-amino]-piperidine-1-carbonyl}-3-methyl-butyl)-amide Scheme XVII

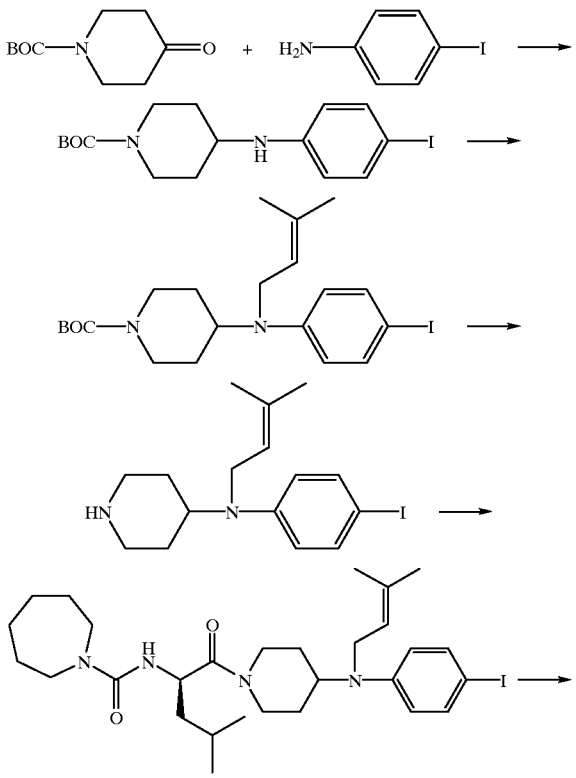

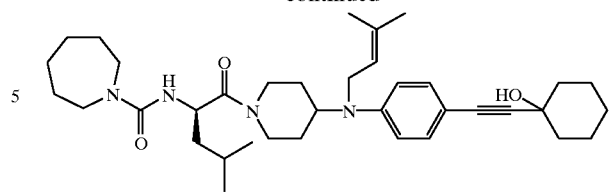

Example 43

Step 1: The preparation of 4-(4-iodo-phenylamino)-piperidine-1-carboxylic acid tert-butyl ester4-iodoaniline (10.0 g, 45.7 mmol) was dissolved in $CH_2Cl_2$ (250 mL), treated with Boc-4-piperidone (9.11 g, 45.7 mmol), and stirred for 30 minutes. The reaction was cooled to 0° C., $NaBH(OAc)_3$ (14.54 g, 68.6 mmol) was added, and the reaction was allowed to warm to room temperature as the ice melted and stir overnight. The reaction was diluted with $CH_2Cl_2$ (250 mL), washed three times with saturated sodium bicarbonate solution and once with brine, dried over $Na_2SO_4$, and concentrated to give the desired product.MS: 403 (M+1 for $C_{16}H_{23}N_2O_2I_1$); TLC: $SiO_2$, $R_f$ 0.38 (2:1 hexane/EtOAc).

Step 2: The preparation of 4-[(4-Iodo-phenyl)-(3-methyl-but-2-enyl)-amino]-piperidine-1-carboxylic acid tert-butyl ester4-(4-Iodo-phenylamino)-piperidine-1-carboxylic acid tert-butyl ester (5.0 g, 12.4 mmol) was dissolved in THF (62 mL), treated with Hunig's base (8.6 mL, 49.6 mmol) and 4-bromo-2-methyl-2-butene (2.9 mL, 24.8 mmol), then heated to 40° C. overnight. An additional 0.3 equivalents of the bromide and Hunig's base were added and the reaction was heated for another 6 hours, then concentrated. The crude material was chromatographed on silica gel eluting with 5:1 hexane/EtOAc to give 3.76 g (65%) of the desired productMS: 471 (M+1 for $C_{21}H_{31}N_2O_2I_1$); TLC: $SiO_2$, $R_f$ 0.65 (2.5:1 hexane/EtOAc).

Step 3: The preparation of (4-Iodo-phenyl)-(3-methyl-but-2-enyl)-piperidin-4-yl-amine4-[(4-Iodo-phenyl)-(3-methyl-but-2-enyl)-amino]-piperidine-1-carboxylic acid tert-butyl ester (3.46 g, 7.36 mmol) was dissolved in $CH_2Cl_2$ (13 mL) and treated with TFA (13 mL). The reaction was stirred for 15 minutes, then concentrated in vacuo, dissolved in EtOAc (200 mL), washed two times with saturated sodium bicarbonate solution and once with brine, dried over $Na_2SO_4$, and concentrated to give the desired product.MS: 371 (M+1 for $C_{16}H_{23}N_2I_1$); TLC: $SiO_2$, $R_f$ 0.52 (10% $MeOH/CH_2Cl_2$).

Step 4: The preparation of (S)-Azepane-1-carboxylic acid (1-{4-[(4-iodo-phenyl)-(3-methyl-but-2-enyl)-amino]-piperidine-1-carbonyl}-3-methyl-butyl)-amide was made in accordance with the Example 28 (Step 4), except that (4-Iodo-phenyl)-(3-methyl-but-2-enyl)-piperidin-4-yl-amine was used instead of 4-(4-Benzyloxy-phenylamino)-piperidine.MS: 610 (M+1 for $C_{29}H_{45}N_4O_2I_1$); TLC: $SiO_2$, $R_f$ 0.28 (5% $MeOH/CH_2Cl_2$).Analysis Calculated ($C_{29}H_{45}N_4O_2I_1$): C: 57.23, H: 7.45, N: 9.21. Found: C: 57.15, H: 7.59, N: 8.86.

Step 5: The preparation of Example 43(S)-Azepane-1-carboxylic acid (1-{4-[(4-iodo-phenyl)-(3-methyl-but-2-enyl)-amino]-piperidine-1-carbonyl}-3-methyl-butyl)-amide (0.50 g, 0.49 mmol) was dissolved in THF (4 mL), treated with triethylamine (0.34 mL, 2.45 mmol), 1-ethynyl-1-cyclohexanol (94 μL, 0.74 mmol), $Pd(Ph_3P)_2Cl_2$ (34 mg, 0.049 mmol), and cuprous iodide (4.8 mg, 0.028 mmol). The reaction was stirred overnight at room temperature, then heated to 40° C. overnight. Another 1.5 equivalents of the acetylene, 0.1 equivalents of $Pd(Ph_3P)_2Cl_2$, and 0.05 equivalents of cuprous iodide were added and the reaction was

EXAMPLE 44

(S)-2-Amino-1-{4-[(4-benzyloxy-phenyl)-(3-methyl-butyl)-amino]-piperidin-1-yl}-4-methyl-pentan-1-one Step 1: The preparation of 4-(4-Benzyloxy-phenylamino)-piperidine-1-carboxylic acid tert-butyl ester was prepared according to the procedure in Example 20 (Step 1)

Step 2: The Preparation of 4-[(4-Benzyloxy-phenyl)-(3-methyl-butyl)-amino]-piperidine-1-carboxylic acid tert-butyl ester4-(4-Benzyloxy-phenylamino)-piperidine-1-carboxylic acid tert-butyl ester (3.0 g, 7.84 mmol) was dissolved in $CH_2Cl_2$ (50 mL), treated with isovaleraldehyde (0.84 mL, 7.84 mmol), and stirred 30 minutes. The reaction was cooled to 0° C., then treated with $NaBH(OAc)_3$ (2.49 g, 11.77 mmol) and allowed to warm to room temperature and stir overnight. The reaction was diluted with EtOAc (400 mL), washed with saturated sodium bicarbonate solution and brine, dried over $Na_2SO_4$, and concentrated. The residue was chromatographed on silica gel eluting with 5% MeOH/ $CH_2Cl_2$ to give 3.3 g of the desired product.MS: 454 (M+1 for $C_{28}H_{40}N_2O_3$); TLC: $SiO_2$, $R_f$ 0.47 (6% MeOH/$CH_2Cl_2$) .Analysis Calculated ($C_{28}H_{40}N_2O_3$): C: 74.30, H: 7.8.91, N: 9.6.19. Found: C: 74.34, H: 9.08, N: 6.04.

Step 3: The preparation of (4-Benzyloxy-phenyl)-(3-methyl-butyl)-piperidin-4yl-amine 4-[(4-Benzyloxy-phenyl)-(3-methyl-butyl)-amino]-piperidine-1-carboxylic acid tert-butyl ester (3.27 g, 7.22 mmol) was dissolved in $CH_2Cl_2$ (25 mL), treated with TFA (25 mL), and stirred for 30 minutes. The reaction was concentrated, diluted with EtOAc (300 mL), washed twice with saturated sodium bicarbonate solution and brine, dried over $Na_2SO_4$, and concentrated to give 2.62 g of the desired product.MS: 354 (M+1 for $C_{23}H_{32}N_2O_1$); TLC: $SiO_2$, $R_f$ 0.60 (10% MeOH/$CH_2Cl_2$).

Step 4: The preparation of (S)-(1-{4-[(4-Benzyloxy-phenyl)-(3-methyl-butyl)-amino]-piperidine-1-carbonyl}-3-methyl-butyl)-carbamic acid tert-butyl ester was made in accordance with the methods of Example 20 (Step 4), except that (4-Benzyloxy-phenyl)-(3-methyl-butyl)-piperidin-4-yl-amine was used instead of (4-Benzyloxy-phenyl)-(3-methyl-but-2-enyl)-piperidin-4-yl-amineMS: 566 (M+ for $C_{34}H_{51}N_3O_4$); oil; TLC: $SiO_2$ $R_f$=0.8 (50% hexanes/EtOAc).

Step 5: Example 44 was made in accordance with the methods of Example 20 (Step 5), except that (S)-(1-{4-[(4-Benzyloxy-phenyl)-(3-methyl-butyl)-amino]-piperidine-1-carbonyl}-3-methyl-butyl)-carbamic acid tert-butyl ester was used instead of (S)-(1-{4-[(4-Benzyloxy-phenyl)-(3-methyl-but-2-enyl)-amino]-piperidine-1-carbonyl}-3-methyl-butyl)-carbamic acid tert-butyl ester.MS: 466 (M+ for $C_{29}H_{43}N_3O_2$); oil; TLC: $SiO_2$ $R_f$=0.15 (10% MeOH/EtOAc).Analysis Calculated ($C_{29}H_{43}N_3O_2 \cdot 0.5H_2O$): C 73.38, H 9.36, N 8.85. Found: C 73.11, H 9.13, N 8.75.

EXAMPLE 45

(S,R/S)-2-Amino-1-{3-[(4-benzyloxy-phenyl)-(3-methyl-but-2-enyl)-amino]-piperidin-1-yl}-4-methyl-pentan-1-one Scheme XVIII

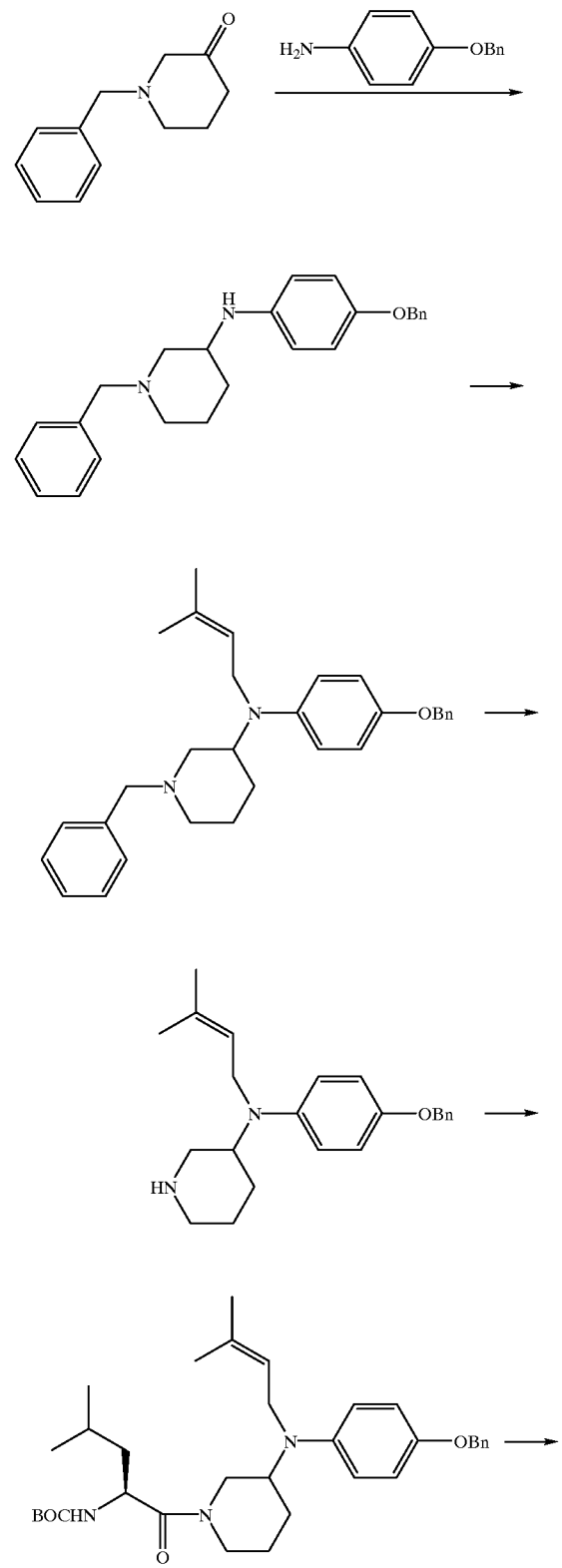

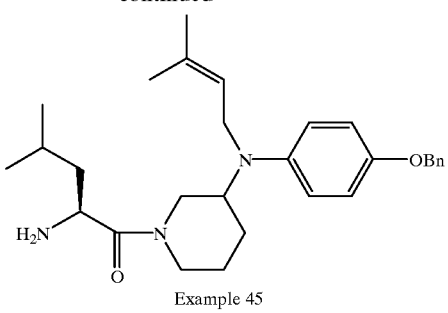

Example 45

Step 1: (4-Benzyloxy-phenyl)-(1-benzyl-piperidin-3-yl)-amine was prepared in accordance with the procedures in Example 20 (Step 1) except that 1-benzyl-3-piperidone was used instead of 1-Boc-4-piperidone.MS: 373 (M+1 for $C_{25}H_{28}N_2O_1$); TLC: $SiO_2$ $R_f$ 0.6 (5% $MeOH/CH_2Cl_2$). Analysis Calculated ($C_{25}H_{28}N_2O_1$): C 79.84, H 7.61, N 7.45. Found: C 79.83, H 7.56, N 7.45.

Step 2: The preparation of (4-Benzyloxy-phenyl)-(1-benzyl-piperidin-3-yl)-(3-methyl-but-2-enyl)-amine was prepared in accordance with the procedure in Example 20 (Step 2) except that (4-Benzyloxy-phenyl)-(1-benzyl-piperidin-3-yl)-amine was used instead of 4-(4-Benzyloxy-phenylamino)-piperidine-1-carboxylic acid tert-butyl ester.MS: 441 (M+1 for $C_{30}H_{36}N_2O_1$); oil; TLC: SiO2 $R_f$=0.5 (66% hexanes/EtOAc).Analysis Calculated ($C_{30}H_{36}N_2O_1$): C 81.78, H 8.24, N 6.36. Found: C 81.81, H 8.26, N 6.31.

Step 3: The preparation of (4-Benzyloxy-phenyl)-(1-piperidin-3-yl)-(3-methyl-but-2-enyl)-amine(4-Benzyloxy-phenyl)-(1-benzyl-piperidin-3-yl)-(3-methyl-but-2-enyl)-amine (0.90 g, 2.04 mmol) was dissolved in 1,2-dichloroethane (20 mL), cooled to 0° C., and treated with α-chloroethylchloroformate (0.24 mL, 2.04 mmol). The reaction was stirred cold for 15 minutes, then heated to 60° C. for 1 hour. The reaction was cooled to room temperature, concentrated in vacuo, re-dissolved in MeOH (20 mL), heated to 50° C. for 1 hour, then concentrated in vacuo to give 0.86 g (>100%) of the crude material which was carried on without further purification.MS: 351 (M+1 for $C_{23}H_{30}N_2O$); oil; TLC: $SiO_2$ $R_f$=0.1 (10% $MeOH/CH_2Cl_2$).

Step 4: The preparation of (S,R/S)-(1-{3-[(4-Benzyloxy-phenyl)-(3-methyl-but-2-enyl)-amino]-piperidine-1-carbonyl}-3-methyl-butyl)-carbamic acid tert-butyl ester was made in accordance with the methods in Example 20 (Step 4), except that (4-Benzyloxy-phenyl)-(1-piperidin-3-yl)-(3-methyl-but-2-enyl)-amine was used instead of (4-Benzyloxy-phenyl)-(1-piperidin-4-yl)-(3-methyl-but-2-enyl)-amine.MS: 564 (M+ for $C_{34}H_{49}N_3O_4$); oil; TLC: $SiO_2$ $R_f$=0.5 (6% $MeOH/CH_2Cl_2$).

Step 5: Example 45 was made in accordance with the methods of Example 20 (Step 5), except (S,R/S)-(1-{3-[(4-Benzyloxy-phenyl)-(3-methyl-but-2-enyl)-amino]-piperidine-1-carbonyl}-3-methyl-butyl)-carbamic acid tert-butyl ester was used instead (S)-(1-{4-[(4-Benzyloxy-phenyl)-(3-methyl-but-2-enyl)-amino]-piperidine-1-carbonyl}-3-methyl-butyl)-carbamic acid tert-butyl ester.MS: 464 (M+ for $C_{29}H_{41}N_3O_2$); oil; TLC: $SiO_2$ $R_f$=0.5 (10% $MeOH/CH_2Cl_2$).Analysis Calculated ($C_{29}H_{41}N_3O_2$): C 75.12, H 8.91, N 9.06. Found: C 74.85, H 9.05, N 8.77.

EXAMPLE 46

(S,R/S)-Azepane-1-carboxylic acid (1{-3-[(4-benzyloxy-phenyl)-(3-methyl-but-2-enyl)-amino]-piperidine-1-carbonyl}-3-methyl-butyl)-amide was made in accordance with the methods of Example 45 (Step 4), except that (S)-2-[(Azepane-1-carbonyl)-amino]-4-methyl-pentanoic acid was used instead of Boc-L-leucine.MS: 589 (M+1 for $C_{36}H_{52}N_4O_3$); oil; TLC: $SiO_2$ $R_f$=0.3 (5% $MeOH/CH_2Cl_2$).

EXAMPLE 47

(S)-[1-(2-Amino-4-methyl-pentyl)-piperidin-4-yl]-(4-benzyloxy-phenyl)-(3-methyl-but-2enyl)-amine Scheme XIX

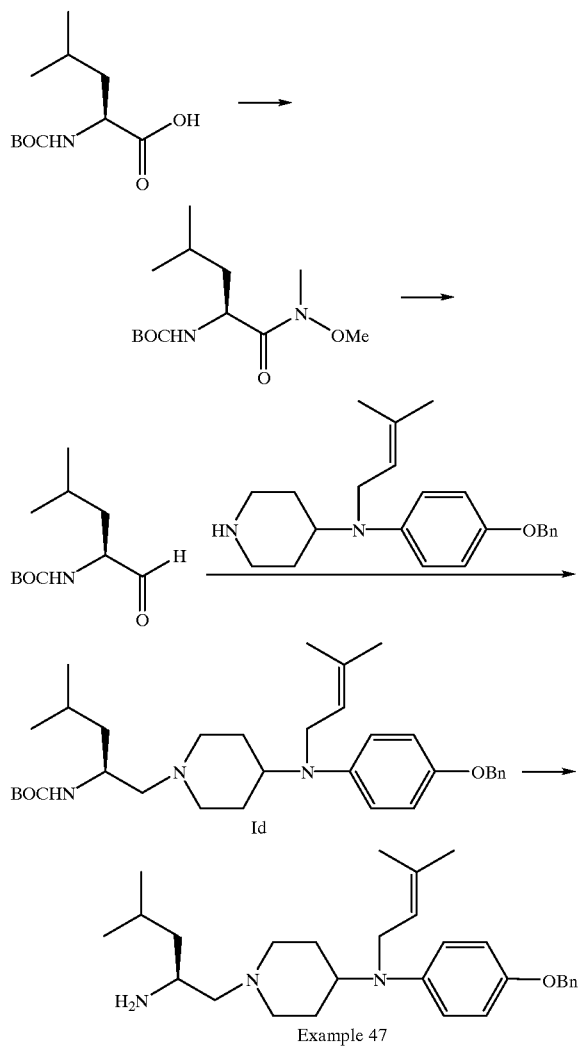

Example 47

Step 1: The preparation of Boc-L-Leucine-N-methyl-N-methoxy amideBoc-L-leucine hydrate (10.0 g, 40.0 mmol) was dissolved in DMF (200 mL), treated with Hunig's base (21 mL, 120 mmol), O,N-dimethylhydroxylamine hydrochloride salt (3.9 g, 40 mmol), and HBTU (15.16 g, 40 mmol), and stirred for 1 hour. The reaction was diluted with EtOAc (1 L), washed with saturated bicarbonate solution and brine, dried over $Na_2SO_4$, and concentrated to give 12.2 g of the desired product as a pale oil.MS: 278 (M+1 for $C_{13}H_{29}N_2O_4$); oil; TLC: $SiO_2$ $R_f$=0.54 (10% $MeOH/CH_2Cl_2$).

Step 2: Preparation of Boc-L-leucinalBoc-L-Leucine-N-methyl-N-methoxy amide (1.0 g, 3.64 mmol) was dissolved in $Et_2O$ (36 mL) and cooled in a brine-ice bath. $LiAlH_4$ (0.138 g, 3.64 mmol) was added and the reaction was stirred cold. The reaction was quenched by dropwise addition of a solution of sodium thiosulfate (0.5 g) in H₂O (16 mL). Water (100 mL) was added and the aqueous layer was extracted with Et₂O (3×100 mL). The organic layer was washed with 1N HCl, saturated bicarbonate solution, and brine, dried over Na₂SO₄, and concentrated. The crude material was carried on immediately without further purification.

Step 3: The preparation of (S)-[1-(2-Amino-4-methyl-pentyl)-piperidin-4-yl]-(4-benzyloxy-phenyl)-(3-methyl-but-2-enyl)-amine, Example 47:

Step i: Boc-L-leucinal (0.78 g, 3.64 mmol) was treated with a solution of (4-Benzyloxy-phenyl)-(3-methyl-but-2-enyl)-piperidin-4-yl-amine (1.28 g, 3.64 mmol) in CH₂Cl₂ (36 mL), stirred 15 minutes, cooled to 0° C., and treated with NaBH(OAc)₃ (1.16 g, 5.46 mmol). The reaction was allowed to warm to RT as ice melted and stir 4 hours. The reaction was diluted with EtOAc (200 mL), washed with saturated bicarbonate solution, and brine, dried over Na₂SO₄, and concentrated. The residue was chromatographed on silica gel eluting with 8% MeOH/CH₂Cl₂ to give 1.15 g (57%) of the desired product (Id).MS: 550 (M+1 for C₃₄H₅₁N₃O₃); TLC: SiO₂ R$_f$=0.5 (10% MeOH/CH₂Cl₂) .Analysis Calculated (C₃₄H₅₁N₃O₃): C: 74.28, H: 9.35, N: 7.64. Found: C: 73.94, H: 9.42, N: 7.58.

Step ii: The preparation of Example 47To a solution of Id (0.57 g, 1.04 mmol) in CH₂Cl₂ (10 mL) was added TFA (7 mL). The reaction was stirred for 40 minutes, then concentrated in vacuo. The residue was dissolved in EtOAc (175 mL) and solution was washed twice with saturated bicarbonate solution and brine, dried over Na₂SO₄, and concentrated in vacuo. The residue was chromatographed on silica gel eluting with 8% MeOH/CH₂Cl₂ to give 0.39 g (83%) of the title compound, which contained 0.3 mol of trifluoroacetic acid. MS: 450 (M+1 for C₂₉H₄₃N₃O₁); TLC SiO₂, R$_f$ 0.4 (10% MeOH/CH₂Cl₂).Analysis Calculated (C₂₉H₄₃N₃O₁.0.3 CF₃CO₂H): C 73.47, H 9.02, N 8.68. Found: C 73.40, H 8.70, N 8.74.

EXAMPLE 48

(S)-2-Amino-1-{4-[(4-(4-fluorobenzyloxy)-phenyl)-(3-methyl-butyl)-amino]-piperidin-1-yl}-4-methyl-pentan-1-one

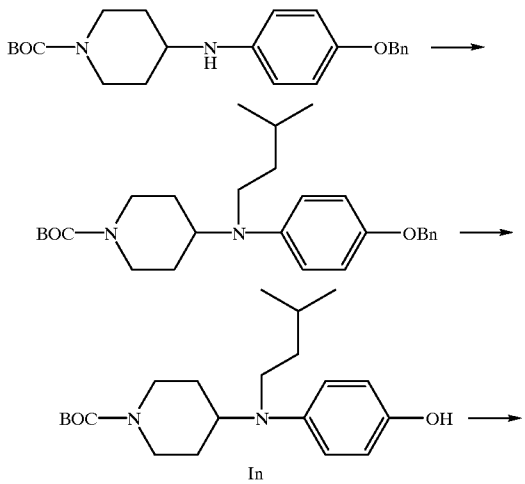

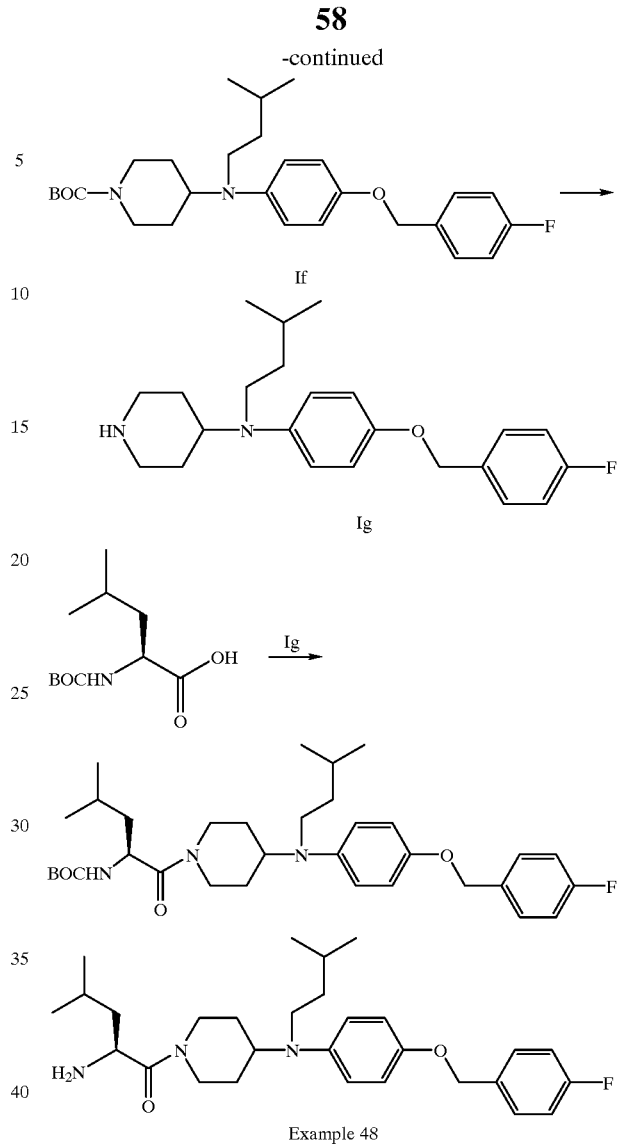

Example 48

Step 1: Preparation of 4-[(4-benzyloxy-phenyl)-(3-methyl-butyl)-amino]-piperidine-1-carboxylic acid tert-butyl ester 4-(4-Benzyloxy-phenylamino)-piperidine-1-carboxylic acid tert-butyl ester (9.51 g, 24.9 mmol) was dissolved in CH₂Cl₂ (150 mL) and treated with isovaleraldehyde (2.7 mL, 24.9 mmol). The reaction was stirred for 30 minutes, then cooled to 0° C., treated with NaBH(OAc)₃, allowed to warm to room temperature as the ice melted, and stir overnight. The reaction was diluted with CH₂Cl₂ (300 mL), washed twice with saturated sodium bicarbonate solution and once with brine, dried over Na₂SO₄, and concentrated. The crude material was chromatographed on silica gel eluting with 4% MeOH/CH₂Cl₂ to give 9.59 g (85%) of the desired product.MS: 454 (M+1 for C₂₈H₄₀N₂O₃); TLC: SiO₂, R$_f$ 0.48 (5% MeOH/CH₂Cl₂)

Step 2: Preparation of 4-[(4-hydroxy-phenyl)-(3-methyl-butyl)-amino]-piperidine-1-carboxylic acid tert-butyl ester (In)4-[(4-Benzyloxy-phenyl)-(3-methyl-butyl)-amino]-piperidine-1-carboxylic acid tert-butyl ester (9.59 g, 21.2 mmol) was dissolved in 1:1 THF/MeOH (100 mL), treated with 20% Pd/C (1.0 g), and shaken under an atmosphere of H₂ (47 psi) for 15 hours. The reaction was filtered and the solution was concentrated. The crude material was chromatographed on silica gel eluting with 4:1 hexane/EtOAc to give 6.3 g (82%) of the desired product.MS: 364 (M+1 for $C_{21}H_{34}N_2O_3$); TLC: $SiO_2$, $R_f$ 0.37 (8% MeOH/$CH_2Cl_2$)

Step 3: Preparation of 4-fluorobenzyl methanesulfonate (Ie) 4-Fluorobenzyl alcohol (1.73 mL, 15.9 mmol) was dissolved in $CH_2Cl_2$ (80 mL), treated with Hunig's base (11.1 mL, 63.6 mmol), cooled to 0° C., and treated with methanesulfonyl chloride (1.35 mL, 17.4 mmol). The reaction was allowed to warm to room temperature as the ice melted and stir for 1 hour, then diluted with EtOAc (200 mL) washed with saturated sodium bicarbonate solution and with brine, dried over $Na_2SO_4$, and concentrated to give 3.3 g (102%) of the crude product which was used immediately without further purification.TLC: $SiO_2$, $R_f$ 0.39 (2:1 hexane/EtOAc)

Step 4: Preparation of 4-{[4-(4-fluorobenzyloxy)-phenyl]-(3-methyl-butyl)-amino}-piperidine-1-carboxylic acid tert-butyl ester (If)4-[(4-hydroxy-phenyl)-(3-methyl-butyl)-amino]-piperidine-1-carboxylic acid tert-butyl ester (In, 1.18 g, 3.26 mmol) was dissolved in DMF (7 mL), treated with NaH (0.26 g, 6.52 mmol, 60% dispersion in mineral oil), and stirred for 8 minutes. 4-Fluorobenzyl methanesulfonate (Ie, 0.93 g, 4.56 mmol) was added and the reaction was stirred for 5 minutes, then diluted with EtOAc (100 mL), washed with saturated sodium bicarbonate solution and with brine, dried over $Na_2SO_4$, and concentrated. The residue was chromatographed on silica gel eluting with 4:1 hexane/EtOAc to give 1.39 g (91%) of the desired product.MS: 472 (M+1 for $C_{28}H_{39}N_2O_3F_1$); TLC $SiO_2$, $R_f$ 0.31 (4:1 hexane/EtOAc)

Step 5: Preparation of [4-(4-Fluorobenzyloxy)-phenyl]-(3-methyl-butyl)-piperidin-4-amine (Ig)4-{[4-(4-fluorobenzyloxy)-phenyl]-(3-methyl-butyl)-amino}-piperidine-1-carboxylic acid tert-butyl ester (If, 1.80 g, 3.82 mmol) was dissolved in $CH_2Cl_2$ (12 mL), treated with TFA (12 mL), and stirred for 20 minutes. The reaction was concentrated and placed under vacuum for 20 minutes, then diluted with EtOAc (200 mL), washed twice with saturated sodium bicarbonate solution and once with brine, dried over $Na_2SO_4$, and concentrated to give 0.89 g (74%) of the desired product.MS: 371 (M+1 for $C_{23}H_{31}N_2O_1F_1$); TLC: $SiO_2$, $R_f$ 0.34 (10% MeOH/$CH_2Cl_2$)

Step 6: Preparation of (S)-(1-{4-[(4-(4-fluorobenzyloxy-phenyl))-(3-methyl-butyl)-amino]-piperidine-1-carbonyl}-3-methyl-butyl)-carbamic acid tert-butyl ester[4-(4-Fluorobenzyloxy)-phenyl]-(3-methyl-1-butyl)-piperidin-4-yl-amine (Ig, 0.20 g, 0.54 mmol) was dissolved in DMF (5 mL), and treated with Hunig's (0.38 mL, 2.2 mmol), Boc-Leucine hydrate (0.134 g, 0.54 mmol), and HBTU (0.205 g, 0.54 mmol). The reaction was stirred overnight, then diluted with EtOAc (100 mL), washed twice with saturated sodium bicarbonate solution and once with brine, dried over $Na_2SO_4$, and concentrated to give 0.36 g (113%) of the crude product which was used without further purification. MS: 585 (M+1 for $C_{34}H_{50}N_3O_4F_1$); TLC: $SiO_2$, $R_f$ 0.42 (5% MeOH/$CH_2Cl_2$)

Step 7: Preparation of Example 48(S)-(1-{4-[(4-(4-Fluorobenzyloxy-phenyl))-(3-methyl-butyl)-amino]-piperidine-1-carbonyl}-3-methyl-butyl)-carbamic acid tert-butyl ester (0.36 g, 0.62 mmol) was dissolved in 2 mL $CH_2Cl_2$, treated with TFA (2 mL), and stirred for 20 minutes. The reaction was concentrated, diluted with EtOAc (100 mL), washed twice with saturated sodium bicarbonate solution and once with brine, dried over $Na_2SO_4$, and concentrated. The residue was chromatographed on silica gel eluting with 10% MeOH/$CH_2Cl_2$ to give 0.198 g (66%) of the title product MS: 485 (M+1 for $C_{29}H_{42}N_3O_2F_1$); TLC: $SiO_2$, $R_f$ 0.29 (10% MeOH/$CH_2Cl_2$).Analysis Calculated ($C_{29}H_{42}N_3O_2F_1$.0.1$H_2O$): C: 71.75, H: 8.76, N: 8.66 Found: C: 71.41, H: 8.31, N: 8.36.

EXAMPLE 49

(S)-[1-(2-Amino-4-methyl-pentyl)-piperidin-4-yl]-[4-(4-fluorobenzyloxy)-phenyl]-(3-methyl-butyl)-amine

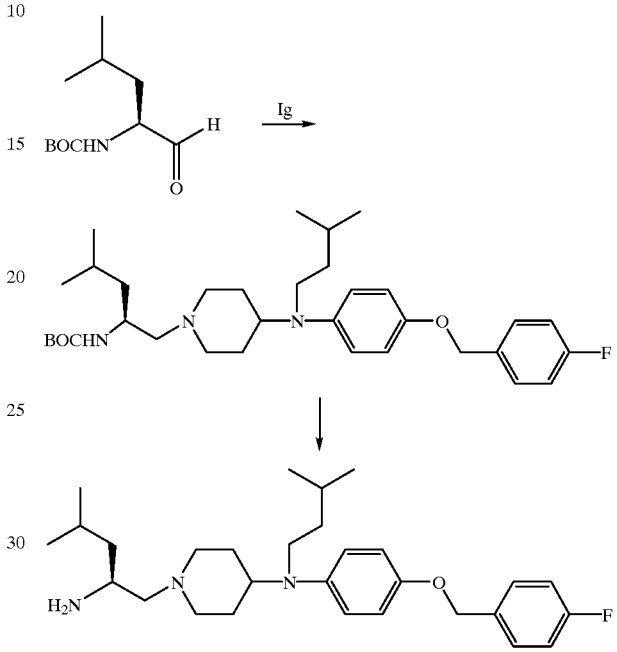

Example 49 was made in accordance with the method of Example 47 (Step 3) except that [4-(4-fluorobenzyloxy)-phenyl]-(3-methyl-butyl)-piperidin-4-yl-amine (Ig) was used instead of (4-benzyloxy-phenyl)-(3-methyl-but-2-enyl)-piperidin-4-yl-amine. MS: 377 (M+1 for $C_{29}H_{44}N_3O_1F_1$); TLC: $SiO_2$, $R_f$ 0.38 (12% MeOH/$CH_2Cl_2$). HPLC 100% pure, retention time=3.662 min. (1:1 $CH_3CN/H_2O$ with 0.5% TFA, C-18 column).

EXAMPLE 50

(S)-2-Amino-1-{4-[(4-phenethyl-phenyl)-(3-methyl-but-2-enyl)-amino]-piperidin-1-yl}-4-methyl-pentan-1-one

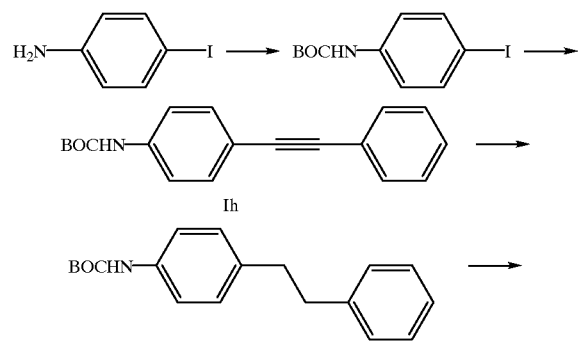

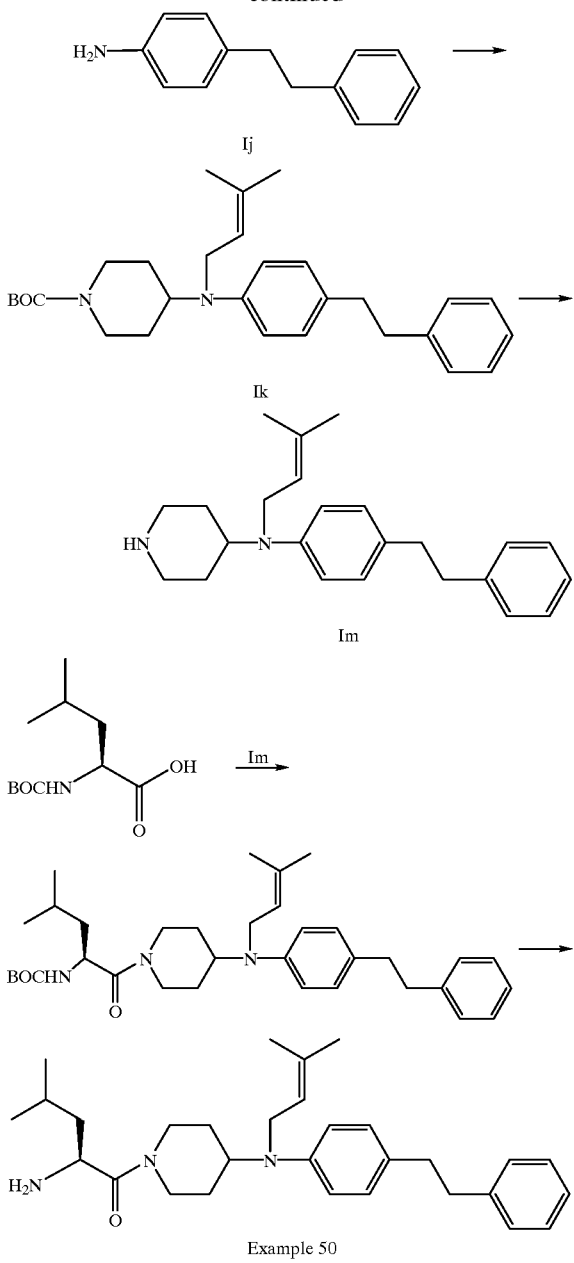

Example 50

Step 1: Preparation of (4-iodo-phenyl)-carbamic acid tert-butyl 4-Iodoaniline (5.0 g, 22.8 mmol) was placed in an amber flask, dissolved in THF (25 mL), cooled to 0° C., and treated with Boc anhydride (5.48 g, 25.1 mmol). The reaction was heated to 60° C. overnight, then concentrated, diluted with EtOAc (300 mL), washed with saturated sodium bicarbonate solution and once with brine, dried over $Na_2SO_4$, and concentrated to give 7.1 g (98%) of the desired product.
MS: 320 (M+1 for $C_{11}H_{14}N_1O_2I_1$); TLC: $SiO_2$, $R_f$ 0.38 (12% MeOH/$CH_2Cl_2$)

Step 2: Preparation of (4-phenylethynyl-phenyl)-carbamic acid tert-butyl ester (Ih)(4-Iodo-phenyl)-carbamic acid tert-butyl ester (2.0 g, 6.27 mmol) was dissolved in THF (50 mL), treated with triethylamine (4.4 mL, 31.4 mmol), phenylacetylene (1.03 mL, 9.40 mmol), cuprous iodide (0.06 g, 0.31 mmol), and $Pd(Ph_3)_2Cl_2$ (0.44 g, 0.63 mmol). The reaction was stirred overnight, then filtered and concentrated. The crude material was chromatographed on silica gel eluting with 7:1 hexane/EtOAc to give 1.48 g (80%) of the desired product.MS: 294 (M+1 for $C_{19}H_{19}N_1O_2$); TLC: $SiO_2$, $R_f$ 0.58 (6:1 hexane/EtOAc).

Step 3: Preparation of (4-phenethyl-phenyl)-carbamic acid tert-butyl ester (Ii)(4-Phenylethynyl-phenyl)-carbamic acid tert-butyl ester (Ih, 0.95 g, 3.24 mmol) was dissolved in MeOH (50 mL), treated with 20% Pd/C (0.1 g), and shaken under $H_2$ (50 psi) for 22 hours. The reaction was filtered and concentrated to give 0.90 g (93%) of the desired productMS: 298 (M+1 for $C_{19}H_{23}N_1O_2$); TLC: $SiO_2$, $R_f$ 0.34 (6:1 hexane/EtOAc).

Step 4: Preparation of 4-phenethyl-phenylamine(Ij):(4-Phenethyl-phenyl)-carbamic acid tert-butyl ester (Ii, 0.90 g, 3.03 mmol) was dissolved in $CH_2Cl_2$ (15 mL) and treated with TFA (15 mL). The reaction was stirred for 20 minutes, concentrated, diluted with EtOAc (200 mL), washed twice with saturated sodium bicarbonate solution and once with brine, dried over $Na_2SO_4$, and concentrated to give 0.56 g (94%) of the desired product.MS: 198 (M+1 for $C_{14}H_{15}N_1$); $SiO_2$, $R_f$ 0.50 (10% MeOH/$CH_2Cl_2$).

Step 5: Preparation of 4-[(4-phenethyl-phenyl)-(3-methyl-but-2-enyl)-amino]-piperidine-1-carboxylic acid tert-butyl eater (Ik) was made in accordance with Example 20 (Steps 1 and 2), except 4-phenethyl-phenylamine(Ij) was used instead of 4-benzyloxyaniline hydrochloride salt.MS: 450 (M+1 for $C_{29}H_{40}N_2O_2$); TLC: $SiO_2$, $R_f$ 0.50 (5:1 hexane/EtOAc);Analysis Calculated ($C_{29}H_{40}N_2O_2 \cdot 0.15H_2O$): C: 77.17, H: 9.00, N: 6.21. Found: C: 77.19, H: 9.00, N: 6.17.

Step 6: Preparation of (4-phenethyl-phenyl)-(3-methyl-but-2-enyl)-piperidin-4yl-amine (Im) was made in accordance with Example 20 (Step 3), except that 4-[(4-phenethyl-phenyl)-(3-methyl-but-2-enyl)-amino]-piperidine-1-carboxylic acid tert-butyl eater (Ik) was used instead of 4-[(4-benzyloxy-phenyl)-(3-methyl-but-2-enyl)-amino]-piperidine-1-carboxylic acid tert-butyl eater (Ib).MS: 350 (M+1 for $C_{29}H_{40}N_2O_2$); TLC: $SiO_2$, $R_f$ 0.25 (10% MeOH/$CH_2Cl_2$).

Step 7: Preparation of (S)-(1-{4-[(4-phenethyl-phenyl)-(3-methyl-but-2-enyl)-amino]-piperidine-1-carbonyl}-3-methyl-butyl)-carbamic acid tert-butyl ester was made in accordance with the method of Example 20 (Step 4), except that (4-phenethyl-phenyl)-(3-methyl-but-2-enyl)-piperidin-4-yl-amine (Im) was used instead of (4-benzyloxy-phenyl)-(3-methyl-but-2-enyl)-piperidin-4-yl-amine.MS: 563 (M+1 for $C_{35}H_{51}N_3$—$O_3$); TLC: $SiO_2$, $R_f$ 0.43 (5% MeOH/$CH_2Cl_2$).Calculated Analysis ($C_{35}H_{51}N_3O_3$) C: 74.83, H: 9.15, N: 7.48. Found: C: 74.53, H: 8.97, N: 7.35.

Step 8: Preparation of Example 50 was made in accordance with the method in Example 20 (Step 5), except that (S)-(1-{4-[(4-phenethyl-phenyl)-(3-methyl-but- 2-enyl)-amino]-piperidine-1-carbonyl}-3-methyl-butyl)-carbamic acid tert-butyl ester was used instead of (S)-(1-{4-[(4-benzyloxy-phenyl)-(3-methyl-but-2-enyl)-amino]-piperidine-1-carbonyl}-3-methyl-butyl)-carbamic acid tert-butyl ester.MS: 463 (M+1 for $C_{30}H_{43}N_3O1$); TLC: $SiO_2$, $R_f$ 0.38 (10% MeOH/$CH_2Cl_2$). HPLC 100% pure, retention time=3.835 min (1:1 $CH_3CH/H_2O$ with 0.5% TFA, C-18 column).

EXAMPLE 51

(S)-Azepane-1-carboxylic acid (1-{4-[(4-phenethyl-phenyl)-(3-methyl-but-2-enyl)-amino]-piperidine-1-carbonyl}-3-methyl-butyl)-amide

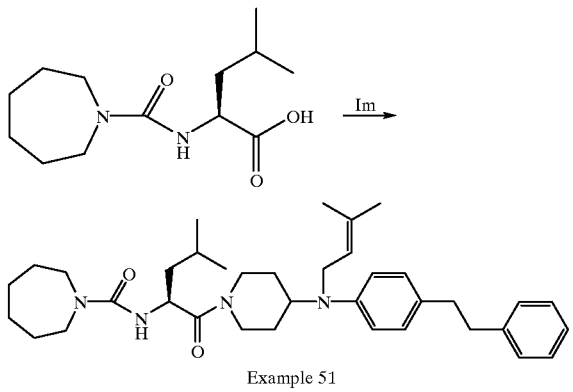

Example 51 was made in accordance with the methods of Example 45 (Step 4), except that (S)-2-[(Azepane-1-carbonyl)-amino]-4-methyl-pentanoic acid was used instead of Boc-L-leucine and (4-phenethyl-phenyl)-(3-methyl-but-2-enyl)-1-piperidin-4-yl-amine (Im) was used instead of (4-benzyloxy-phenyl)-(1-piperidin-3-yl)-(3-methyl-but-2-enyl)-amine.MS: 588 (M+1 for $C_{37}H_{54}N_{34}O_2$); TLC: $SiO_2$, $R_f$ 0.38 (5% $MeOH/CH_2Cl_2$).Analysis Calculated ($C_{37}H_{54}N_{34}O_2 \cdot 0.88H_2O$). C: 73.80, H: 9.32, N: 9.30. Found: C: 74.17, H: 8.97, N: 8.93.

Biological ActivityThe compounds of the present invention exhibit valuable biological properties because of their ability to block calcium flux through N-type voltage-gated calcium channels. To measure interaction at the N-type $Ca^{2+}$ channel and calcium flux inhibition, the effects of the compounds of the present invention were measured in the assays described below.

Measurement of N-type $Ca^{2+}$ Channel Blocking Potencies of Compounds in IMR-32 Cells Using the Fluorescent $Ca^{2+}$ Indicator Indo-1IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 μM nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

MethodsThe IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimycotic mixture (Gibco). At approximately 80% confluency, differentiation was induced by the addition of 1 mM dibutyryl cAMP and 2.5 μM bromodeoxyuridine to the medium. After 7 to 13 days of differentiation, cells were detached using 0.5 mM EDTA and loaded with 5 μM Indo-1 acetoxymethyl ester (Molecular Probes, Eugene, Oreg.) at 30° C. for 45 minutes. Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostated cuvette holder with stirring capabilities as well as with a computer-controlled pump which allowed for reagent addition during measurement Instrument control and data collection was done by PTI's OSCAR software running on an IBM compatible computer. Different concentrations of the test compounds (60 μL in dimethyl sulfoxide) were added to 5.94 mL of assay buffer containing approximately $3 \times 10^6$ loaded cells, and 5 μM Nitrendipine (in 30 μL EtOH) to block L-type $Ca^{2+}$ channels. Samples were incubated for 10 minutes at 30° C. and then aliquoted into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 μL of stimulation solution (1M KCl, 68 mM $CaCl_2$) to the cuvette via the computer-controlled pump. Ratio of dual emission signals (400 nm/490 nm), which is proportional to intracellular $Ca^{2+}$ concentration, was plotted against time, and the difference between maximal response after stimulation and basal value before stimulation) was determined. Values obtained in this way were plotted as a function of drug concentration. $IC_{50}$ values of test compounds were calculated by fitting a four-parameter logistic function to the data using the least squares method.

In Vivo Biological ProtocolA compound of the present invention was dissolved in water using 10% (weight/volume) Emulphor (GAF Corp., Wayne, N.J.) surfactant. Substances were administered by intravenous injection into the retro-orbital venous sinus. All testing was performed 15 minutes or 45 minutes after drug injection. All the male mice, 3–4 weeks old were obtained from Jackson Laboratories Bar Harbour, Me. Immediately before anticonvulsant testing, mice were placed upon a wire mesh, 4 inches square suspended from a steel rod. The square was slowly inverted through 180 degrees and mice observed for 30 seconds. Any mouse falling from the wire mesh was scored as ataxia.Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15–20 seconds.The incidence of all the seizure phases in the drug-treated and vehicle-treated mice was recorded, and the occurrence of tonic seizures were used for calculating anti-convulsant $ED_{50}$ values by probit analysis. Mice were used only once for testing at each time and dose point. Results of this assay are shown below in Table 2.

TABLE 1

| Example Number | IMR 32<br>% of Blockade @ μM |
|---|---|
| 1 | IC$_{50}$ = 0.26 |
| 2 | 50% @ 1 |
| 3 | IC$_{50}$ = 0.69 |
| 4 | IC$_{50}$ = 0.75 |
| 5 | IC$_{50}$ = 0.5 |
| 6 | IC$_{50}$ = 0.84 |
| 7 | IC$_{50}$ = 1.9 |
| 8 | 76% @ 10, 55% @ 1 |
| 9 | IC$_{50}$ = 1.6 |
| 10 | 82% @ 10, 54% @ 1 |
| 11 | 91% @ 10, 49% @ 1 |
| 12 | IC$_{50}$ = 0.63 |
| 13 | IC$_{50}$ = 5.6 |
| 14 | 86% @ 10, 36% @ 1 |
| 15 | 65% @ 3, 21% @ 0.3 |
| 16 | 86% @ 10, 36% @ 1 |
| 17 | 80% @ 10, 57% @ 1 |
| 18 | 71% @ 10, 67% @ 1 |
| 19 | 70% @ 10, 74% @ 1 |
| 20 | IC$_{50}$ = 2.4 μM |
| 21 | 92% @ 10 μM, 43% @ 1 μM |
| 22 | 90% @ 10 μM, 39% @ 1 μM |
| 23 | IC$_{50}$ = 0.65 μM |
| 24 | IC$_{50}$ = 0.75 μM |
| 25 | IC$_{50}$ = 0.48 μM |
| 26 | IC$_{50}$ = 0.51 μM |
| 27 | IC$_{50}$ = 0.39 μM |
| 28 | IC$_{50}$ = 2.5 μM |
| 29 | IC$_{50}$ = 0.19 μM |
| 30 | IC$_{50}$ = 0.33 μM |
| 31 | IC$_{50}$ = 0.43 μM |
| 32 | IC$_{50}$ = 4.6 μM |
| 33 | IC$_{50}$ = 0.17 μM |
| 34 | 83% @ 1 μM |
| 35 | IC$_{50}$ = 2.2 μM |
| 36 | IC$_{50}$ = 0.18 μM |
| 37 | IC$_{50}$ = 0.29 μM |
| 38 | IC$_{50}$ = 1.8 μM |
| 39 | IC$_{50}$ = 0.4 μM |
| 40 | IC$_{50}$ = 1.1 μM |
| 41 | IC$_{50}$ = 0.49 μM |
| 42 | IC$_{50}$ = 0.69 μM |
| 43 | IC$_{50}$ = 3.4 μM |
| 44 | 100% @ 10 μM, 50% @ 1 μM |
| 45 | 100% @ 10 μM, 40% @ 1 μM |
| 46 | 91% @ 10 μM, 41% @ 1 μM |
| 47 | 100% @ 10, 44% @ 1 μM |

TABLE 2

| Example Number | DBA/2 mice<br>% Protection Dose @ 30 mg/kg |
|---|---|
| 1 | 60% @ 30 mg/kg |
| 10 | 80% @ 30 mg/kg |
| 20 | 100% @ 10 mg/Kg |
| 22 | 100% @ 10 mg/kg |
| 23 | 40% @ 10 mg/kg |
| 25 | 80% @ 30 mg/kg |
| 32 | 60% @ 30 mg/kg |
| 35 | 20% @ 30 mg/Kg |
| 36 | 80% @ 30 mg/kg |
| 38 | 60% @ 30 mg/kg |
| 41 | 20% @ 30 mg/Kg |
| 42 | 20% @ 30 mg/kg |
| 44 | 20% @ 10 mg/kg |
| 47 | 80% @ 10 mg/kg |

What is claimed is: 1. A compound of Formula I

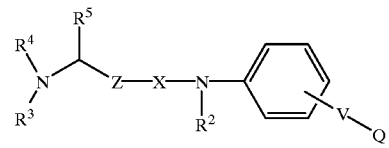

wherein

Z is —CH$_2$— or

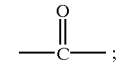

X is

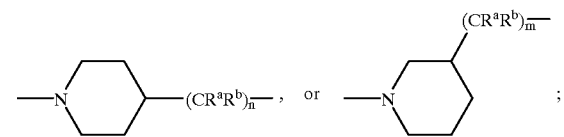

R$^5$ is C$_1$–C$_6$alkyl,

R$^2$ is hydrogen, C$_1$–C$_8$alkenyl, phenyl C$_1$–C$_8$alkyl, or C$_1$–C$_6$ substituted phenyl;

R$^3$ is hydrogen, C$_1$–C$_6$alkyl, or C$_2$–C$_6$alkenyl;

Q is aryl, C$_1$–C$_6$alkyl;

V is —O(CH$_2$)$_n$—, —O—, —(CH$_2$)$_n$, or —(CH$_2$)$_n$—O—;

R$^4$ is hydrogen, wherein each m is independently 1 to 3;

each n is independently 0 to 3;

each R$^a$ and R$^b$ is independently hydrogen, C$_1$–C$_6$alkyl, or R$^a$ and R$^b$ together with the carbon atom to which they are bonded form a C$_3$–C$_6$cycloalkyl ring;

and the pharmaceutically acceptable salts, esters, and amides, thereof.2. A compound in accordance with claim 1 wherein V is —OCH$_2$—, or —CH$_2$CH$_2$—, and Q is phenyl.3. A compound in accordance with claim 1 wherein X is

and Z is

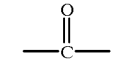

4. A compound according to claim 1 wherein R$^5$ is 3-methylbutyl or 2-methylbutyl.5. A compound according to claim 1 wherein R$^2$ is 3-methyl-but-2-enyl, or 3-methylbutyl, 2-methylpropyl, methyl, CH$_2$-cyclohexyl, n-butyl, or cyclohexyl.6. A compound according to claim 1 wherein V is —O—CH$_2$—, —C=C—, —CH$_2$—CH$_2$, or —NH—CH$_2$;

Q is phenyl, or C$_1$–C$_8$alkyl. 7. The compounds:

[S-(R*,R*)]-4-Methyl-2-(3-methyl-but-2-enylamino)-pentanoic acid {2-[(4-benzyloxy-phenyl)-(3-methyl-but-2-enyl)-amino]-1-methyl-ethyl}-amide;

[S-(R*,R*)]-4-Methyl-2-(3-methyl-butylamino)-pentanoic acid {2-[(4-benzyloxy-phenyl)-(3-methyl-but-2-enyl)-amino]-1-methyl-ethyl}-amide;

(S)-4-Methyl-2-[methyl-(3-methyl-butyl)-amino]-pentanoic acid {2-[(4-benzyloxy-phenyl)-cyclohex-2-enyl-amino]-1,1-dimethyl-ethyl}-amide. 8. The compounds:

1{4-[(4-Benzyloxy-phenyl)-(3-methyl-butyl)-amino]-piperidin-1-yl}-2-isopropylamino-4-methyl-pentan-1-one;

2-Benzylamino-1-{4-[(4-benzyloxy-phenyl)-(3-methyl-butyl)-amino]-piperidin-1-yl}-4-methyl-pentan-1-one;

1-{4-[(4-Benzyloxy-phenyl)-(3-methyl-butyl)-amino]-piperidin-1-yl}-4-methyl-2-(3-methyl-butylamino)-pentan-1-one;

1-{4-[(4-Benzyloxy-phenyl)-(3-methyl-butyl)-amino]-piperidin-1-yl}-2-cyclohexylamino-4-methyl-pentan-1-one;

1-{4-[(4-Benzyloxy-phenyl)-(3-methyl-butyl)-amino]-piperidin-1-yl}-2-dimethylamino-4-methyl-pentan-1-one; and 2-Isopropylamino-4-methyl-pentanoic acid {2-[(4-benzyloxy-phenyl)-(3-methyl-butyl)-amino]-ethyl}-amide. 9. A pharmaceutical composition comprising a compound of claim 1. 10. A method of treating pain, the method comprising administering to a patient having pain a therapeutically effective amount of a compound of claim 1.11. A compound of claim 1 wherein $R^5$ is 2-methylpropyl;

Z is

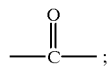

and

X is

12. A compound according to claim 29 wherein $R^3$ and $R^4$ are each independently hydrogen, and $R^2$ is —CH$_2$phenyl, $C_1$–$C_8$ alkenyl, or $C_1$–$C_8$ alkyl.13. A compound of claim 1 wherein $R^3$ and $R^4$ are hydrogen;

$R^5$ is 2-methyl propyl;

Z is —CH$_2$— or

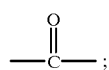

and

X is

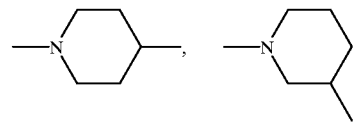

14. A compound of claim 1 wherein $R^3$ and $R^4$ are hydrogen;

$R^5$ is 2-methyl propyl;

Z is —CH$_2$— or

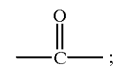

X is

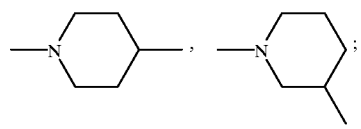

$R^2$ is $C_1$–$C_8$ alkyl, or $C_1$–$C_8$ alkenyl;
V is —OCH$_2$—, —(CH$_2$)$_n$—; and
Q is phenyl, substituted phenyl, $C_3$–$C_8$ cycloalkyl, and $C_1$–$C_6$ alkyl.15. A compound of claim 14 wherein $R^2$ is

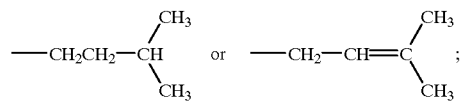

and
V—Q is —Obenzyl,

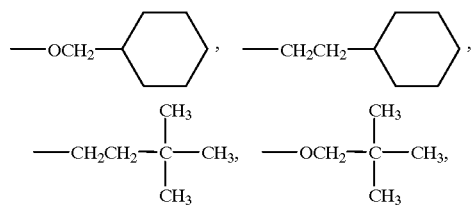

—O—CH$_2$-substituted phenyl, —CH$_2$CH$_2$-phenyl, or —CH$_2$CH$_2$-substituted phenyl.16. A compound of claim 1 wherein $R^3$ and $R^4$ are both hydrogen.17. The compounds:

(S)-2-Amino-1-{4-[(4-benzyloxy-phenyl)-(3-methyl-but-2-enyl)-amino]-piperidin-1-yl}-4-methyl-pentan-1-one;

(R)-2-Amino-1-{4-[(4-benzyloxy-phenyl)-(3-methyl-but-2-enyl)-amino]-piperidin-1-yl}-4methyl-pentan-1-one;

(S)-2-Amino-1-{4-[(4-benzyloxy-phenyl)-(3-methyl-but-2-enyl)-amino]-piperidin-1-yl}-3-methyl-pentan-1-one;

(S)-1-{4-[(4-Benzyloxy-phenyl)-(3-methyl-but-2-enyl)-amino]-piperidin-1-yl}-2-isopropylamino-4-methyl-pentan-1-one;

(S)-1-{4-[(4-Benzyloxy-phenyl)-(3-methyl-but-2-enyl)-amino]-piperidin-1-yl}-4-methyl-2-(3-methyl-butylamino)-pentan-1-one. 18. The compounds:

(S)-2-Amino-1-{4-[(4-benzyloxy-phenyl)-(3-methyl-butyl)-amino]-piperidin-1-yl}-4-methyl-pentan-1-one;

(S, R/S)-2-Amino-1-{3-[(4-benzyloxy-phenyl)-(3-methyl-but-2-enyl)-amino-]-piperidin-1-yl}-4-methyl-pentan-1-one;

(S)-2-Amino-1-{4-[(4-(4-fluorobenzyloxy)-phenyl)-(3-methyl-butyl)-amino]-piperidin-1-yl}-4-methyl-pentan-1-one;

(S)-[1-(2-Amino-4-methyl-pentyl)-piperidin-4-yl]-[4-(4-fluorobenzyloxy)-phenyl]-(3-methyl-butyl)-amine;

(S)-2-Amino-1-{4-[(4-phenethyl-phenyl)-(3-methyl-but-2-enyl)-amino]-piperidin-1-yl}-4-methyl-pentan-1-one;

(S)-[1-(2-Amino-4-methyl-pentyl)-piperidin-4-yl]-(4-benzyloxy-phenyl)-(3-methyl-but-2-enyl)-amine. 19. The compounds:

(S)-[1-(2-Amino-4-methyl-pentyl)-piperidin-4-yl]-(4-cyclohexylmethoxy-phenyl)-(3-methyl-butyl)-amine;

(S)-2-Amino-1-{4-[(4-cyclohexylmethoxy-phenyl)-(3-methyl-butyl)-amino]-piperidin-1-yl}-4-methyl-pentan-1-one;

(S)-[1-2-Amino-4-methyl-pentyl)-piperidin-4-yl]-[4-(2-cyclohexyl-ethyl)-phenyl]-(3-methyl-butyl)-amine;

(S)-2-Amino-1-{4-[[4-(2-cyclohexyl-ethyl)-phenyl]-(3-methyl-butyl)-amino]-piperidin-1-yl}-4-methyl-pentan-1-one;

(S)-[1-(2-Amino-4-methyl-pentyl)-piperidin-4-yl]-[4-(2,2-dimethyl-propoxy)-phenyl]-(3-methyl-butyl)-amine; and (S)-2-Amino-1-{4-[[4-(2,2-dimethyl-propoxy)-phenyl]-(3-methyl-butyl)-amino]-piperidin-1-yl}-4-methyl-pentan-1-one. 20. The compounds:

(S)-[1-(2-Amino-4-methyl-pentyl)-piperidin-4-yl]-[4-(3,3-dimethyl-butyl)-phenyl]-(3-methyl-butyl)-amine;

(S)-2-Amino-1-{4-[[4-(3,3-dimethyl-butyl)-phenyl]-(3-methyl-butyl)-amino]-piperidin-1-yl}-4-methyl-pentan-1-one;

(S)-[1-(2-Amino-4-methyl-pentyl)-piperidin-4-yl]-(4-benzyloxy-phenyl)-(3-methyl-but-2-enyl)-amine;

(S)-[1-(2-Amino-4-methyl-pentyl)-piperidin-4-yl]-(4-cyclohexylmethoxy-phenyl)-(3-methyl-but-2-enyl)-amine;

(S)-2-Amino-1-{4-[(4-cyclohexylmethoxy-phenyl)-(3-methyl-but-2-enyl)-amino]-piperidin-1-yl}-4-methyl-pentan-1-one;

(S)-[1-(2-Amino-4-methyl-pentyl)-piperidin-4-yl]-[4-(2-cyclohexyl-ethyl)-phenyl]-(3-methyl-but-2-enyl)-amine;

(S)-2-Amino-1-{4-[[4-(2-cyclohexyl-ethyl)-phenyl]-(3-methyl-but-2-enyl)-amino]-piperidin-1-yl}-4-methyl-pentan-1-one;

(S)-[1-(2-Amino-4-methyl-pentyl)-piperidin-4-yl]-[4-(2,2-dimethyl-propoxy)-phenyl]-(3-methyl-but-2-enyl)-amine; and (S)-2-Amino-1-{4-[[4-(2,2-dimethyl-propoxy)-phenyl]-(3-methyl-but-2-enyl)-amino]-piperidin-1-yl}-4-methyl-pentan-1-one. 21. The compounds:

(S)-[1-(2-Amino-4-methyl-pentyl)-piperidin-4-yl]-[4-(3,3-dimethyl-butyl)-phenyl]-(3-methyl-but-2-enyl)-amine;

(S)-2-Amino-1-{[[4-(3,3-dimethyl-butyl)-phenyl]-(3-methyl-but-2-enyl)-amino]-piperidin-1-yl}-4-methyl-pentan-1-one;

(S)-[1-2-Amino-4-methyl-pentyl)-piperidin-4-yl]-[4-(4-chloro-benzyloxy)-phenyl]-(3-methyl-but-2-enyl)-amine;

(S)-2-Amino-1-{4-[[4-(4-chloro-benzyloxy)-phenyl]-(3-methyl-but-2-enyl)-amino]-piperidin-1-yl}-4-methyl-pentan-1-one;

(S)-[1-(2-Amino-4-methyl-pentyl)-piperidin-4-yl]-{4-[2-(4-fluoro-phenyl)-ethyl]-phenyl}-(3-methyl-but-2-enyl)-amine;

(S)-2-Amino-1-{4-[{4-[2-(4-fluoro-phenyl)-ethyl]-phenyl}-(3-methyl-but-2-enyl)-amino]-piperidin-1-yl}-4-methyl-pentan-1-one;

(S)-[1-(2-Amino-4-methyl-pentyl)-piperidin-4-yl]-3-methyl-but-2-enyl)-(4-phenethyl-phenyl)-amine; and (S)-[1-(2-Amino-4-methyl-pentyl)-piperidin-4-yl]-{4-[2-(4-chloro-phenyl)-ethyl]-phenyl}-(3-methyl-but-2-enyl)-amine.22. The compounds:

(S)-[1-(2-Amino-4-methyl-pentyl)-piperidin-4-yl]-[4-(4-chloro-benzyloxy)-phenyl]-(3-methyl-but-2-enyl)-amine.23. The compounds:

(S)-2-Amino-1-{4-[[4-(4-chloro-benzyloxy)-phenyl]-(3-methyl-but-2-enyl)-amino]-piperidin-1-yl}-4-methyl-pentan-1-one;

(S)-[1-(2-Amino-4-methyl-pentyl)-piperidin-4-yl]-{4-[2-(4-fluoro-phenyl)-ethyl]-phenyl}-(3-methyl-butyl)-amine;

(S)-2-Amino-1-{4-[{4-[2-(4-fluoro-phenyl)-ethyl]-phenyl}-(3-methyl-butyl)-amino]-piperidin-1-yl}-4-methyl-pentan-1-one; and (S)-[1-(2-Amino-4-methyl-pentyl)-piperidin-4-yl]-(3-methyl-butyl)-(4-phenethyl-phenyl)-amine.24. The compounds:

(S)-2-Amino-4-methyl-1-{4-[(3-methyl-butyl)-(4-phenethyl-phenyl)-amino]-piperidin-1-yl}-pentan-1-one;

(S)-[1-(2-Amino-4-methyl-pentyl)-piperidin-4-yl]-{4-[2-(4-chloro-phenyl)-ethyl]-phenyl}-(3-methyl-butyl)-amine;

(S)-2-Amino-1-{4-[{4-[2-(4-chloro-phenyl)-ethyl]-phenyl}-(3-methyl-butyl)-amino]-piperidin-1-yl}-4-methyl-pentan-1-one;

(S)-[1-2-Amino-4-methyl-pentyl)-piperidin-3-yl]-(4-benzyloxy-phenyl)-(3-methyl-butyl)-amine;

(S)-2-Amino-1-{3-[(4-benzyloxy-phenyl)-(3-methyl-butyl)-amino]-piperidin-1-yl}-4-methyl-pentan-1-one; and (S)-[1-(2-Amino-4-methyl-pentyl)-piperidin-3-yl]-(4-cyclohexylmethoxy-phenyl)-(3-methyl-butyl)-amine. 25. The compounds:

(S)-2-Amino-1-{3-[(4-cyclohexylmethoxy-phenyl)-(3-methyl-butyl)-amino]-piperidin-1-yl}-4-methyl-pentan-1-one;

(S)-[1-(2-Amino-4-methyl-pentyl)-piperidin-3-yl]-[4-(2-cyclohexyl-ethyl)-phenyl]-(3-methyl-butyl)-amine;

(S)-2-Amino-1-{3-[[4-(2-cyclohexyl-ethyl)-phenyl]-(3-methyl-butyl)-amino]-piperidin-1-yl}-4-methyl-pentan-1-one;

(S)-[1-(2-Amino-4-methyl-pentyl)-piperidin-3-yl]-[4-(2,2-dimethyl-propoxy)-phenyl]-(3-methyl-butyl)-amine;

(S)-2-Amino-1-{3-[[4-(2,2-dimethyl-propoxy)-phenyl]-(3-methyl-butyl)-amino]-piperidin-1-yl}-4-methyl-pentan-1-one;

(S)-[1-(2-Amino-4-methyl-pentyl)-piperidin-3-yl]-[4-(3,3-dimethyl-butyl)-phenyl]-(3-methyl-butyl)-amine;

(S)-2-Amino-1-{3-[[4-(3,3-dimethyl-butyl)-phenyl]-(3-methyl-butyl)-amino]-piperidin-1-yl}-4-methyl-pentan-1-one;

(S)-2-Amino-1-{3-[(4-benzyloxy-phenyl)-(3-methyl-but-2-enyl)-amino]-piperidin-1-yl}-4-methyl-pentan-1-one;

(S)-[1-(2-Amino-4-methyl-pentyl)-piperidin-3-yl]-(4-cyclohexylmethoxy-phenyl)-(3-methyl-but-2-enyl)-amine; and (S)-2-Amino-1-{3-[(4-cyclohexylmethoxy-phenyl)-(3-methyl-but-2-enyl)-amino]-piperidin-1-yl}-4-methyl-pentan-1-one.26. The compounds:

(S)-[1-(2-Amino-4-methyl-pentyl)-piperidin-3-yl]-[4-(2-cyclohexyl-ethyl)-phenyl]-(3-methyl-but-2-enyl)-amine;

(S)-2-Amino-1-{3-[[4-(2-cyclohexyl-ethyl)-phenyl]-(3-methyl-but-2-enyl)-amino]-piperidin-1-yl}-4-methyl-pentan-1-one;

(S)-[1-(2-Amino-4-methyl-pentyl)-piperidin-3-yl]-[4-(2,2-dimethyl-propoxy)-phenyl]-(3-methyl-but-2-enyl)-amine;

(S)-2-Amino-1-{3-[[4-(2,2-dimethyl-propoxy)-phenyl]-(3-methyl-but-2-enyl)-amino]-piperidin-1-yl}-4-methyl-pentan-1-one;

(S)-2-Amino-1-{3-[[4-(3,3-dimethyl-butyl)-phenyl]-(3-methyl-but-2-enyl)-amino]-piperidin-1-yl}-4-methyl-pentan-1-one;

(S)-[1-(2-Amino-4-methyl-pentyl)-piperidin-3-yl]-[4-(3,3-dimethyl-butyl)-phenyl]-(3-methyl-but-2-enyl)-amine;

(S)-[1-(2-Amino-4-methyl-pentyl)-piperidin-3-yl]-[4-(4-chloro-benzyloxy)-phenyl]-(3-methyl-but-2-enyl)-amine;

(S)-2-Amino-1-{3-[[4-(4-chloro-benzyloxy)-phenyl]-(3-methyl-but- 2-enyl)-amino]-piperidin-1-yl)}-4-methyl-pentan-1-one; and (S)-[1-(2-Amino-4-methyl-pentyl)-piperidin-3-yl]-{4-[2-(4-fluoro-phenyl)-ethyl]-phenyl}-(3-methyl-but-2-enyl)-amine.27. The compounds:

(S)-2-Amino-1-{3-[{4-[2-(4-fluoro-phenyl)-ethyl]-phenyl}-(3-methyl-but-2-enyl)-amino]-piperidin-1-yl}-4-methyl-pentan-1-one;

(S)-[1-(2-Amino-4-methyl-pentyl)-piperidin-3-yl]-(3-methyl-but-2-enyl)-(4-phenethyl-phenyl)-amine;

(S)-2-Amino-4-methyl-1-{3-[(3-methyl-but-2-enyl)-4-phenethyl-phenyl)-amino]-piperidin-1-yl}-pentan-1-one;

(S)-[1-(2-Amino-4-methyl-pentyl)-piperidin-3-yl]-{4-[2-(4-chloro-phenyl)-ethyl]-phenyl}-(3-methyl-but-2-enyl)-amine;

(S)-2-Amino-1-{3-[(4-[2-(4-chloro-phenyl)-ethyl]-phenyl}-(3-methyl-but-2-enyl)-amino]-piperidin-1-yl}-4-methyl-pentan-1-one;

(S)-[1-(2-Amino-4-methyl-pentyl)-piperidin-3-yl]-[4-(4-chloro-benzyloxy)-phenyl]-(3-methyl-butyl)-amine;

(S)-2-Amino-1-{3-[[4-(4-chloro-benzyloxy)-phenyl]-(3-methyl-butyl)-amino]-piperidin-1-yl}-4-methyl-pentan-1-one;

(S)-[1-(2-Amino-4-methyl-pentyl)-piperidin-3-yl]-{4-[2-(4-fluoro-phenyl)-ethyl]-phenyl}-(3-methyl-butyl)-amine; and (S)-2-Amino-1-{3-[{4-[2-(4-fluoro-phenyl)-ethyl]-phenyl}-(3-methyl-butyl)-amino]-piperidin-1-yl}-4-methyl-pentan-1-one.28. The compounds:

(S)-[1-(2-Amino-4-methyl-pentyl)-piperidin-3-yl]-(3-methyl-butyl)-(4-phenethyl-phenyl)-amine;

(S)-2-Amino-4-methyl-1-{3-[(3-methyl-butyl)-(4-phenethyl-phenyl)-amino]-piperidin-1-yl}-pentan-1-one;

(S)-[1-(2-Amino-4-methyl-pentyl)-piperidin-3-yl]-{4-[2-4-chloro-phenyl)-ethyl]-phenyl}-(3-methyl-butyl)-amine;

(S)-2-Amino-1-{3-[{4-[2-4-chloro-phenyl)-ethyl]-phenyl}-(3-methyl-butyl)-amino]-piperidin-1-yl}-4-methyl-pentan-1-one. 29. The compounds:

(S)-Benzoic acid 4-[[1-(2-amino-4-methyl-pentyl)-piperidin-3-yl]-(3-methyl-but-2-enyl)-amino]-phenyl ester.30. The compounds:

(R)-[1-(2-Amino-4-methyl-pentyl)-piperidin-4-yl]-(4-benzyloxy-phenyl)-(3-methyl-butyl)-amine;

(R)-2-Amino-1-{4-[(4-benzyloxy-phenyl)-(3-methyl-butyl)-amino]-piperidin-1-yl}-4-methyl-pentan-1-one;

(R)-[1-(2-Amino-4-methyl-pentyl)-piperidin-4-yl]-(4-cyclohexylmethoxy-phenyl)-(3-methyl-butyl)-amine;

(R)-2-Amino-1-{4-[(4-cyclohexylmethoxy-phenyl)-(3-methyl-butyl)-amino]-piperidin-1-yl}-4-methyl-pentan-1-one;

(R)-[-1-(2-Amino-4-methyl-pentyl)-piperidin-4-yl]-[4-(2-cyclohexyl-ethyl)-phenyl]-(3-methyl-butyl)-amine;

(R)-2-Amino-1-{4-[[4-(2-cyclohexyl-ethyl)-phenyl]-(3-methyl-butyl)-amino]-piperidin-1-yl}-4-methyl-pentan-1-one;

(R)-[1-(2-Amino-4-methyl-pentyl)-piperidin-4-yl]-[4-(2,2-dimethyl-propoxy)-phenyl]-3-methyl-butyl)-amine;

(R)-2-Amino-1-{4-[[4-(2,2-dimethyl-propoxy)-phenyl]-(3-methyl-butyl)-amino]-piperidin-1-yl}-4-methyl-pentan-1-one;

(R)-[1-(2-Amino-4-methyl-pentyl)-piperidin-4-yl]-[4-(3,3-dimethyl-butyl)-phenyl]-(3-methyl-butyl)-amine; and (R)-2-Amino-1-{4-[[4-(3,3-dimethyl-butyl)-phenyl]-(3-methyl-butyl)-amino]-piperidin-1-yl}-4-methyl-pentan-1-one.31. The compounds:

(R)-[1-(2-Amino-4-methyl-pentyl)-piperidin-4-yl]-(4-benzyloxy-phenyl)-(3-methyl-but-2-enyl)-amine;

(R)-[1-(2-Amino-4-methyl-pentyl)-piperidin-4-yl]-[4-(2-cyclohexyl-ethyl)-phenyl]-(3-methyl-but-2-enyl)-amine;

(R)-2-Amino-1-{4-[[4-(2-cyclohexyl-ethyl)-phenyl]-(3-methyl-but-2-enyl)-amino]-piperidin-1-yl}-4-methyl-pentan-1-one;

(R)-[1-(2-Amino-4-methyl-pentyl)-piperidin-4-yl]-[4-(3,3-dimethyl-butyl)-phenyl]-(3-methyl-but-2-enyl)-amine;

(R)-2-Amino-1-{4-[[4-(3,3-dimethyl-butyl)-phenyl]-(3-methyl-but-2-enyl)-amino]-piperidin-1-yl}-4-methyl-pentan-1-one;

(R)-[1-(2-Amino-4-methyl-pentyl)-piperidin-4-yl]-[4-(4-chloro-benzyloxy)-phenyl]-(3-methyl-butyl)-amine;

(R)-2-Amino-1-{4-[[4-(4-chloro-benzyloxy)-phenyl]-(3-methyl-butyl)-amino]-piperidin-1-yl}-4-methyl-pentan-1-one;

(R)-[1-(2-Amino-4-methyl-pentyl)-piperidin-4-yl]-{4-[2-(4-fluoro-phenyl)-ethyl]-phenyl}-(3-methyl-butyl)-amine;

(R)-2-Amino-1-{4-[{4-[2-(4-fluoro-phenyl)-ethyl]-phenyl}-(3-methyl-but-2-enyl)-amino]-piperidin-1-yl}-4-methyl-pentan-1-one; and (R)-[1-(2-Amino-4-methyl-pentyl)-piperidin-4-yl]-(3-methyl-but-2-enyl)-(4-phenethyl-phenyl)-amine.32. The compounds:

(R)-2-Amino-4-methyl-1-{4-[(3-methyl-but-2-enyl)-(4-phenethyl-phenyl)-amino]-piperidin-1-yl}-pentan-1-one;

(R)-[1-(2-Amino-4-methyl-pentyl)-piperidin-4-yl]-{4-[2-(4-chloro-phenyl)-ethyl]-phenyl}-(3-methyl-but-2-enyl)-amine;

(R)-2-Amino-1-{4-[{4-[2-(4-chloro-phenyl)-ethyl]-phenyl}-(3-methyl-but-2-enyl)-amino]-piperidin-1-yl}-4-methyl-pentan-1-one;

(R)-[1-(2-Amino-4-methyl-pentyl)-piperidin-4-yl]-[4-(4-fluoro-benzyloxy)-phenyl](3-methyl-butyl)-amine;

(R)-2-Amino-1-{4-[[4-(4-fluoro-benzyloxy)-phenyl]-(3-methyl-butyl)-amino]-piperidin-1-yl)}-4-methyl-pentan-1-one;

(R)-[1-(2-Amino-4-methyl-pentyl)-piperidin-4-yl]-{4-[2-(4-fluoro-phenyl)-ethyl]-phenyl}-(3-methyl-butyl)-amine;

(R)-2-Amino-1-{4-[{4-[2-4-fluoro-phenyl)-ethyl]-phenyl}-(3-methyl-butyl)-amino]-piperidin-1-yl}-4-methyl-pentan-1-one;

(R)-[1-(2-Amino-4-methyl-pentyl)-piperidin-4-yl]-(3-methyl-butyl)-(4-phenethyl-phenyl)-amine;

(R)-2-Amino-4-methyl-1-{4-[(3-methyl-butyl)-(4-phenethyl-phenyl)-amino]-piperidin-1-yl}-pentan-1-one; and (R)-[1-(2-Amino-4-methyl-pentyl)-piperidin-4-yl]-{4-[2-(4-chloro-phenyl)-ethyl]-phenyl}-(3-methyl-butyl)-amine.33. The compounds:

(R)-2-Amino-1-{4-[{4-[2-(4-chloro-phenyl)-ethyl]-phenyl}-(3-methyl-butyl)-amino]-piperidin-1-yl}-4-methyl-pentan-1-one;

(S)-[1-(2-Amino-3-methyl-pentyl)-piperidin-4-yl]-(4-benzyloxy-phenyl)-(3-methyl-butyl)-amine;

(S)-2-Amino-1-{4-[(4-benzyloxy-phenyl)-(3-methyl-butyl)-amino)-piperidin-1-yl}-3-methyl-pentan-1-one;

(S)-[1-(2-Amino-3-methyl-pentyl)-piperidin-4-yl]-(4-cyclohexylmethoxy-phenyl)-(3-methyl-butyl)-amine;

(S)-2-Amino-1-{4-[(4-cyclohexylmethoxy-phenyl)-(3-methyl-butyl)-amino]-piperidin-1-yl}-3-methyl-pentan-1-one;

(S)-[1-(2-Amino-3-methyl-pentyl)-piperidin-4-yl]-[4-(2-cyclohexyl-ethyl)-phenyl]-(3-methyl-butyl)-amine;

(S)-2-Amino-1-{4-[[4-(2-cyclohexyl-ethyl)-phenyl]-(3-methyl-butyl)-amino]-piperidin-1-yl}-3-methyl-pentan-1-one;

(S)-[1-(2-Amino-3-methyl-pentyl)-piperidin-4-yl]-[4-(2,2-dimethyl-propoxy)-phenyl]-(3-methyl-butyl)-amine;

(S)-2-Amino-1-{4-[[4-(2,2-dimethyl-propoxy)-phenyl]-(3-methyl-butyl)-amino]-piperidin-1-yl}-3-methyl-pentan-1-one;

(S)-[1-(2-Amino-3-methyl-pentyl)-piperidin-4-yl]-[4-(3,3-dimethyl-butyl)-phenyl]-(3-methyl-butyl)-amine; and (S)-2-Amino-1-{4-[[4-(3,3-dimethyl-butyl)-phenyl]-(3-methyl-butyl)-amino]-piperidin-1-yl}-3-methyl-pentan-1-one.34. The compounds:

(S)-[1-(2-Amino-3-methyl-pentyl)-piperidin-4-yl]-(4-benzyloxy-phenyl)-(3-methyl-but-2-enyl)-amine;

(S)-[1-(2-Amino-3-methyl-pentyl)-piperidin-4-yl]-[4-(4-fluorobenzyloxy)-phenyl]-(3-methyl-butyl)-amine;

(S)-2-Amino-1-{4-[(4-(4-fluorobenzyloxy)-phenyl)-(3-methyl-butyl)-amino]-piperidin-1-yl}-3-methyl-pentan-1-one;

(S)-[1-(2-Amino-3-methyl-pentyl)-piperidin-4-yl]-[4-(2-cyclohexyl-ethyl)-phenyl]-(3-methyl-but-2-enyl)-amine;

(S)-2-Amino-1-{4-[[4-(2-cyclohexyl-ethyl)-phenyl]-(3-methyl-but-2-enyl)-amino]-piperidin-1-yl}-3-methyl-pentan-1-one;

(S)-[1-(2-Amino-3-methyl-pentyl)-piperidin-4-yl]-[4-(3,3-dimethyl-butyl)-phenyl]-(3-methyl-but-2-enyl)-amine;

(S)-2-Amino-1-{4-[[4-(3,3-dimethyl-butyl)-phenyl]-(3-methyl-but-2-enyl)-amino]-piperidin-1-yl}-3-methyl-pentan-1-one;

(S)-[1-(2-Amino-3-methyl-pentyl)-piperidin-4-yl]-[4-(4-chloro-benzyloxy)-phenyl]-(3-methyl-butyl)-amine;

(S)-2-Amino-1-{(4-[[4-(4-chloro-benzyloxy)-phenyl]-(3-methyl-butyl)-amino]-piperidin-1-yl}-3-methyl-pentan-1-one; and (S)-[1(2-Amino-3-methyl-pentyl)-piperidin-4-yl]-{4-[2-(4-fluoro-phenyl)-ethyl-]-phenyl}-(3-methyl-butyl)-amine.35. The compounds:

(S)-2-Amino-1-{4-[{4-[2-(4-fluoro-phenyl)-ethyl]-phenyl}-(3-methyl-but-2-enyl)-amino]-piperidin-1-yl}-3-methyl-pentan-1-one;

(S)-[1-(2-Amino-3-methyl-pentyl)-piperidin-4-yl]-(3-methyl-but-2-enyl)-(4-phenethyl-phenyl)-amine;

(S)-2-Amino-3-methyl-1-{4-[(3-methyl-but-2-enyl)-(4-phenethyl-phenyl)-amino-]-piperidin-1-yl}-pentan-1-one;

(S)-[1-(2-Amino-3-methyl-pentyl)-piperidin-4-yl]-{4-[2-(4-chloro-phenyl)-ethyl]-phenyl}-(3-methyl-but-2-enyl)-amine;

(S)-2-Amino-1-{4-[{4-[2-(4-chloro-phenyl)-ethyl]-phenyl}-(3-methyl-but-2-enyl)-amino]-piperidin-1-yl}-3-methyl-pentan-1-one;

(S)-[1-(2-Amino-4-methyl-pentyl)-piperidin-4-yl]-[4-(4-fluoro-benzyloxy)-phenyl]-(3-methyl -butyl)-amine;

(S)-2-Amino-1-{4-[[4-(4-fluoro-benzyloxy)-phenyl]-(3-methyl-butyl)-amino]-piperidin-1-yl}-4-methyl-pentan-1-one;

(S)-[1-(2-Amino-3-methyl-pentyl)-piperidin-4-yl]-{4-[2-(4-fluoro-phenyl)-ethyl]-phenyl}-(3-methyl-butyl)-amine;

(S)-2-Amino-1-{4-[{4-[2-(4-fluoro-phenyl)-ethyl]-phenyl}-(3-methyl-butyl)-amino]-piperidin-1-yl}-3-methyl-pentan-1-one;

(S)-[1-(2-Amino-3-methyl-pentyl)-piperidin-4-yl]-(3-methyl-butyl)-(4-phenethyl-phenyl)-amine;

(S)-2-Amino-3-methyl-1-{4-[(3-methyl-butyl)-(4-phenethyl-phenyl)-amino]-piperidin-1-yl}-pentan-1-one;

(S)-[1-(2-Amino-3-methyl-pentyl)-piperidin-4-yl]-{4-[2-(4-chloro-phenyl)-ethyl]-phenyl}-(3-methyl-butyl)-amine; and (S)-2-Amino-1-{4-[{4-[2-(4-chloro-phenyl)-ethyl]-phenyl}-(3-methyl-butyl)-amino]-piperidin-1-yl}-3-methyl-pentan-1-one.

* * * * *